US011806283B2

(12) United States Patent
Gray et al.

(10) Patent No.: US 11,806,283 B2
(45) Date of Patent: Nov. 7, 2023

(54) METHODS AND SYSTEMS TO PROVIDE EXCLUDED DEFINED ZONES FOR INCREASING ACCOMMODATIVE AMPLITUDE

(71) Applicant: Lensar, Inc., Orlando, FL (US)

(72) Inventors: Gary P. Gray, Orlando, FL (US); Rudolph W. Frey, Winter Park, FL (US)

(73) Assignee: Lensar, Inc., Orlando, FL (US)

(*) Notice: Subject to any disclaimer, the term of this patent is extended or adjusted under 35 U.S.C. 154(b) by 360 days.

(21) Appl. No.: 16/284,636

(22) Filed: Feb. 25, 2019

(65) Prior Publication Data

US 2019/0290489 A1 Sep. 26, 2019

Related U.S. Application Data

(62) Division of application No. 14/224,012, filed on Mar. 24, 2014, now Pat. No. 10,213,340.

(51) Int. Cl.
*A61F 9/008* (2006.01)

(52) U.S. Cl.
CPC ...... *A61F 9/00808* (2013.01); *A61F 9/00827* (2013.01); *A61F 9/00838* (2013.01); *A61F 2009/0087* (2013.01); *A61F 2009/00844* (2013.01); *A61F 2009/00872* (2013.01); *A61F 2009/00887* (2013.01); *A61F 2009/00889* (2013.01); *A61F 2009/00895* (2013.01)

(58) Field of Classification Search
CPC .. A61F 9/008; A61F 9/00802; A61F 9/00804; A61F 9/00808; A61F 9/00812; A61F 9/00825; A61F 9/00834; A61F 9/00838; A61F 2009/00861; A61F 2009/0087; A61F 2009/00878; A61F 2009/00887; A61F 2009/00889; A61F 2009/00895; A61F 2009/00897
USPC .......... 606/3–6, 10–12; 607/88, 89; 128/898
See application file for complete search history.

(56) References Cited

U.S. PATENT DOCUMENTS

| | | | |
|---|---|---|---|
| 4,538,608 | A | 9/1985 | L'Esperance |
| 4,764,930 | A | 8/1988 | Bille |
| 4,901,718 | A | 2/1990 | Bille |
| 4,907,586 | A | 3/1990 | Bille |
| 5,098,426 | A | 3/1992 | Sklar |
| 5,246,435 | A | 9/1993 | Bille |
| 5,355,181 | A | 10/1994 | Ashizaki |
| 5,439,462 | A | 8/1995 | Bille |
| 5,480,396 | A | 1/1996 | Simon |
| 6,004,314 | A | 12/1999 | Wei |
| 6,099,522 | A | 8/2000 | Knopp |
| 6,197,018 | B1 | 3/2001 | O'Donnell |
| 6,312,422 | B1 | 6/2001 | Dubnack |
| 6,322,556 | B1 | 11/2001 | Gwon |
| 6,325,792 | B1 | 12/2001 | Swinger |

(Continued)

*Primary Examiner* — Ahmed M Farah
(74) *Attorney, Agent, or Firm* — Glen P. Belvis; Belvis Law, LLC.

(57) ABSTRACT

Systems and methods for increasing the amplitude of accommodation of an eye, changing the refractive power of lens material of a natural crystalline lens of the eye, and addressing presbyopia are is provided. Generally, there are provided methods and systems for delivering a laser beam to a lens of an eye in a plurality of laser shots, which are in precise and predetermined patterns results in the weakening of the lens material.

15 Claims, 43 Drawing Sheets

(56) References Cited

U.S. PATENT DOCUMENTS

| | | | |
|---|---|---|---|
| 7,655,002 B2* | 2/2010 | Myers | A61F 9/008 606/5 |
| 8,262,646 B2* | 9/2012 | Frey | A61F 9/00838 606/4 |
| 8,382,745 B2 | 2/2013 | Naranjo-Tackman | |
| 8,394,084 B2 | 3/2013 | Optimedica | |
| 8,403,921 B2 | 3/2013 | Optimedica | |
| 8,425,497 B2 | 4/2013 | Optimedica | |
| 8,465,478 B2 | 6/2013 | Frey | |
| 8,480,659 B2 | 7/2013 | Frey | |
| 8,500,723 B2 | 8/2013 | Frey | |
| 8,617,146 B2 | 12/2013 | Frey | |
| 8,758,332 B2 | 6/2014 | Frey | |
| 8,801,186 B2 | 8/2014 | Frey | |
| 9,180,051 B2* | 11/2015 | Frey | A61F 9/008 |
| 9,375,349 B2* | 6/2016 | Frey | A61F 9/008 |
| 9,545,338 B2 | 1/2017 | Frey | |
| 9,968,485 B2 | 5/2018 | Potter | |
| 10,213,340 B2* | 2/2019 | Gray | A61F 9/00838 |
| 10,667,950 B2* | 6/2020 | Gray | A61F 9/00838 |
| 10,709,610 B2 | 7/2020 | Morley | |
| 11,090,190 B2 | 8/2021 | Morley | |
| 11,607,339 B2* | 3/2023 | Teuma | A61F 9/00838 |
| 2002/0103478 A1 | 8/2002 | Gwon | |
| 2004/0199149 A1* | 10/2004 | Myers | A61F 9/008 606/4 |
| 2006/0100677 A1* | 5/2006 | Blumenkranz | A61F 9/00821 607/89 |
| 2007/0129775 A1* | 6/2007 | Mordaunt | A61F 9/008 606/4 |
| 2007/0173794 A1 | 7/2007 | Frey | |
| 2007/0185475 A1 | 8/2007 | Frey | |
| 2008/0287928 A1 | 11/2008 | Arnoldussen | |
| 2010/0004641 A1 | 1/2010 | Frey | |
| 2011/0160709 A1* | 6/2011 | McArdle | A61F 9/00825 606/4 |
| 2011/0190739 A1 | 8/2011 | Frey | |
| 2012/0016350 A1 | 1/2012 | Myers | |
| 2016/0095752 A1 | 4/2016 | Srinivasan | |
| 2016/0302971 A1 | 10/2016 | Frey | |
| 2017/0290703 A1 | 10/2017 | Teuma | |
| 2018/0085256 A1 | 3/2018 | Gray | |
| 2021/0137738 A1* | 5/2021 | Morley | A61F 9/00825 |

* cited by examiner

ANTERIOR ⟷ POSTERIOR

ANTERIOR ⟷ POSTERIOR

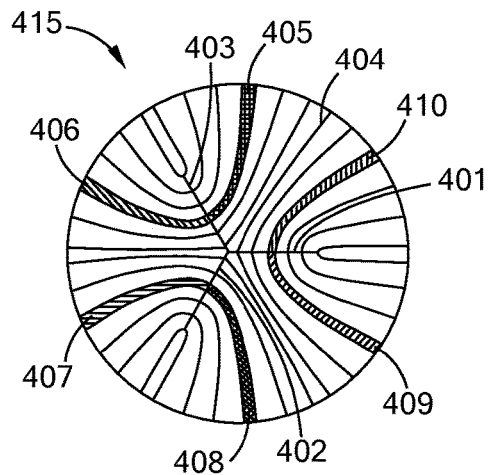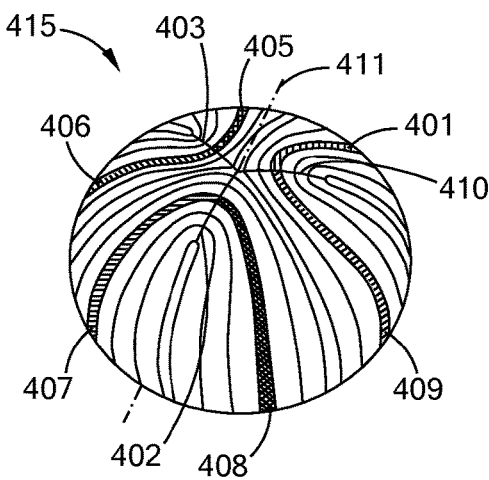
FIG. 4A   FIG. 4B
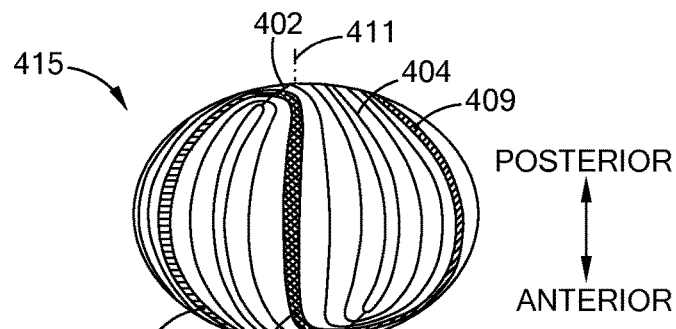
FIG. 4C
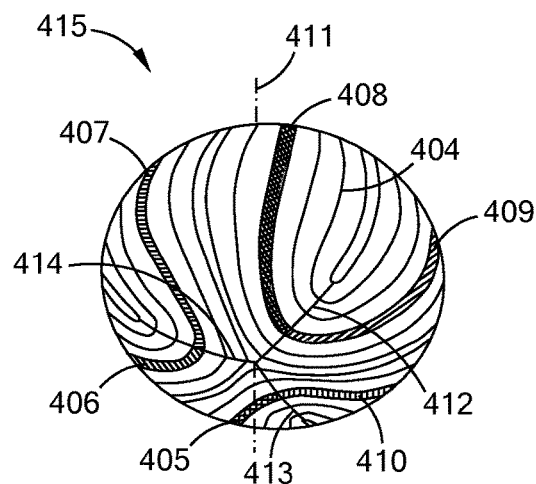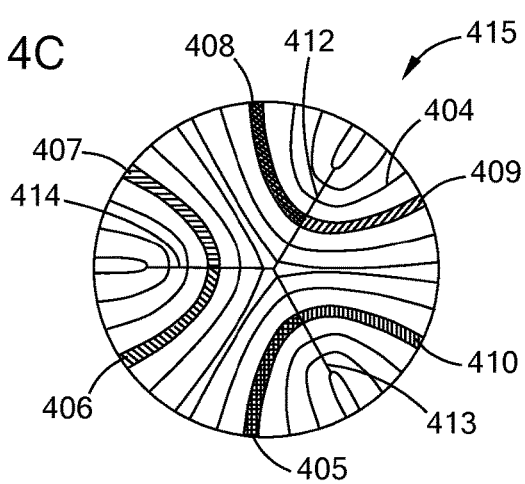
FIG. 4D   FIG. 4E

METHODS AND SYSTEMS TO PROVIDE EXCLUDED DEFINED ZONES FOR INCREASING ACCOMMODATIVE AMPLITUDE This application is a divisional of Ser. No. 14/224,012, filed Mar. 24, 2014, which the entire disclosures of each of which are incorporated herein by reference.

BACKGROUND OF THE INVENTION

Field of the Invention

The present invention relates to systems and methods for treating the structure of the natural human crystalline lens with a laser to address a variety of medical conditions such as presbyopia, refractive error and cataracts and combinations of these.

The anatomical structures of the eye are shown in general in FIG. 1, which is a cross sectional view of the eye. The sclera 131 is the white tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil). The ocular or natural crystalline lens 103, a more detailed picture of which is shown in FIG. 1A, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil, then proceeds through the ocular lens 103 through the vitreous 110 along the visual axis 104, strikes the retina 105 at the back of the eye, forming an image at the macula 106 that is transferred by the optic nerve 107 to the brain. The space between the cornea 101 and the retina 105 is filled with a liquid called the aqueous 117 in the anterior chamber 109 and the vitreous 110, a gel-like clear substance, in the chamber posterior to the lens 103.

FIG. 1A illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 1 and 1A. The anterior and posterior sides of the lens have different curvatures and the cortex and the different nuclei in general follow those curvatures. Thus, the lens can be viewed as essentially a stratified structure that is asymmetrical along the equatorial axis and consisting of long crescent fiber cells arranged end to end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

Compaction of the lens occurs with aging. The number of lens fibers that grow each year is relatively constant throughout life. However, the size of the lens does not become as large as expected from new fiber growth. The lens grows from birth through age 3, from 6 mm to 7.2 mm or 20% growth in only 3 years. Then the next approximate decade, growth is from 7.2 mm to 9 mm or 25%; however, this is over a 3 times longer period of 9 years. Over the next approximate 2 decades, from age 12 to age 36 the lens grows from 9 mm to 9.6 mm or 6.7% growth in 24 years, showing a dramatically slowing observed growth rate, while we believe there is a relatively constant rate of fiber growth during this period. Finally, in the last approximately 2 decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

In general, presbyopia is the loss of accommodative amplitude. In general refractive error is typically due to variations in the axial length of the eye. Myopia is when the eye is too long resulting in the focus falling in front of the retina. Hyperopia is when the eye is too short resulting in the focus falling behind the retina. In generally, cataracts are areas of opacification of the ocular lens which are sufficient to interfere with vision. Other conditions, for which the present invention is directed, include but are not limited to the opacification of the ocular lens.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population.

Accommodative amplitude has been shown to decline with age steadily through the fifth decade of life.

Although the invention is not bound by it, the present specification postulates a different theory of how this loss of lens flexibility occurs to cause presbyopia. In general, it is postulated that the structure of the lens rather than the material properties of the lens plays a greater role in loss of flexibility and resultant presbyopia than was previously understood. Thus, contrary to the teachings of the prior studies in this field as set forth above, material elasticity is not the dominate cause of presbyopia. Rather, it is postulated that it is the structure of the lens and changes in that structure with age that is the dominant cause of presbyopia. Thus, without being limited to or bound by this theory, embodiments of the present invention discloses a variety of methods and systems to provide laser treatments to increase the flexibility of the lens, based at least in part on the structure of the lens and structural changes that occur to the lens with aging. Embodiments of the present invention further discloses providing laser treatments to increase the flexibility of the lens that are based primarily on the structure of the lens and structural changes that occur to the lens with aging.

Under the prior theories and treatments for presbyopia, the direction was principally toward the material properties, i.e., Modulus of the material, rather than on the structure, i.e., whether the layers were bound together. On the other hand, the presently postulated theory is directed toward structural features and the effects that altering those features have on flexibility.

In general, current presbyopia treatments tend to be directed toward alternatives to increasing the amplitude of accommodation of the natural crystalline lens. These treatments include a new class of artificial accommodative Intraocular Lenses (IOL's), such as the Eyeonics CRYSTAL-ENS, which are designed to change position within the eye; however, they offer only about 1 diopter of objectively measured accommodative amplitude, while many practitioners presently believe 3 or more diopters are required to restore normal visual function for near and far objects. Moreover, researchers are pursuing techniques and materials to refill the lens capsule with synthetic materials. Additionally, present surgical techniques to implant artificial accommodative IOL's are those developed for the more serious condition of cataracts. It is believed that practitioners are reluctant at the present time to replace a patient's clear albeit presbyopic natural crystalline lens, with an accommodative IOL due to the risks of this invasive surgical technique on a patient who may simply wear reading glasses to correct the near vision deficiency. However, developments may offer greater levels of accommodative amplitude in implantable devices and refilling materials.

SUMMARY

There has existed a long standing need for improved methods of increasing the accommodative amplitude of the eye, changing the refractive power of the natural human lens, changing the refractive power of the eye, and generally addressing the condition of presbyopia. The present inventions, among other things, solve these and other needs by providing the articles of manufacture, devices and processes set forth in this specification.

Thus, there is provided a system for changing the refractive power of an eye, the system having: a laser for providing a therapeutic laser beam; an optical path for delivery of the therapeutic laser beam from the laser to a natural crystal lens of an eye; optics located along the optical path, the optics providing the capability to direct the laser beam in at least the x and y directions; a laser beam delivery pattern, for directing the optics to deliver the laser beam in the laser beam delivery pattern to an predetermined area of the lens of the eye; the laser beam delivery pattern defining an axial excluded zone and an equatorial excluded zone; and, whereby, the delivery of the laser beam in the laser beam pattern to the natural crystalline lens of the eye changes the refractive power of the lens of the eye.

There is further provided a system for increasing the accommodative amplitude of an eye, the system having: a laser for providing a laser beam; an optical path for delivery of the laser beam from the laser to a natural crystal lens of an eye; optics located along the optical path, the optics providing the capability to control the laser beam in the x, y and z directions; a laser beam delivery pattern, for directing the optics to deliver the laser beam in the laser beam delivery pattern to a predetermined area of the lens of the eye; and, the laser beam delivery pattern having a plurality of laser beam shots, the plurality of laser beam shots defining a first and a second area of the lens, the first area having an outer portion that essentially follows the curvature of the lens, the second area defining an excluded zone; whereby, the delivery of the laser beam in the laser beam pattern to the natural crystalline lens of the eye changes the flexibility and shape of the first area of the lens, thereby increasing the accommodative amplitude of the eye.

Yet additionally, there is provided a system for increasing the accommodative amplitude of an eye, the system having: a laser for providing a therapeutic laser beam; a therapeutic laser beam delivery pattern, for directing an optics assembly to deliver the laser beam in the laser beam delivery pattern to an area of the natural crystalline lens of the eye; and, the therapeutic laser beam delivery pattern having a plurality of laser beam shots, the plurality of therapeutic laser beam shots defining a first and a second area of the lens, the first area having an anterior outer portion that essentially follows the anterior curvature of the natural crystalline lens and a posterior outer portion that essentially follows the posterior curvature of the natural crystalline lens; the second area defining an excluded zone; and, the excluded zone having an axial excluded zone and an equatorial excluded zone, the axial excluded zone and the equatorial excluded zone including the fetal nucleus of the natural crystalline lens; whereby, the delivery of the therapeutic laser beam in the therapeutic laser beam pattern to the natural crystalline lens of the eye changes the flexibility and shape of the first area of the lens, does not change the flexibility and shape of the second area of the lens, thereby increasing the accommodative amplitude of the eye.

Moreover there is provided a system for increasing the accommodative amplitude of an eye, the system having: a laser for providing a therapeutic laser beam; a therapeutic laser beam delivery pattern, for directing an optics assembly to deliver the therapeutic laser beam in the therapeutic laser beam delivery pattern to an area of the lens of the eye; and, the therapeutic laser beam delivery pattern having a plurality of therapeutic laser beam shots, the plurality of therapeutic laser beam shots defining a first and a second area of the lens, the first area having an anterior outer portion that essentially follows the anterior curvature of the lens and a posterior outer portion that essentially follows the posterior curvature of the lens; the second area defining an excluded zone; and, the excluded zone having an axial excluded zone and an equatorial excluded zone, the axial excluded zone and the equatorial excluded zone including the fetal nucleus of the lens; whereby, the delivery of the therapeutic laser beam in the therapeutic laser beam pattern to the natural crystalline lens of the eye changes the index of refraction of the first area of the lens, does not change the index of refraction of the second area of the lens, and increases the accommodative amplitude of the eye.

Still additionally, there is provided a system for increasing the accommodative amplitude of an eye, the system having: a laser for providing a laser beam; an optical path for delivery of the laser beam from the laser to a natural crystal lens of an eye; optics located along the optical path, the optics providing the capability to control the laser beam in the x and y directions; a laser beam delivery pattern, for directing the optics to deliver the laser beam in the laser beam delivery pattern to a predetermined area of the lens of the eye; and, the laser beam delivery pattern having a plurality of laser beam shots, the plurality of laser beam shots defining a first and a second area of the lens, the first area having an outer portion that essentially follows the curvature of the lens, the second area defining an excluded zone; whereby, the delivery of the laser beam in the laser beam pattern to the natural crystalline lens of the eye changes the flexibility of and weakens the first area of the lens, thereby increasing the accommodative amplitude of the eye.

Yet further there is provide a system for increasing the accommodative amplitude of an eye, the system having: a laser for providing a therapeutic laser beam; a laser beam delivery pattern, for directing an optics assembly to deliver the laser beam in the laser beam delivery pattern to an area of the lens of the eye; and, the laser beam delivery pattern having a plurality of laser beam shots, the plurality of laser beam shots defining a first and a second area of the lens, the first area having an anterior outer portion that essentially follows the anterior curvature of the lens and a posterior outer portion that essentially follows the posterior curvature of the lens; the second area defining an excluded zone; and, the excluded zone having an axial excluded zone and an equatorial excluded zone, the axial excluded zone and the equatorial excluded zone including the fetal nucleus of the lens; whereby, the delivery of the laser beam in the laser beam pattern to the natural crystalline lens of the eye changes the flexibility of and weakens the first area of the lens, does not change the flexibility and does not weaken the second area of the lens, thereby increasing the accommodative amplitude of the eye.

Moreover, there is provide a method of changing the refractive power of an eye, the method having: delivering a therapeutic laser beam, along an optical from a laser to a natural crystal lens of an eye; optics located along the optical path, directing the laser beam in at least the x and y directions and directing the laser beam in a laser beam delivery pattern to an predetermined area of the lens of the eye; the laser beam delivery pattern defining an axial excluded zone and an equatorial excluded zone; and, thereby changing the refractive power of the lens of the eye.

In addition there is provide a method for increasing the accommodative amplitude of an eye, the method having: directing a therapeutic laser beam on the natural crystalline lens of the eye in a delivery pattern having a plurality of therapeutic laser beam shots, the plurality of therapeutic laser beam shots defining a first and a second area of the natural crystalline lens, the first area having an anterior outer portion that essentially follows the anterior curvature of the lens; the second area defining an excluded zone; the excluded zone having an axial excluded zone and an equatorial excluded zone, the axial excluded zone and the equatorial excluded zone including the fetal nucleus of the natural crystalline lens; and thereby, changing the flexibility and shape of the first area of the natural crystalline lens, and not changing the flexibility and shape of the second area of the natural crystalline lens, thereby increasing the accommodative amplitude of the eye.

There is further provided these methods and systems in which one or more of the following may be present or practiced: wherein the first area has an inner diameter of 2 mm and an outer diameter of about 6 mm; wherein the excluded zone has an axial excluded zone and an equatorial excluded zone; wherein the excluded zone has an axial excluded zone and an equatorial excluded zone; wherein the axial excluded zone defines a cylinder having a central axis, the cylinder central axis being essentially parallel to an axis of the eye; wherein the axial excluded zone has a diameter of about 1 mm; wherein the axial excluded zone has a maximum diameter of about 3 mm; wherein the cylinder has a diameter of about 1 mm; wherein the axial excluded zone and the equatorial excluded zones intersect; wherein the intersection includes the area defined by the middle of the equatorial axis and the AP axis of the lens; wherein the excluded zone comprise substantially compressed lens material; wherein the excluded zone includes the embryonic nucleus; wherein the excluded zone includes the fetal nucleus; wherein the excluded zone is free from laser shots; wherein the excluded zone is free from laser shots; and wherein the delivery of the laser beam in the laser beam pattern to the natural crystalline lens of the eye does not change the flexibility and shape of the second area of the lens.

There is still further provided these methods and systems in which one or more of the following may be present or practiced: having a position determination assembly, where in the position determination assembly has: a light source to provide an illumination beam; an x, y, scanner; a z-focus device, an image capture device for providing observed data, a processor associated with the image capture device and capable of performing calculations, whereby the image capture device provides the observed data to the processor; the processor associated with a numerical model; and the processor capable of determining a position for a structure of the lens of the eye based upon the numerical model and the observed data; wherein the light source is a coherent light source; wherein the light source is a structured coherent light source; wherein the light source is a structured coherent light source having a short coherence length; wherein the light source is a laser diode; wherein the light source is an infrared laser diode; wherein the light source is a scanned infrared laser diode, whereby the scanned infrared laser diode defines a structured light source; wherein the image capture device has a Scheimpflug camera; wherein the axial excluded zone defines a cylinder having a central axis, the cylinder central axis being essentially parallel to an axis of the eye; wherein the axial excluded zone has a diameter of about 1 mm; wherein the axial excluded zone has a maximum diameter of greater than about 1.5 mm; where in the axial excluded zone has a maximum diameter of from about 2 mm to about 4 mm; wherein the cylinder has a diameter of about 2 mm to about 4 mm; wherein the axial excluded zone and the equatorial excluded zones intersect; wherein the intersection includes the area defined by the middle of the equatorial axis and the AP axis of the lens; wherein the intersection includes the fetal nucleus; and where in the position of the lens is determined using a structured coherent illumination light source having a short coherence length.

Yet moreover, there is provided these methods and systems in which one or more of the following may be present or practiced: wherein the axial excluded zone defines a cylinder having a central axis, the cylinder central axis being essentially parallel to an axis of the eye; wherein the axial excluded zone has a diameter of about 1 mm wherein the axial excluded zone has a maximum diameter of greater than about 1.5 mm; where in the axial excluded zone has a maximum diameter of from about 2 mm to about 4 mm; wherein the equatorial excluded zone defines a ring having an outer diameter of about 9 mm; wherein the equatorial excluded zone defines a disc having an outer diameter of about 9 mm; wherein the equatorial excluded zone defines a disc having an outer diameter equal to the equator of the lens; wherein the equatorial excluded zone defines a disc having an outer diameter of about 6 mm; wherein the axial excluded zone extends from the anterior lens capsule to the posterior lens capsule; wherein the axial excluded zone is free from laser shots; wherein the equatorial excluded zone is free from laser shots; wherein both exclude zones are free from laser shots; wherein the delivery of the laser beam in the laser beam pattern to the natural crystalline lens of the eye results in the shaped volumetric removal of lens material outside of the excluded zones; and, wherein the delivery of the laser beam in the laser beam pattern to the natural crystalline lens of the eye results in the selective flexibility and shape changes of lens material outside of the excluded zones.

BRIEF DESCRIPTION OF THE DRAWINGS

FIGS. 4A, 4B, 4C, 4D and 4E are diagrams representing elevation views of the geometry used for the development of laser shot patterns based upon the structure of the fetal nucleus (three suture branch nucleus) as it is rotated from the posterior view 4A through and to the anterior view 4E.

DESCRIPTION OF THE PREFERRED EMBODIMENTS

In general, embodiments of the present inventions provide systems and methods for increasing the amplitude of accommodation and/or changing the refractive power of a natural crystalline lens.

In general, embodiments of the present inventions further relate to methods and systems for determining the shape and position of the natural human crystalline lens and cornea relative to a laser device so as to provide an enhanced method and system for applying a laser to the lens and cornea. Embodiments of the present invention additionally relate to systems and methods that provide predetermined, precise and reproducible laser shot patterns for delivering laser shot patterns having a predetermined and precise shape that is reproducible from patient to patient and surgeon to surgeon.

Figure 2:
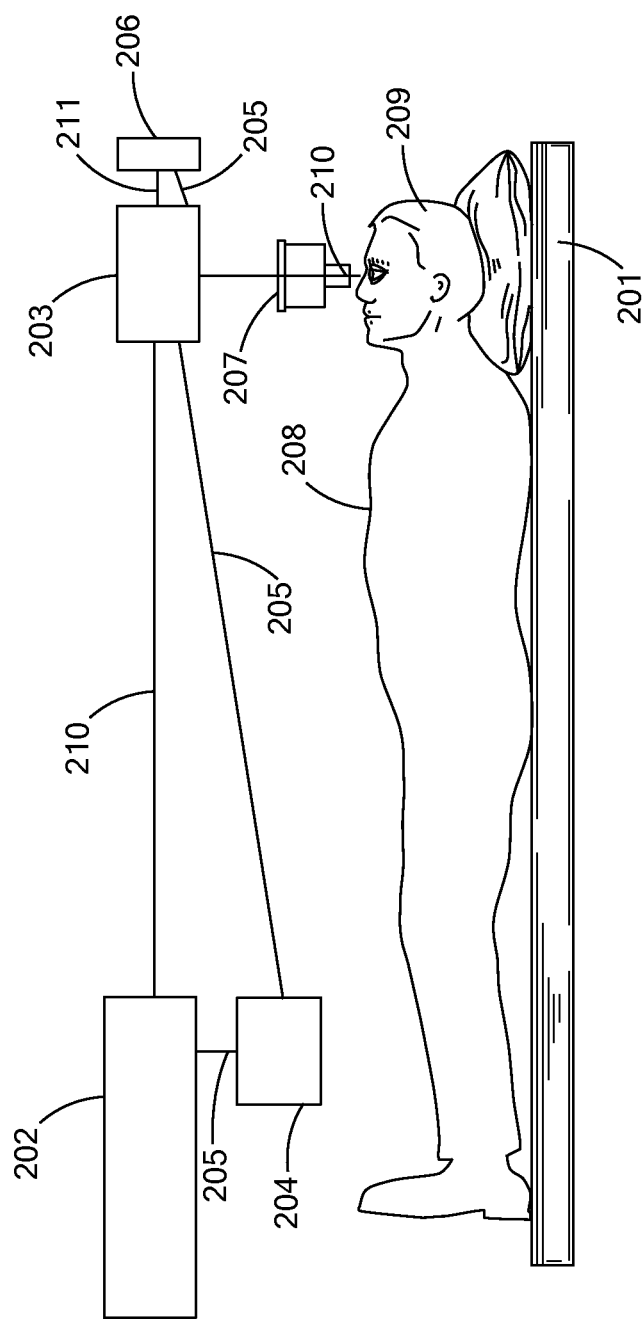
FIG. 2 is a block schematic diagram of a type of system for delivering a laser beam shot pattern to the lens of an eye according to the teachings of the present invention.

As generally shown in the embodiment of FIG. 2 there is provided a system for delivering a laser beam shot pattern to the lens of an eye comprising: a patient support 201; a laser 202; optics for delivering the laser beam 203; a control system for delivering the laser beam to the lens in a particular pattern 204, which control system 204 is associated with and/or interfaces with the other components of the system as represented by lines 205; a means for determining the position of lens with respect to the laser 206, which means 206 receives an image 211 of the lens of the eye; and a laser patient interface 207.

The patient support 201 positions the patent's body 208 and head 209 to interface with the optics for delivering the laser beam 203.

In general, the laser 202 should provide a beam 210 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers would include: the Delmar Photonics Inc. Trestles-20, which is a Titanium Sapphire (Ti:Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) µjewel D series D-400-HR, which is a Yb:fiber oscillator/amplifier having a wavelength of 1045 nm, less than a 1 picosecond pulse width, about 5 MHz PRF, with 100 nanojoules; the Lumera Staccato, which is a Nd:YVO4 having a wavelength of 1064 nm, about 10 picosecond pulse width, about 100 KHz PRF, with 100 microjoules; and, the Lumera Rapid, which is a ND:YVO4 having a wavelength of 1064 nm, about 10 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains. and, the IMRA FCPA (fiber chirped pulse amplification) pJewel D series D-400-NC, which is a Yb:fiber oscillator/amplifier having a wavelength of 1045 nm, less than a 100 picosecond pulse width, about 200 KHz PRF, with 4 microjoules. Thus, these and other similar lasers may be used a therapeutic lasers.

In general, the optics for delivering the laser beam 203 to the natural lens of the eye should be capable of providing a series of shots to the natural lens in a precise and predetermined pattern in the x, y and z dimension. The optics should also provide a predetermined beam spot size to cause photodisruption with the laser energy reaching the natural lens. Thus, the optics may include, without limitation: an x y scanner; a z focusing device; and, focusing optics. The focusing optics may be conventional focusing optics, and/or flat field optics and/or telecentric optics, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the AGRES Rhino Scanner. Examples of such z focusing devices would be the Phsyik International Peizo focus unit Model ESee Z focus control and the SCANLAB varrioSCAN.

In general, the control system for delivering the laser beam 204 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system as well as maintaining data, obtaining data and performing calculations. Thus, the control system may contain the programs that direct the laser through one or more laser shot patterns.

In general, the means for determining the position of the lens with respect to the laser 206 should be capable of determining the relative distance with respect to the laser and portions of the lens, which distance is maintained constant by the patient interface 207. Thus, this component will provide the ability to determine the position of the lens with respect to the scanning coordinates in all three dimensions. This may be accomplished by several methods and apparatus. For example, x y centration of the lens may be accomplished by observing the lens through a co-boresighed camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor and/or the Aculux Laser Ranger LR2-22. The use of a 3-dimensional viewing and measurement apparatus may also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera, which can view a reference and the natural lens, and would also include a light source to illuminate the natural lens. Such light source could be a structured light source, such as for example a slit illumination designed to generate 3-dimensional information based upon geometry.

A further component of the system is the laser patient interface 207. This interface should provide that the x, y, z position between the natural lens and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that is fixed against the outer surface of the eye and is then positioned against the laser optical housing, thus fixing the distance between the laser, the eye and the natural lens. Reference marks for the 3-dimensional viewing and measuring apparatus may also be placed on this applanator. Moreover, the interface between the lower surface of the applanator and the cornea may be observable and such observation may function as a reference. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics and/or some structure that is of known distance from the laser along the path of the laser beam and fixed with respect to the laser. Further examples of such devices are generally disclosed in U.S. Pat. Nos. D462442, D462443, and D459807S, the disclosures of which are hereby incorporated by reference.

It is preferred that the interface may be a corneal shaped transparent element whereby the cornea is put into direct contact with the interface or contains an interface fluid between. Examples of preferred types of patient interfaces and patient interface devices are disclosed and taught in US Patent Application Publication Nos. 2010/0022994 and in U.S. Patent Application Ser. No. 61/228,533 filed Jul. 24, 2009, Ser. No. 61/228,457 filed Jul. 24, 2009, Ser. No. 61/299,536 filed Jan. 29, 2010, and Ser. No. 61/300,167 filed Feb. 1, 2010, the entire disclosures of each of which is incorporated herein by reference.

Figure 2A:
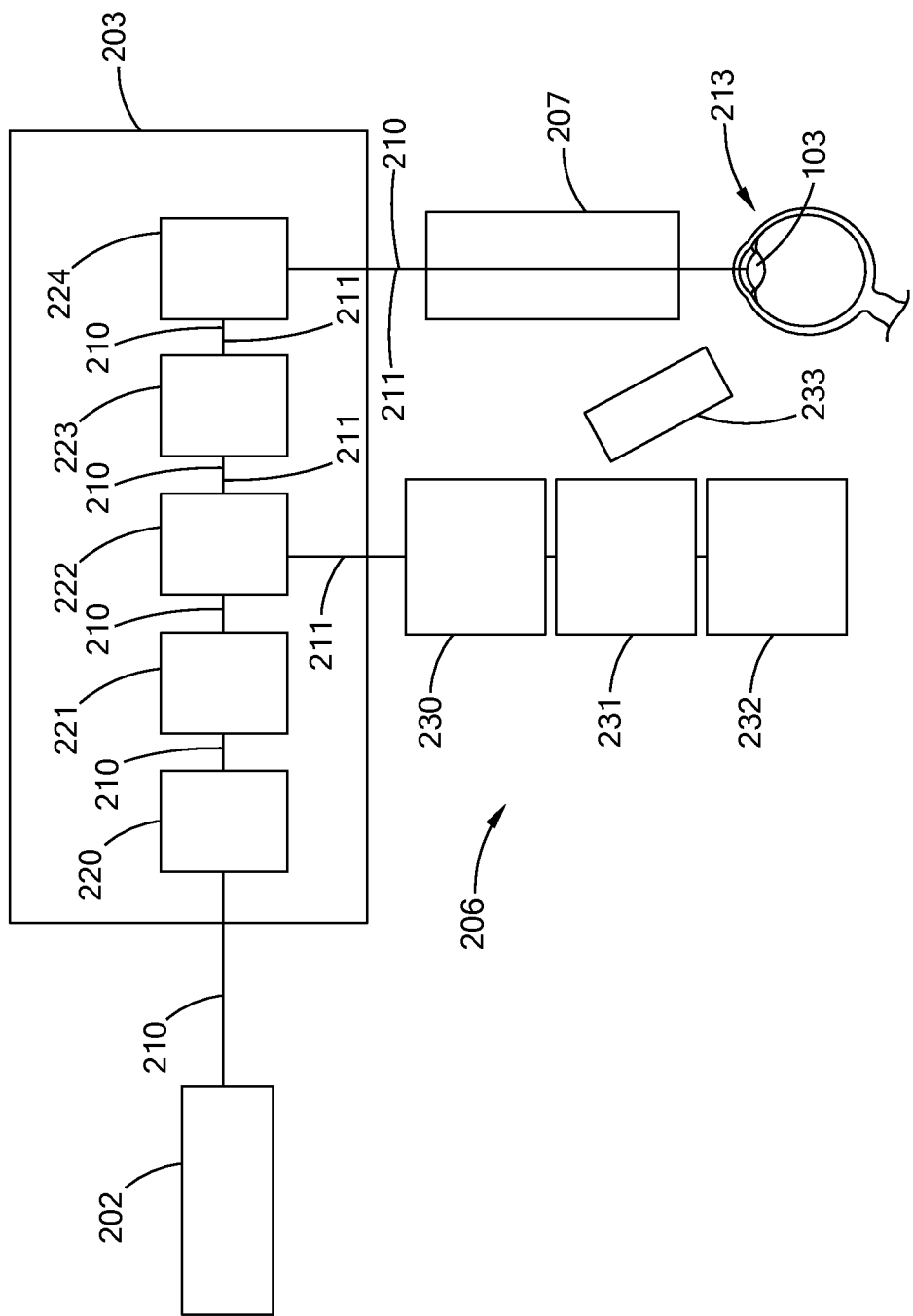
FIG. 2A is a block schematic diagram of illustrative components forming a portion of a system for delivering a laser beam shot pattern to the lens of an eye according to the teachings of the present invention.

An illustrative combination utilizing by way of example specific optics for delivering the laser beam 203 and means for determining the position of the lens 206, is shown in part, in FIG. 2A. FIG. 2A is a more detailed schematic diagram of a configuration of the system of FIG. 2. Thus, the example of FIG. 2A provides a laser 202, laser optics for delivering the laser beam 203, which optics comprise a beam expander telescope 220, a z focus mechanism 221, a beam combiner 222, an x y scanner 223, and focusing optics 224. There is further provided in FIG. 2A relay optics 230, camera optics 231, which may also include a zoom, and a ccd camera 232, which components form a part of a three-dimensional viewing and measuring apparatus. Moreover, these components 231 and 232 in combination with a light source 233, and the scanner 223 are the means for determining the position of the lens 206.

This combination of FIG. 2A utilizes the x y scanner 223 to create stereoscopic images of the lens with only a single ccd camera 232. Optical images 211 of the eye 213 and in particular optical images of the natural lens 103 of the eye 213 are conveyed along a path 211. This path 211 follows the same path as the laser beam 210 from the natural lens 103 through the laser patient interface 207, the focusing optics 224, the x y scanner 223 and the beam combiner 222. This combination of FIG. 2A further comprises: a laser patient interface 207, and a light source 233, which could be for example uniform illumination, or a slit illumination or other structured light source designed to enhance 3-dimensional accuracy. The light source, in part, provides illumination of the natural lens of the patient's eye for the purposes of determining the 3-dimensional position of the lens. Thus, either stereoscopic images and/or the information from the camera are sent to a controller and/or computer (not shown in FIG. 2A) for further processing and use in determining 3-dimensional positions of the lens. Stereo images may be generated by commanding the scanner to go to and pause at a nominal left position and then electronically trigger the camera and controller to capture and store the left image; then command the scanner/camera/controller similarly to capture and store a right image. This sequence may be repeated in a periodic manner. These left and right images can be processed by the controller to generate the position and shape of the lens. The left and right images can be displayed using a stereo video monitor. Camera images or stereo images may also be used to measure suture geometry and orientation in the patients lens, which can be used to determine the parameters of suture based shot patterns and to align suture based shot patterns to the patients lens suture geometry and orientation. The combination illustrated in FIG. 2A provides 3-dimensional information that can be used to determine the shape of the lens, including the anterior and posterior surfaces thereof. This information can also be used to visualize the structure of the lens, including sutures. Moreover, the information about the lens obtained from the combination of FIG. 2A can further be used in determining the laser shot pattern and laser shot placement with respect to lens shape and/or structure.

FIGS. 2 and 2A-2F are block schematic diagrams and thus the relative positions and spacing of the components illustrated therein are by way of example. Accordingly, the relative placements of these components with respect to one another may be varied and all or some of their functions and components may be combined.

FIGS. 2B-2E are further more detailed embodiments of a portion of the system of FIG. 2. To the extent that like numbers are used in these Figures and in FIGS. 2 and 2A they have the same meaning. Thus, FIGS. 2B-2E provide further examples and combinations of optics for delivering the laser beam 203 and means for determining the position of the lens 206.

Figure 2B:
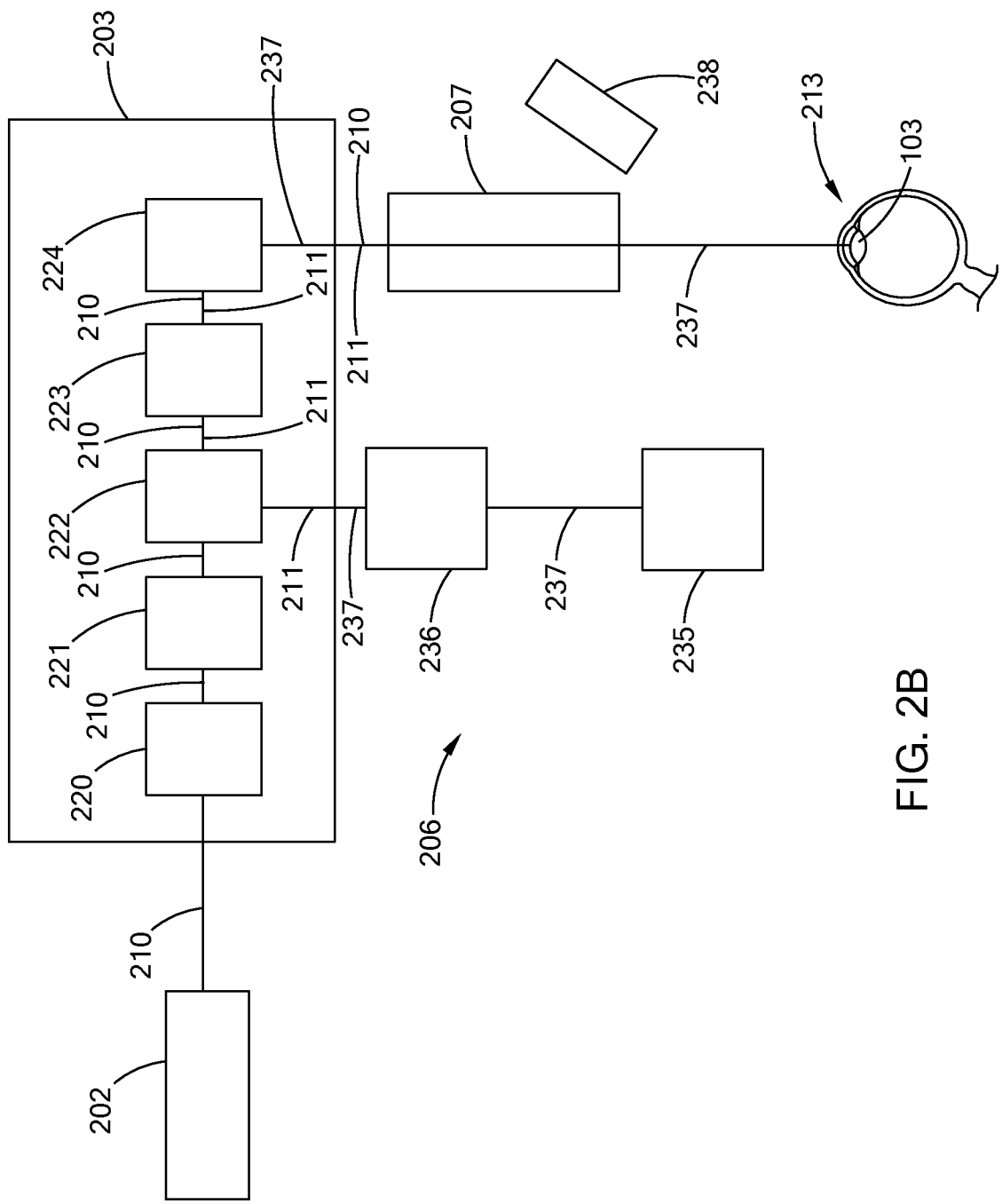
FIG. 2B is a block schematic diagram of illustrative components forming a portion of a system for delivering a laser beam shot pattern to the lens of an eye according to the teachings of the present invention.

FIG. 2B is a block schematic diagram of a portion of a system having a means for determining the position of the lens 206, which employs a scanned laser illumination source. Thus, there is provided a laser illumination source 235, a beam expander and focusing optics 236, an illumination laser path 237 and a camera 238 for viewing the lens 103 as illuminated by the laser illumination source. Component 235 in combination with the scanner 223 and camera 238 are the means for detecting the position of the lens 206.

The laser illumination source 235 can be any visible or near infrared laser diode, preferably with a short coherence length for reduced speckle. For example, the laser can be a Schafter+Kirchhoff Laser (90CM-M60-780-5-Y03-C-6) or can also be obtained from StockerYale and may also come with focusing optics. In operation, x y scanner 223 scans the beam from the illumination laser 235 into the focusing optics 224, through the patient interface 207 and onto the lens 103. Thus, the beam from the illumination laser 235 follows the illumination laser path 237. The beam expander focusing optics 236 combined with focusing optics 224 provide a high F number, slow focusing beam with long depth of field. The depth of field is approximately equal to the path length of the laser illumination beam through the lens 103. Thus, producing small and approximately equal sized spots at the anterior and posterior of lens 103. The illumination laser beam is scanned, predominately in one axis, in a line at a rate sufficiently fast compared to the camera 238 exposure time such that the scanned illumination laser beam acts like a slit illumination source during the exposure time. On subsequent exposures or frames of the camera 238, the illumination laser beam is scanned to different positions, thus, illuminating the entire lens over time. This can occur as a series of y scanned lines with different x positions exposures or the lines can be radially scanned with each exposure at a different angle. From the analysis of the data from all of these images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2C:
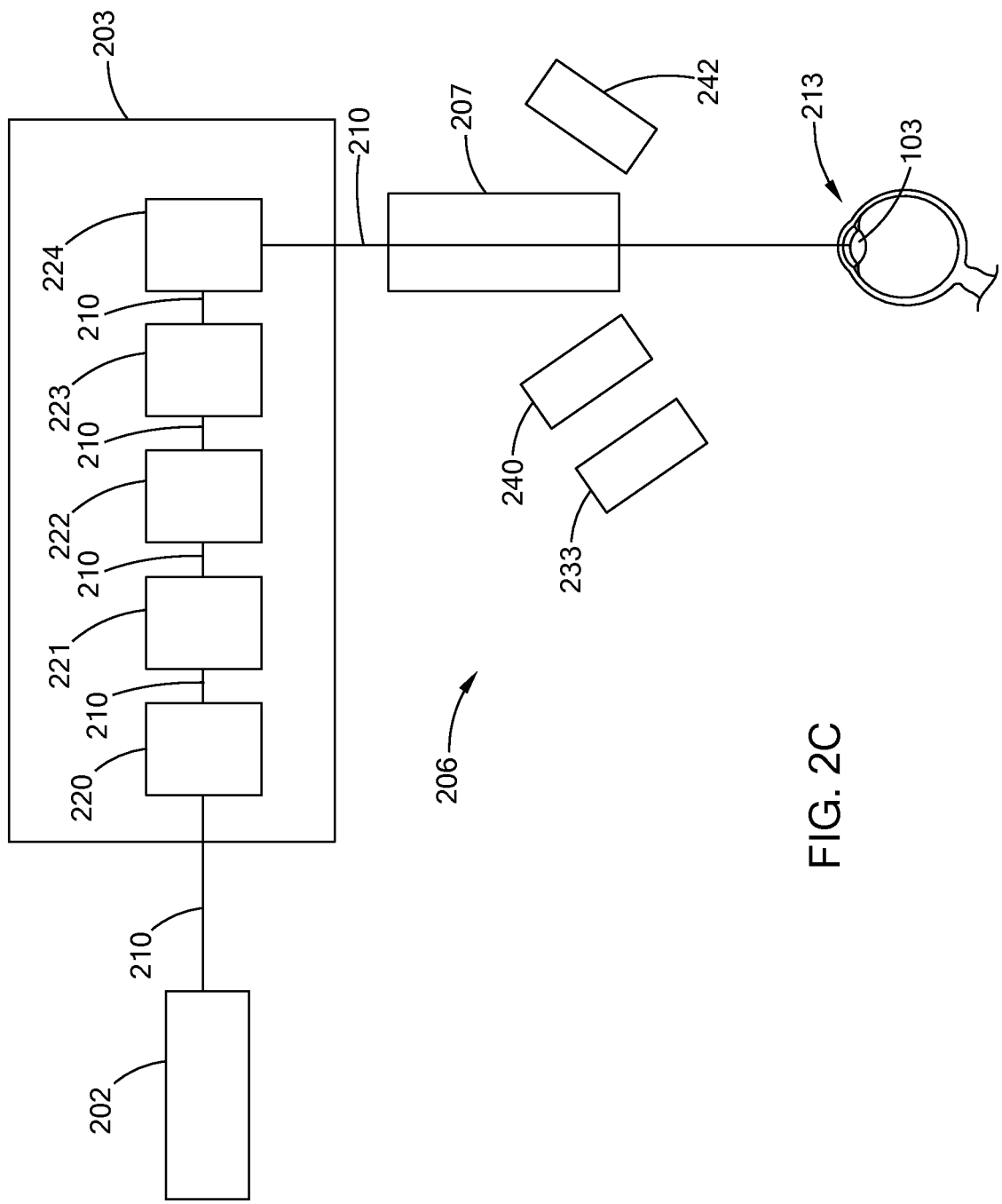
FIG. 2C is a block schematic diagram of illustrative components forming a portion of a system for delivering a laser beam shot pattern to the lens of an eye according to the teachings of the present invention.

FIG. 2C is a block schematic diagram of a portion of a system having a means for detecting the position of the lens 206, which employs dual cameras. Thus, there is provided a left camera 241 and a right camera 242. Components 241, 242 and 233 are the means for detecting the position of the lens 206.

The system of FIG. 2C utilizes two camera stereo viewing technology for providing patient care capability and for obtaining images and data for determining lens position and/or shape. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2D:
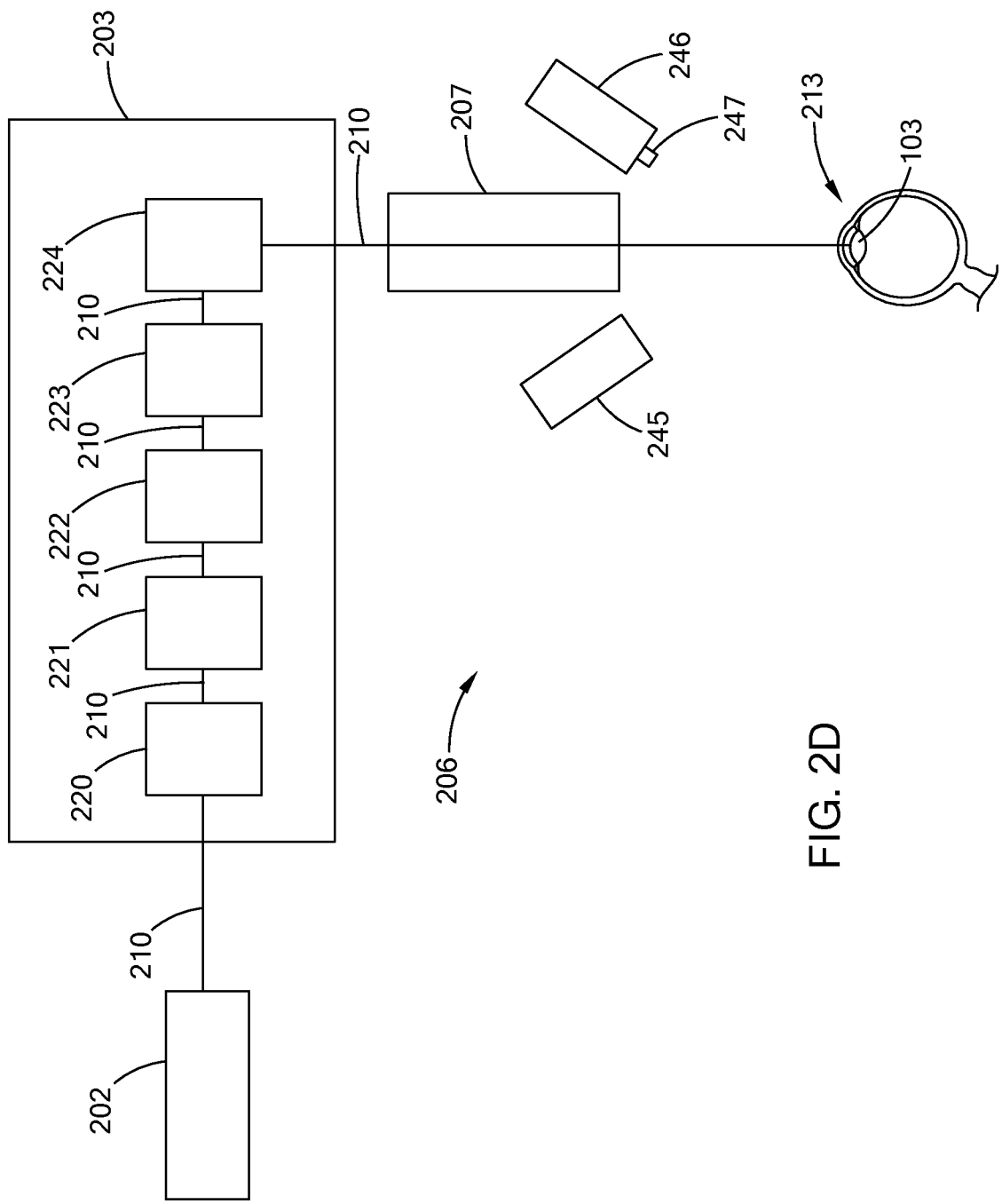
FIG. 2D is a block schematic diagram of illustrative components forming a portion of a system for delivering a laser beam shot pattern to the lens of an eye according to the teachings of the present invention.

FIG. 2D is a block schematic diagram of a portion of a system having a means for detecting the position of the lens 206, which employs structured illumination. Thus, there is provided a structured light source 245 and a camera 246, having a lens 247, for viewing the structured light source. Components 245 and 246 in combination are a means for detecting the position of the lens 206.

The system of FIG. 2D utilizes a structured light source and a camera to provide patient care capability and for obtaining images and data for determining lens position and/or shape. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2E:
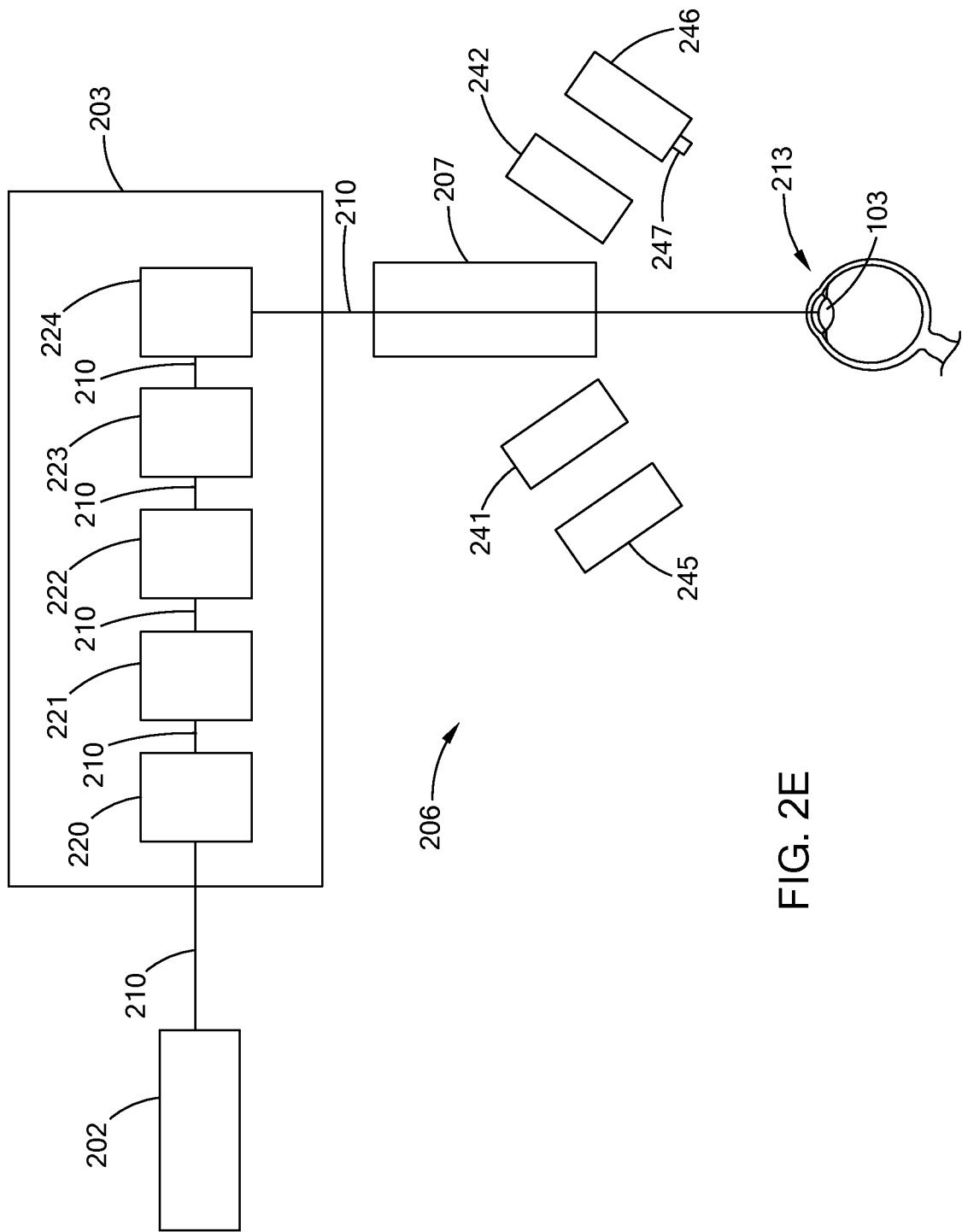
FIG. 2E is a block schematic diagram of illustrative components forming a portion of a system for delivering a laser beam shot pattern to the lens of an eye according to the teachings of the present invention.

FIG. 2E is a block schematic diagram of a portion of a system having a means for detecting the position of the lens 206, which employs structured illumination and dual cameras. Thus, there is provided a structured light source 245, a camera 246 for viewing the structured light source, a lens 247 for camera 246, a left camera 241 and a right camera 242. Components 245 and 246, in combination are the means for detecting the position of the lens 206. Components 241 and 242, in combination are a means for providing patient care, including monitoring capability. This combination 241, 242 may also provide information and/or data to determine the position of the lens.

The combination of components in the system illustrated in FIG. 2E provides the ability to optimize the accuracy of determining the position of the lens, while also providing the ability to separately and/or independently optimize patient care. Patient care includes, but is not limited to, visualization of the eye and its surrounding area, procedures such as attaching a suction ring, applying ophthalmic drops, utilizing instruments, and positioning the patient for surgery. In one embodiment the structured light source 245 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501-660-20-5. In this embodiment the structured illumination source 245 also includes scanning means. Another embodiment of the structured light source 245, may be a stationary grid pattern projected on the lens. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

When using a scanned slit illumination the operation includes positioning the slit on one side of the lens, taking an image then moving the slit approximately one slit width, then taking another image, and then repeating this sequence until the entire lens is observed. For example, a 100 µm slit width can scan a nominal 9 mm dilated pupil diameter in 90 images, which takes approximately 3 seconds using a 30 Hz frame rate camera. To obtain images of the anterior and posterior surface in a single image without overlap, the slit should be at an angle to the AP axis, i.e., it should not be parallel to that axis. The nominal slit angle can be approximately 15 to 30 degrees from the AP axis. Any visible or near IR wavelength source within the sensitivity of the camera may be used. Low coherence length sources are preferable to reduce speckle noise.

Another embodiment for the structured light illumination sub-system shown in FIG. 2E is to arrange the structured light illumination source 245, the structured light camera 246 and the lens for the structured light camera 247 in the so-called Scheimpflug configuration which is well-known. In Summary, the Scheimpflug condition states that given an object, a lens and an image, that the object plane is imaged sharply in the image plane if the object plane, the lens plane and the image plane intersect in the same line. The structured light source 245 projects a line and or a plurality of lines onto the eye lens 103 at an angle or plurality of angles. The light scattered at the eye lens 103 forms the object to be imaged by the lens 247 and focused onto the camera system 246. Since the slit illuminated image in the eye lens 103 may be at a large angle with respect to the camera lens 247 and camera 246, this presents a large depth of field to the camera and the entire slit image may not be in sharp focus at the camera. By tilting the camera lens and the camera at an angle or plurality of angles such that Scheimpflug's condition is met, the image along the illuminated plane can be in sharp focus. Alternately, the camera and/or lens may be tilted such that the angle between the slit illuminated image plane and the camera focal plane is reduced, improving the depth-of-focus sharpness, however may not meet the Scheimpflug condition. Such configurations can improve sharpness further by reducing the aperture of the optical path, thereby increasing the F# of the system. These angles will depend on the angle the slit beam makes with the eye. This will increase the depth of field at the object, the scattered light from the slit illuminator, and allow it to imaged through the lens onto the camera image plane and remain in focus for the entire depth of the object.

There is further provided the use of a structured light illuminating and receiving system, such as for example slit illumination, which in addition to measuring the position and shape of anterior and posterior lens surfaces in three dimensions, can be used as a screening tool for determining a candidate patient's suitability for laser lens surgery. Thus, light from a structured light system is directed toward the subject lens. The amplitude of the received scattered light distributed throughout the lens is then evaluated to detect scattering regions that are above threshold, which is a level of scattering that would interfere with the laser surgery. Thus, the detection of lens scattering malformations that could interfere with, or reduce the efficacy of a procedure can be detected and evaluated. Such scattering malformations of the lens would include, without limitation, cataractous, pre-cataractous and non-cataractous tissue. Such scattering malformations, may be located throughout the lens, or may be restricted to specific regions of the lens. For example the systems of FIGS. 2A-2E in cooperation with a controller and/or processor may function as such a structured light illuminating and receiving system.

The structured light illuminating and receiving system may be contained within the surgical laser system or it may be a separate unit for evaluating the suitability of a candidate patient for laser lens surgery. Commercially available examples of such structured light illuminating and receiving systems are the Ziemer Ophthalmic Systems GALILEI Dual Scheimpflug Analyzer and the Oculus, Inc. PENTACAM. It is believed that these systems cannot be used to determine the position of the lens with respect to the treatment laser. However, lens shape data from these systems may be obtained and then used in conjunction with position data provided by systems such as the systems of FIGS. 2A-2E.

Figure 2F:
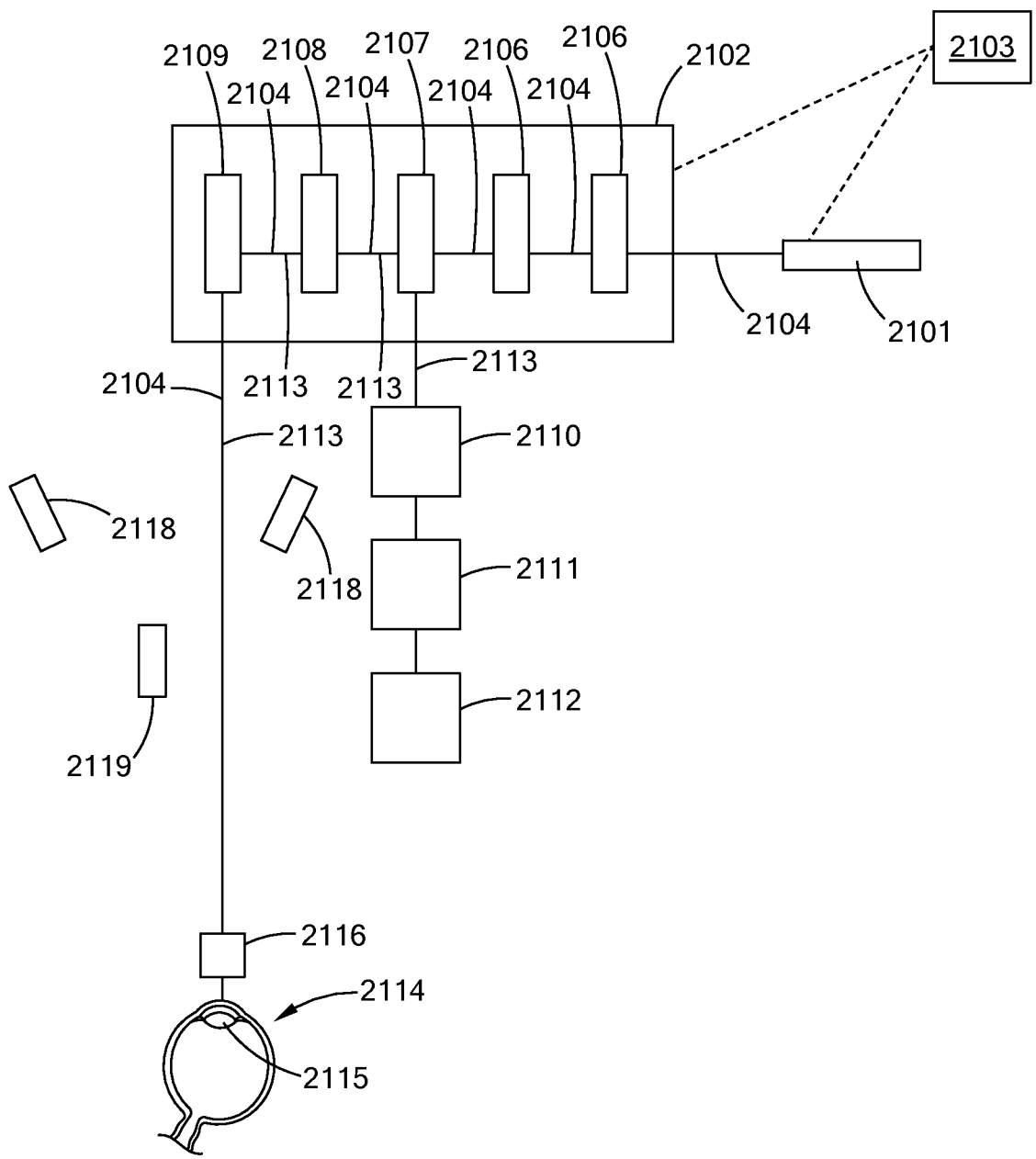
FIG. 2F is a schematic diagram of a type of system for delivering a laser beam shot pattern to the lens of an eye.

Thus, in general, a laser system, e.g., a laser device, for treating patients is provided as shown by way of example in FIG. 2F. In this system there is provided a treatment laser 2101; optics for delivering the laser beam 2102; a control system for delivering the laser beam to the lens in a particular pattern 2103, which control system 2103 is associated with and/or interfaces with the other components of the system, as shown for example by dashed lines in FIG. 2F, and/or other control systems not shown in FIG. 2F.

In general, the treatment laser 2101 should provide a beam 2104 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 nm to 2000 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in 2007/084694 A2 and WO 2007/084627A2, which are incorporated herein by reference. These and other similar lasers may be used as therapeutic lasers.

By way of example, for a given optical spot size, the amount of energy required to exceed photodisruption threshold might be 5 µJ. Rather then providing a single pulse of 20 µJ to a spot in a shot pattern, a burst of 4, 5 µJ pulses could be utilized, with each pulse in the burst being separated by about 20 nanoseconds. The use of such a burst will tend to increase the probability of achieving photodisruption threshold while also minimizing the Rayleigh range effects of extending the tissue effect in the z direction, or along the beam path. In this way the use of such bursts increase the probability of achieving photodisruption, which has also been referred to as Laser Induced Optical Breakdown (LIOB).

Accordingly, it is desirable to use energy densities in the region around LIOB threshold, i.e., the threshold at which photodisruption takes place, to minimize Rayleigh range effects. However, in the vicinity of LIOB threshold small and sometimes random variations in transmission, absorption, laser energy fluctuations, or optical spot size variations due to for example optical aberrations, can prevent LIOB in an undesirable and random matter throughout the treatment field. Optical spot size variations due to for example optical aberrations are especially found in low F/# systems.

It is further desirable in some examples to have complete treatment in any given treatment field. Thus, for example, in the shot patterns provided herein the treatment filed would be all of the x y and z coordinates of the pattern. It is further, for particular applications and in particular horizontal cuts, desirable to have laser energy densities in the vicinity of LIOB. Such energy densities minimize Rayleigh range effects and thus minimize the amount of material in the z direction that is removed. However, by using such energy densities, and thus, obtaining the benefit of minimized Rayleigh range effects, the undesirable and random prevention of LIOB, as discussed above in the preceding paragraph, can occur. Thus, to minimize Rayleigh range effect and avoid LIOB prevention, it is provided in an embodiment to use of a burst of closely spaced in time pulses, wherein each pulse within the burst is in the vicinity of LIOB threshold. Through the use of such bursts the probability of achieving LIOB threshold is increased compared to using a single pulse with the same energy density.

In general, the optics for delivering 2102 the laser beam 2104 to the natural lens of the eye should be capable of providing a series of shots to the natural lens in a precise and predetermined pattern in the x, y and z dimension. The optics should also provide a predetermined beam spot size to cause photodisruption by the laser pulses delivered to the lens or cornea.

In general, the control system 2103 for delivering the laser beam 2104 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the slit scanned laser 2117 and camera 2118 and/or from a separate controller for the slit scanned laser system or camera.

The laser optics for delivering 2102 the laser beam 2104 comprise a beam expander telescope 2105, a z focus mechanism 2106, a beam combiner 2107, an x y scanner 2108, and focusing optics 2109. There is further provided relay optics 2110, camera optics 2111, which include a zoom, and a first ccd camera 2112.

Optical images 2113 of the eye 2114 and in particular optical images of the natural lens 2115 of the eye 2114 are conveyed along a path 2113. This path 2113 follows the same path as the laser beam 2104 from the natural lens 2115 through the laser patient interface 2116, the focusing optics 2109, the x y scanner 2108 and the beam combiner 2107. There is further provided a laser patient interface 116, and a structured light source 117 and a structured light camera 118, including a lens.

A structured light source 2117 may be a slit illumination having focusing and structured light projection optics, such as a Schafter+Kirchhoff Laser Macro Line Generator Model 13LTM+9CM, (Type 13LTM-250S-41+90CM-M60-780-5-Y03-C-6) or a StockerYale Model SNF-501L-660-20-5, which is also referred to as a slit scanned laser. In this embodiment the structured illumination source 117 also includes slit scanning means 2119.

When using a scanned slit illumination the operation includes positioning the slit at an acute angle to the crystalline lens' AP axis and to one side of the lens, taking an image then maintaining the same angle, moving the slit a predetermined distance, then taking another image, and then repeating this sequence until the entire lens is observed through the series of slit sections. The nominal slit angle can be approximately 15 to 30 degrees from the AP axis. Any visible or near IR wavelength source compatible with the camera may be used. Low coherence length sources are preferable to reduce speckle noise.

The structured light illumination source 2117 and the structured light camera 2118 are arranged in an angled relationship. The angled relationship may be but is not required to be in the so-called Scheimpflug configuration, which is well-known. The structured light source 2117, in conjunction with the slit scanning means 2119, projects a line and or a plurality of lines onto the eye lens 2115 at an angle or plurality of angles. The light scattered at the eye lens 2115 forms the object to be imaged by the lens 2247 and focused onto the camera system 2118. Since the slit illuminated image in the eye lens 2115 may be at a large angle with respect to the camera 2118, this presents a large depth of field to the camera and the entire slit image may not be in sharp focus at the camera. By tilting the camera at an angle or plurality of angles the image along the illuminated plane can be in sharper focus. To the extent that a shaper focus is not obtained, arithmetic data evaluation means are further provided herein to determine a more precise location of the illuminated structures with respect to the laser device.

The images from the camera 2118 may be conveyed to the controller 2103 for processing and further use in the operation of the system. They may also be sent to a separate processor and/or controller, which in turn communicates with the controller 2103. The structured light source 2117, the camera 2118 and the slit scanning means 2119 comprise a means for determining the position, shape and apex of the lens and cornea in relation to the laser system. Alternate means of measuring the position, shape and apex of the lens and cornea may be used in lieu of the specific embodiment described herein. Other equivalent biometric methods for measuring the lens and cornea include rotating Scheimpflug configurations such are used in the commercial PENTACAM OCULUS device, optical coherence tomography (OCT) and B-scan ultrasound technologies.

In general, embodiments of the present invention provides for the delivery of the laser beam in patterns that utilize, or are based at least in part on, lens geometry, curvature of the lens and/or the position and location of the lens and cornea with respect to various apparatus. More specifically, embodiments of the invention could utilize measurements of the radii or curvature, center of curvature and apex of the lens and cornea to control the position and orientation of the capsulotomy and the position and shape of the envelope of cuts in the lens nucleus used to fragment the lens for removal. As part of embodiments of the present invention the concept of matching and/or compensating for the curvature and position of the capsule of the lens is provided. Anterior and posterior lens curvatures and lens location measurements can be used in the context of Kuszak aged lens models, Burd's eye model, Burd et al. Vision Research 42 (2002) 2235-2251, or on specific lens measurements to determine the position of the capsulotomy and shape of the envelope defining the boundary of cuts within the lens fibrous mass. Thus, in general, these laser delivery patterns are based in whole and/or in part on the mathematical modeling and actual observation data regarding the shape of the lens, the position of the lens and/or the geometry of the lens.

A further embodiment of the present systems and methods is to define a high accuracy position measurement of the anterior capsule, so as to provide in general greater accuracy, precisions and reproducibility from patient to patient for the delivery of the laser beam and beam patterns. Thus, there is provided a method applying slit technology with new and innovative methods to determine the apex of the lens of the eye, with respect to the therapeutic laser device, and thus, providing accurate measurements and relative position determinations for performing procedures on the lens of the eye.

Figure 2G:
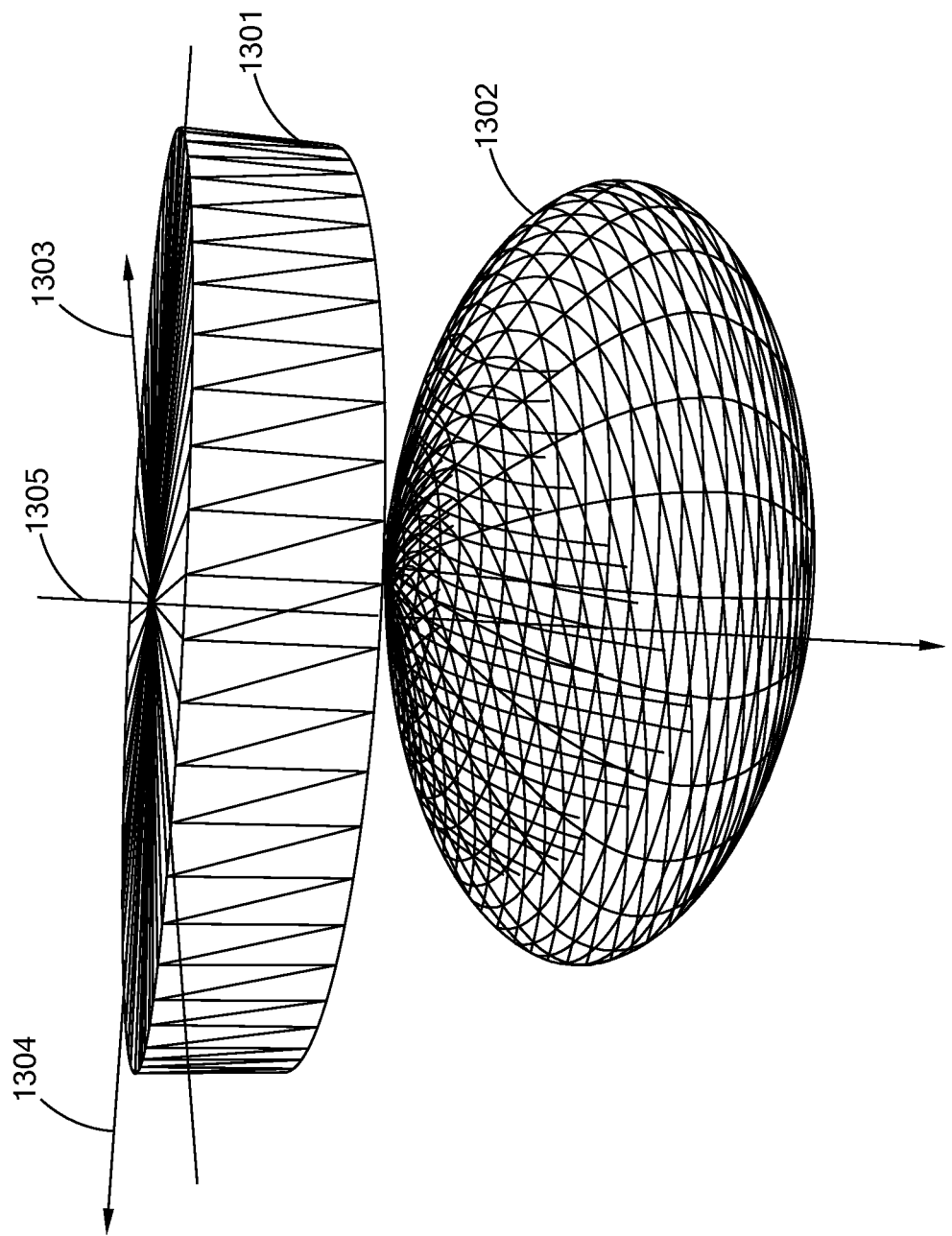
FIGS. 2G-2N are diagrams illustrating the paths of slit scanned light with respect to the lens of the eye.

Thus, turning to FIGS. 2G to 2N there is provided a series of drawings showing the use of the laser structured light source 2117 (from the embodiment of FIG. 2F) projection onto the lens of a human eye through a glass plate. FIG. 2G shows the general configuration of the glass plate and lens. FIGS. 2H to 2N show the path of the light from the slit lamp to the glass plate and the lens and the return paths of light beams from the glass plate and the lens, as the location of the slit lamp's impingement on the glass plate and the lens is changed. Like components in FIGS. 2G to 2N have like numbers, thus, for example glass plate 1301, 1401, 1501, 1601 and 1701 are the same In FIG. 2G there is provided a glass plate 1301 positioned in relation to a human lens 1302 having an X axis 1303, a Y axis 1304 and a Z axis 1305. The glass plate 1301 has a thickness of 1.57 mm and an index of refraction of 1.57.

Figure 2H:
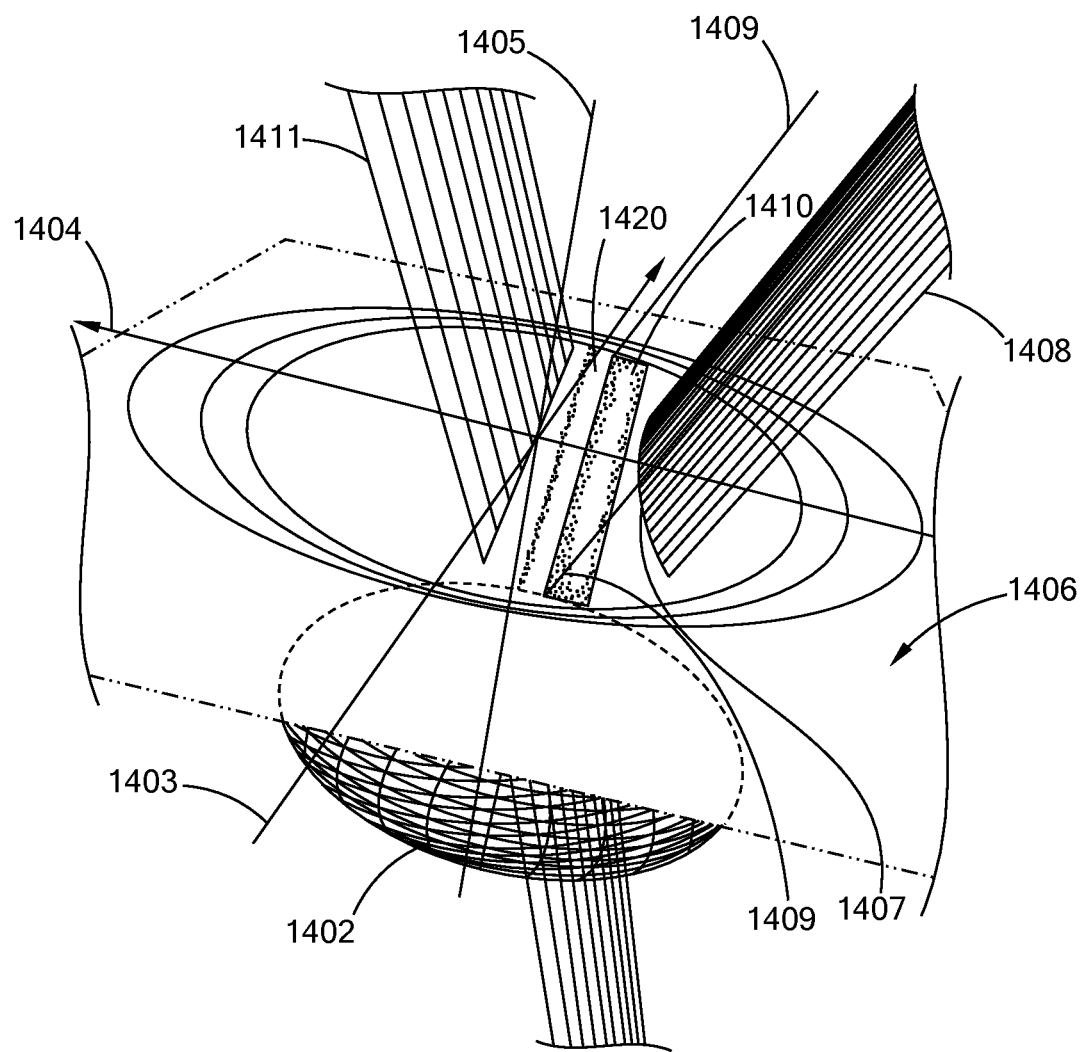
Figure 2I:
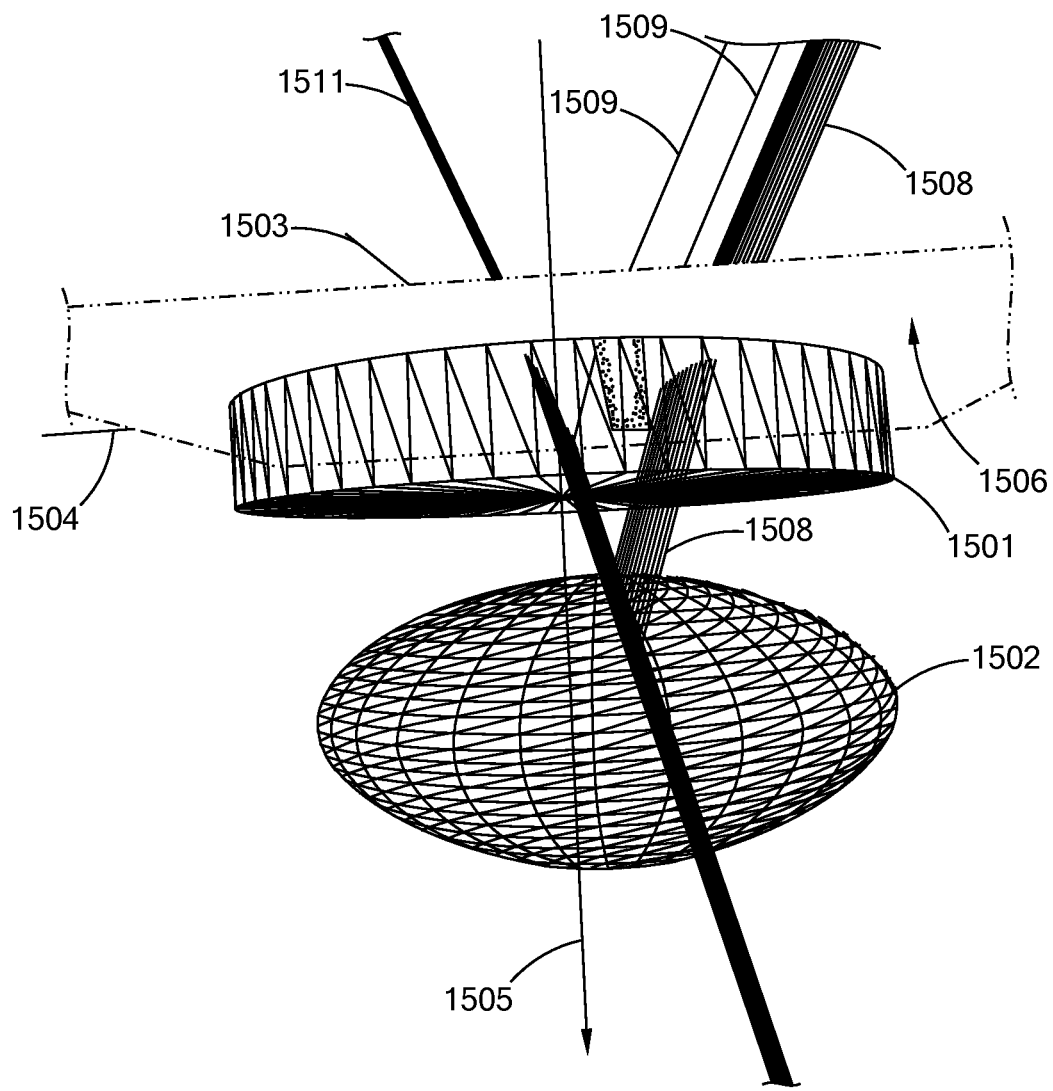

In FIG. 2H is a top view of the glass plate (not seen) and lens 1402 of FIG. 2G. In FIG. 2H there is provided an X axis 1403, a Y axis 1404, an XY plane 1406 and a Z axis 1405. In this figure light beams 1411 from a slit lamp are directed through the XY plane 1406 to the glass plate and lens 1402. The light travels back from the glass plate and lens 1402, providing an image of the glass plate 1420 and applanated cornea 1410, beams of light 1409 from the bottom of the glass plate (by bottom is it meant the side of the glass plate closest to the lens), beams of light 1408 from the anterior surface of the lens 1402, and a line 1407 based upon the beams 1408, which represents the curvature of the lens 1402 at the point where the light 1411 illuminates it. FIG. 2I is a view of the same system and light paths but from below the XY plane 1506. (Again like numbers correspond to like components, thus beam 1508 is the same as beam 1408).

Figure 2J:
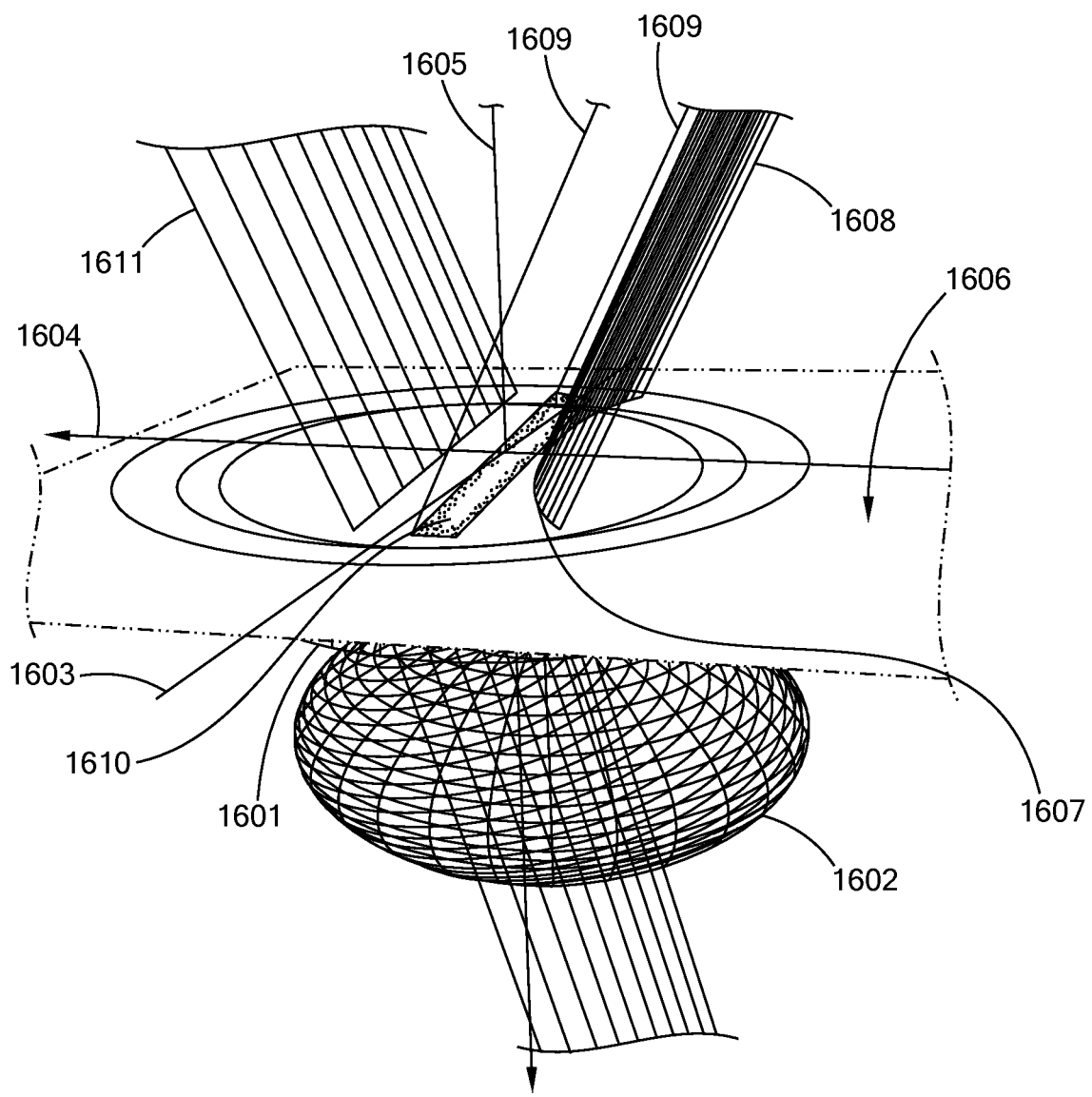

FIG. 2J is similar to FIG. 2H except that the point of illumination by the light beam 1611 on the glass 1601 and the lens 1602 has moved. Thus, by moving the point of illumination there is provided moved beams 1609 and 1608 and a curvature 1607 for a different portion of the lens.

Figure 2K:
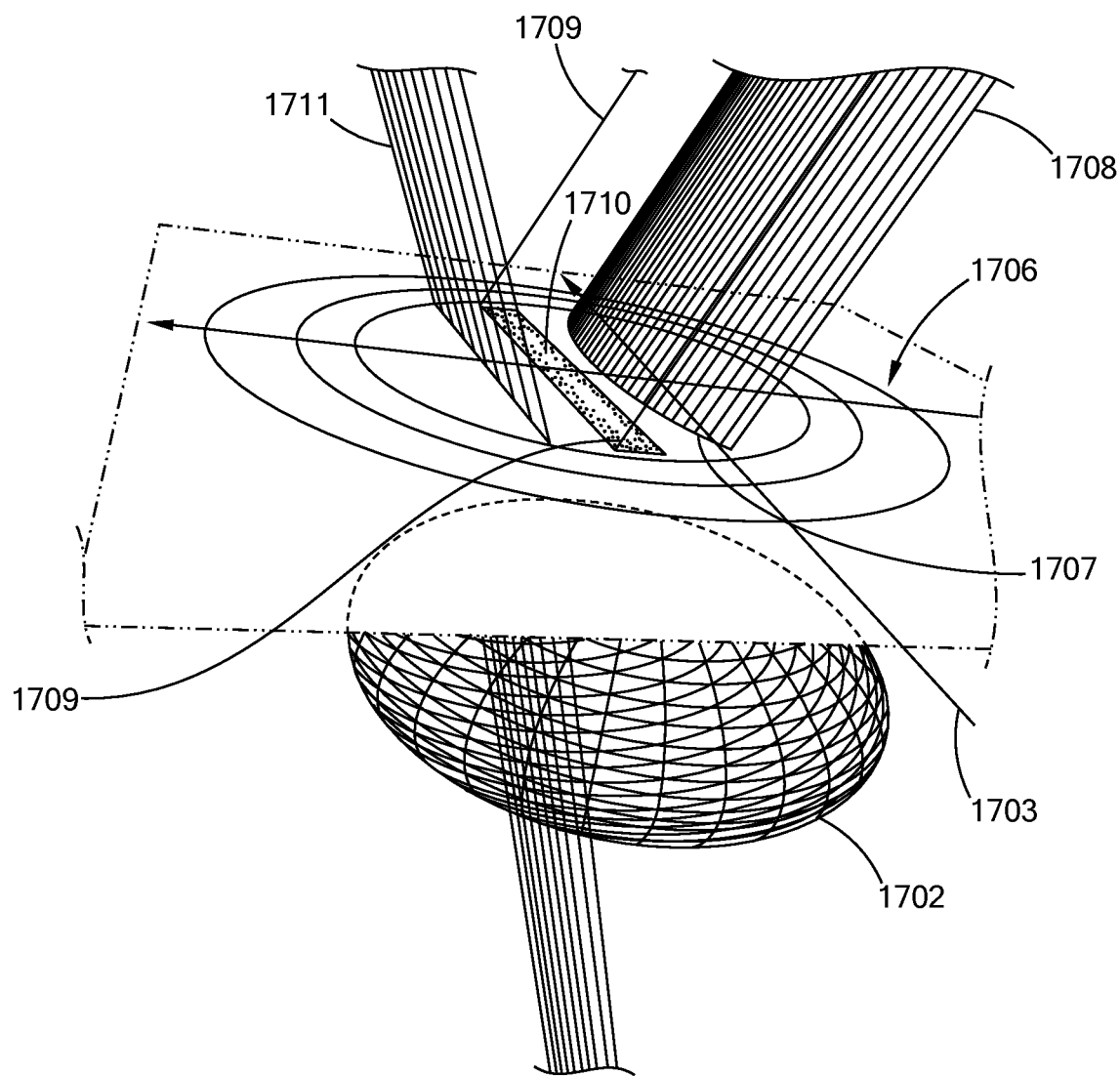

FIG. 2K is similar to FIGS. 2I and 2H, except that as with FIG. 2J the point of illumination of light beam 1711 has been moved.

Figure 2L:
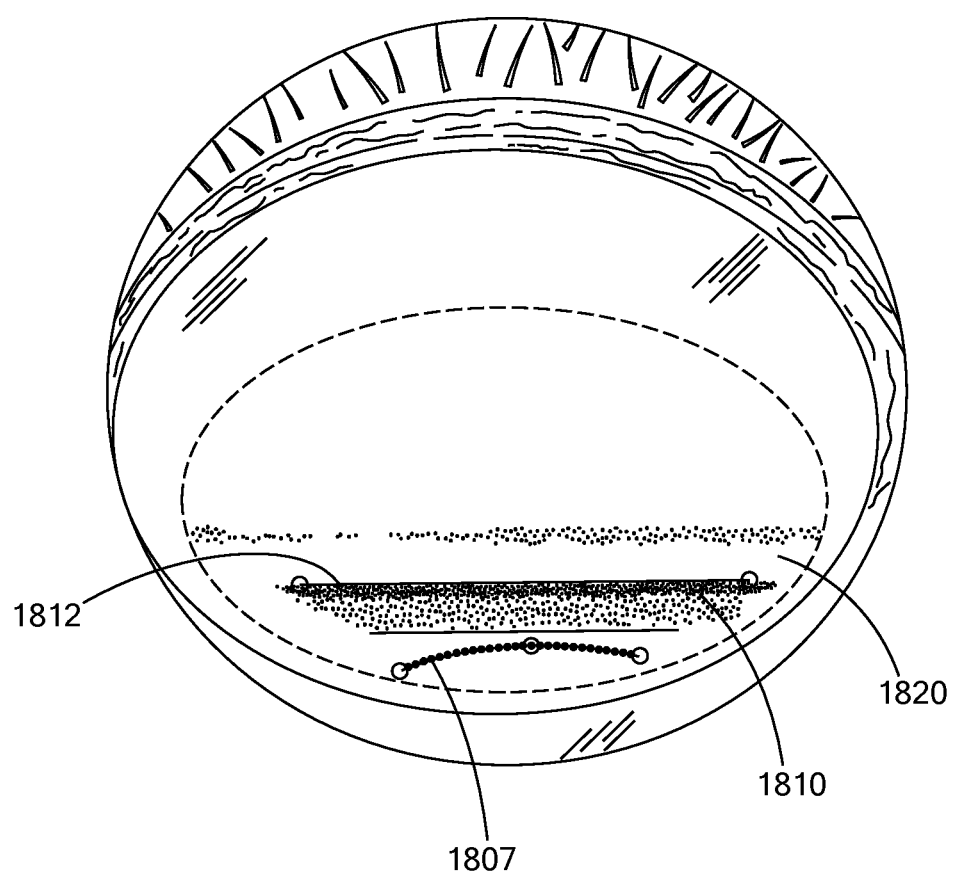

FIG. 2L is an image of the applanated cornea 1810 with the bottom surface of the glass plate 1820 being determined and labeled as line 1812. There is then provided a curvature of the lens 1807 for that particular portion of the lens that is being illuminated by the slit lamp. The determination of this curvature of the lens is based upon the application of a Random Sample Consensus ("RANSAC") algorithm to estimate with great certainty the parameters of a mathematical model from for the shape and position of the lens and in particular the lens capsule from a set of observed data, line beams such as for example 1408, 1508, 1608 & 1708. The monochrome camera images comprise an array of pixels representing light from the slit laser scattered from structures within the lens and cornea. The magnitude or brightness associated with each pixel in the image represents the amount of light scattered from a particular XYZ position within in the eye along the slit path. A highly scattering structure, such as the anterior lens capsule generates a bright arc of pixels in the image. However, viewed more closely, the image of the arc is granular and somewhat indistinct, containing some pixels which are bright and which should be definitely included in the determination of the curvature of the arc and some pixels which are of intermediate brightness which might or might not be included in the determination of the curvature. The estimation of the lens curvature involves selecting which pixels to include in the determination of curvature and then to estimate the curvature based on the selected pixels. These estimation can be done in two manners. In one manner the RANSAC algorithm is applied to all of the data obtained from the numerous camera images of slit lamp illuminations made at different slit positions and used simultaneously to determine a spherical shape. In another manner, which is presently preferred the RANSAC algorithm is applied to data from individual camera images of particular slit lamp positions and used to determine the shape and position of a circle from that each image. The circles, which were determined by RANSAC, are used to estimate the parameters of the best fit sphere representing the lens shape, using a least squares non-liner regression. The RANSAC algorithm was first published by Fischler and Bolles in 1981.

In general the RANSAC algorithm as employed herein is based upon a number of algorithm parameters that are chosen to keep the level of probability of convergence of the fit to the circle fit parameters reasonably high. The approach is iterative wherein each iteration is used to refine the selection of which pixels (inliers) are best used to determine the parameters of the fit circle and which should be excluded (outliers) and to, at the same time refine the best fit parameters based on the pixels selected in the latest iteration. Thus, a model was fitted to the initial hypothetical inliers, to make an initial estimate of the parameters of the fit circle, i.e. shape and position of the lens from observed data. Based on the initial parameter estimates, all other data points, pixels, are checked to see how far they fall from the fitted model and the set of inliers and outliers is adjusted. The model was then re-estimated from all adjusted inliers. The model is evaluated by estimating a parameter related to the total magnitude of error of the inliers relative to the model. This procedure was repeated, and the precision of the estimate is refined at each iteration.

An example of a RANSAC algorithm is as follows:

```
input:
    data - a set of observed data points
    model - a model that can be fitted to data points
    n - the minimum number of data values required to fit the model
    k - the maximum number of iterations allowed in the algorithm
    t - a threshold value for determining when a data point fits a model
    d - the number of close data values required to assert that a model fits
        well
to
data
output: best_model - model parameters which best fit the data (or nil if no
        good model is found)
    best_consensus_set - data point from which this model has been
        estimated
    best_error - the error of this model relative to the data points
iterations := 0
best_model := nil
best_consensus_set := nil
best_error := infinity
while iterations < k
    maybe_inliers := n randomly selected values from data
    maybe_model := model parameters fitted to maybe_inliers
    consensus_set := maybe_inliers
    for every point in data not in maybe_inliers
        if point fits maybe_model with an error smaller than t
            add point to consensus_set
    if the number of elements in consensus_set is > d
    if the number of elements in consensus_set is > d
            better_model := model parameters fitted to all points in
                consensus_set
            this_error := a measure of how well better_model fits
                these points
            if this_err < best_err
                best_model := better_model
                best_consensus_set := consensus_set
                best_error := this_error
    increment iterations
return best_model, best_consensus_set, best_error
```

The series of best fit parameters for circles estimated for different slit beam locations is then used in a least squares algorithm to determine the radius of curvature and center of curvature of the anterior capsule, assuming that a sphere is a good representation of the shape of the capsule in the central region of interest.

Thus, by photographing the light scattered by lens structures from a laser slit beam positioned sequentially to a series of different slit locations and applying a RANSAC algorithm and/or a RANSAC algorithm and a least squares non-liner regression with a sphere fit, to the data obtained from each of those series of illuminations, a detained image of the shape and position of the lens relative to the laser device can be obtained. In the current embodiment, the shape and position of the anterior lens capsule is characterized by the estimation of the radius and center of curvature. Using this information, the position of the apex of the lens relative to the laser device, and in particular the therapeutic laser, can be determined for use in positioning and orienting the capsulotomy. Though not shown here, an exactly analogous method as described above for the anterior lens capsule can be used to determine the center and radius curvature of the anterior cornea. Since the center of curvature of the lens and cornea are known in most cases to fall close to the visual axis of the eye, these two points define a line which intersects the anterior lens capsule at or near the visual axis and position of the intersection can be used to center the capsulotomy cut at or near the visual axis as is generally desired for best optical outcome.

Having both the shape, position and apex of the lens provides the ability to greatly increase the accuracy and reproducibility of the laser shots and laser patterns placement in the lens of the eye.

In embodiments of the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 µm size spot with an energy sufficient to cause photodisruption, a spacing of 20 µm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 µm spot size with a 10 µm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock wave propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 5 KHz to 1 MHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

Figure 2M:
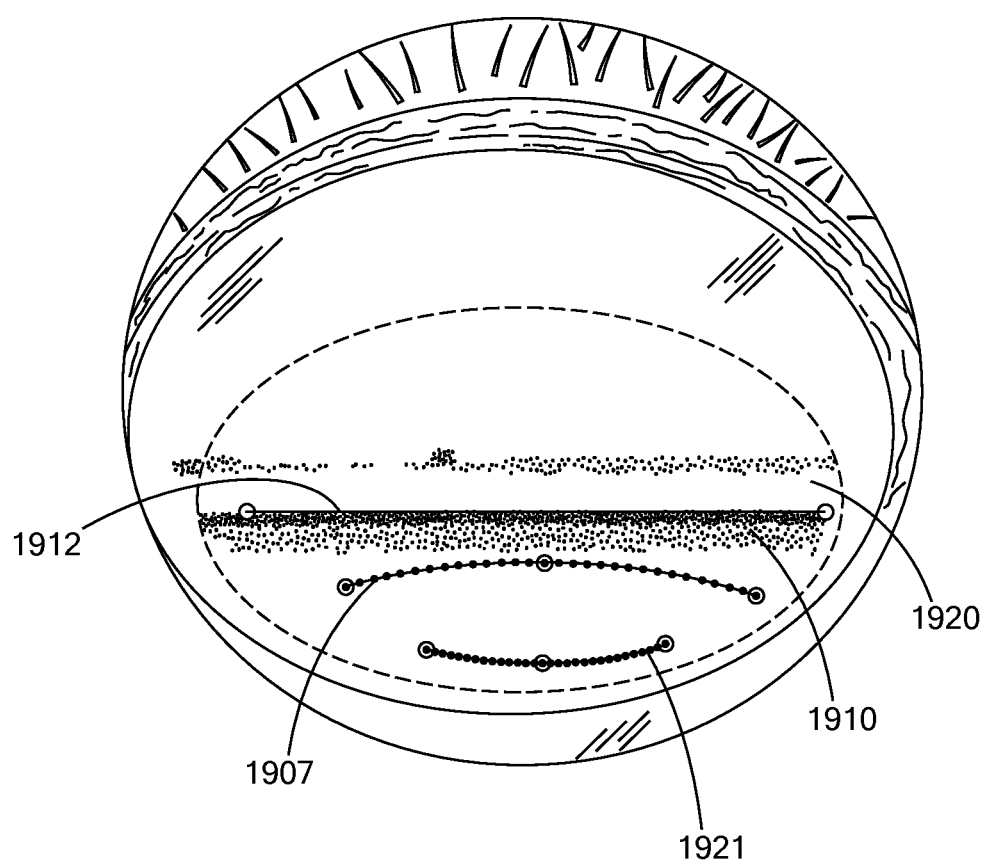

In FIG. 2M there is provided an image of a reference glass plate 1920, the posterior surface 1912 of the reference glass plate 1920 and the applinated cornea 1910. There is further provided the lens anterior capsule 1907 and the lens posterior capsule 1921.

Figure 2N:
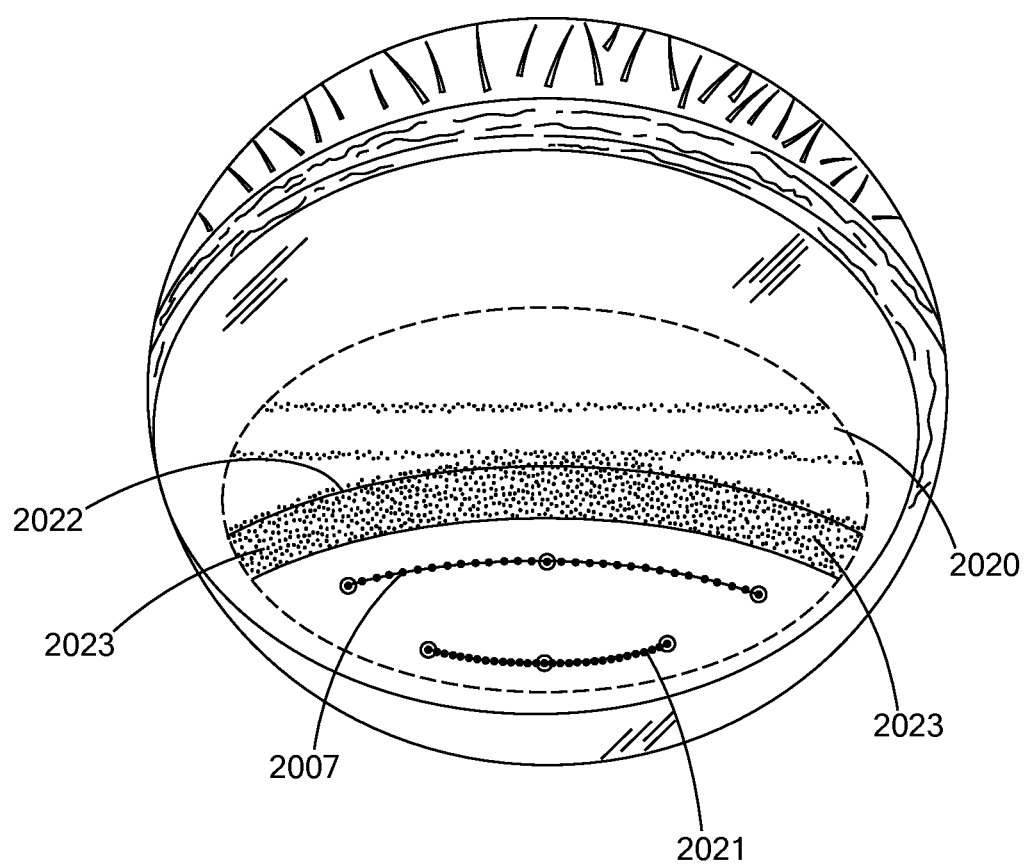

In FIG. 2N there is provided an image of a curved corneal interface 2022 and the un-applinated cornea 2023, as well as a reference glass 2020. There is further provided the lens anterior surface 2007 and the lens posterior surface 2021.

Thus, as show in FIGS. 2M and 2N, by way of example, embodiments of the present invention provides a novel means for determining the lens anterior and posterior capsule radii and centers of curvature.

Figure 1:
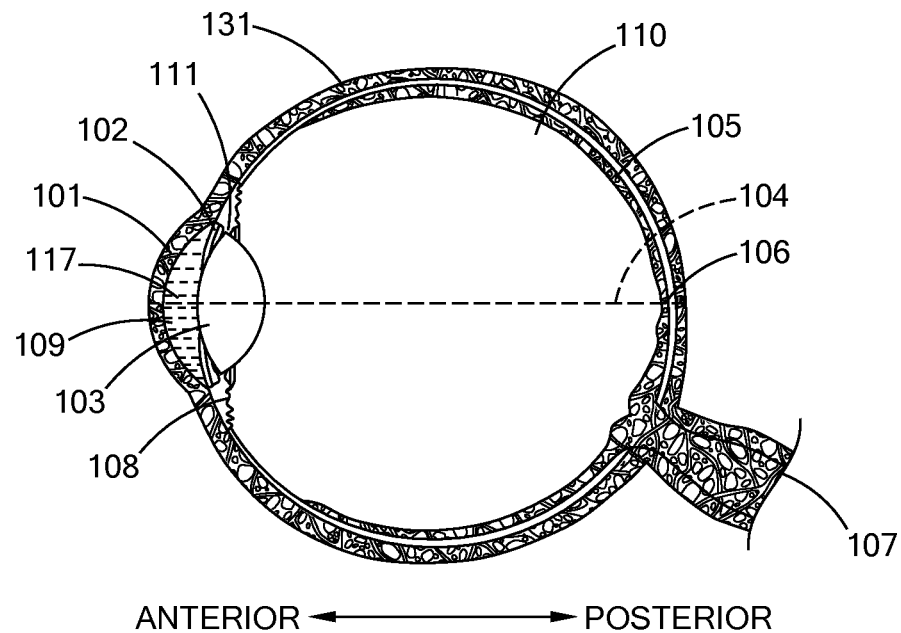
FIGS. 1 and 1A are cross sectional representations of the human eye.
Figure 1A:
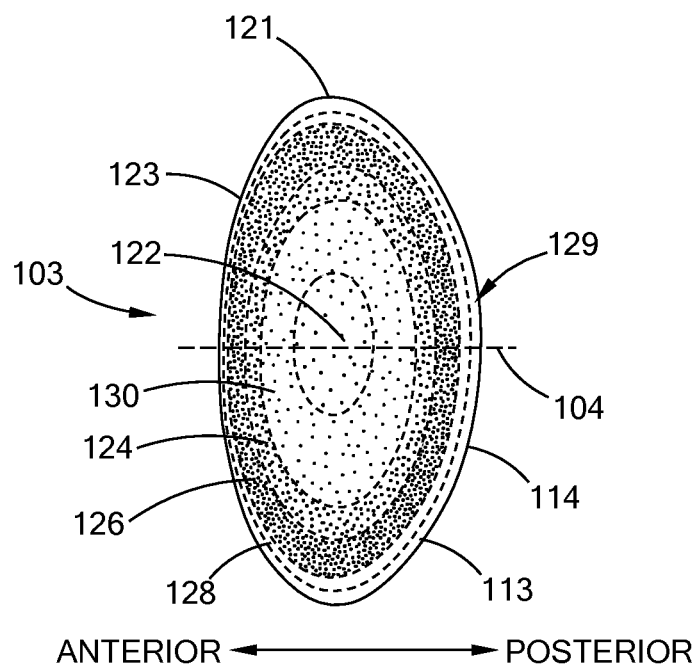

FIGS. 4 A-E illustrate the three branched or Y suture geometry in the context of the structures found in the fetal nucleus 415 of the lens. Thus, these figures provide a more detailed view of the structures illustrated as layer 130, which encompasses layer 122 of FIG. 1A. In FIGS. 4 A-E the view of the inner layer of the lens is rotated stepwise from the posterior side FIG. 4A to the anterior side FIG. 4E of the lens. Thus, this layer of the lens has three posterior suture lines 401, 402, and 403. This layer also has three anterior suture lines 412, 413 and 414. The anterior suture lines are longer than the posterior suture lines and these lines are staggered when viewed along the anterior to posterior (AP) axis 411. The lens fibers, which form the layers of the nucleus, are shown by lines 404, it being understood that these are only illustrative lines and that in the actual natural layer of the lens there would be many times more fibers present. To aid in illustrating the structure and geometry of this layer of the nucleus representative fibers 405, 406, 407, 408, 409 and 410 have been exaggerated and individually shaded in FIGS. 4 A-E. Thus, as the view of the lens nucleus is rotated from posterior to anterior the positions of these representative fibers, there relationship to each other, and there relationship to the suture lines is illustrated.

The length of the suture lines for the anterior side are approximately 75% of the equatorial radius of the layer or shell in which they are found. The length of the suture lines for the posterior side are approximately 85% of the length of the corresponding anterior sutures, i.e, 64% of the equatorial radius of that shell.

The term—essentially follows—as used herein would describe the relationship of the shapes of the outer surface of the lens and the fetal nucleus 415. The fetal nucleus is a biconvex shape. The anterior and posterior sides of the lens have different curvatures, with the anterior being flatter. These curvatures generally follow the curvature of the cortex and the outer layer and general shape of the lens. Thus, the lens can be viewed as a stratified structure consisting of long crescent fiber cells arranged end to end to form essentially concentric or nested shells.

As provided in greater detail in the following paragraphs and by way of the following examples, embodiments of the present invention utilizes this and the further addressed geometry, structure and positioning of the lens layers, fibers and suture lines to provide laser shot patterns for increasing the accommodative amplitude of the lens. Although not being bound by this theory, it is presently believed that it is the structure, positioning and geometry of the lens and lens fibers, in contrast to the material properties of the lens and lens fibers, that gives rise to loss of accommodative amplitude. Thus, these patterns are designed to alter and affect that structure, positioning and/or geometry to increase accommodative amplitude.

Figure 5A:
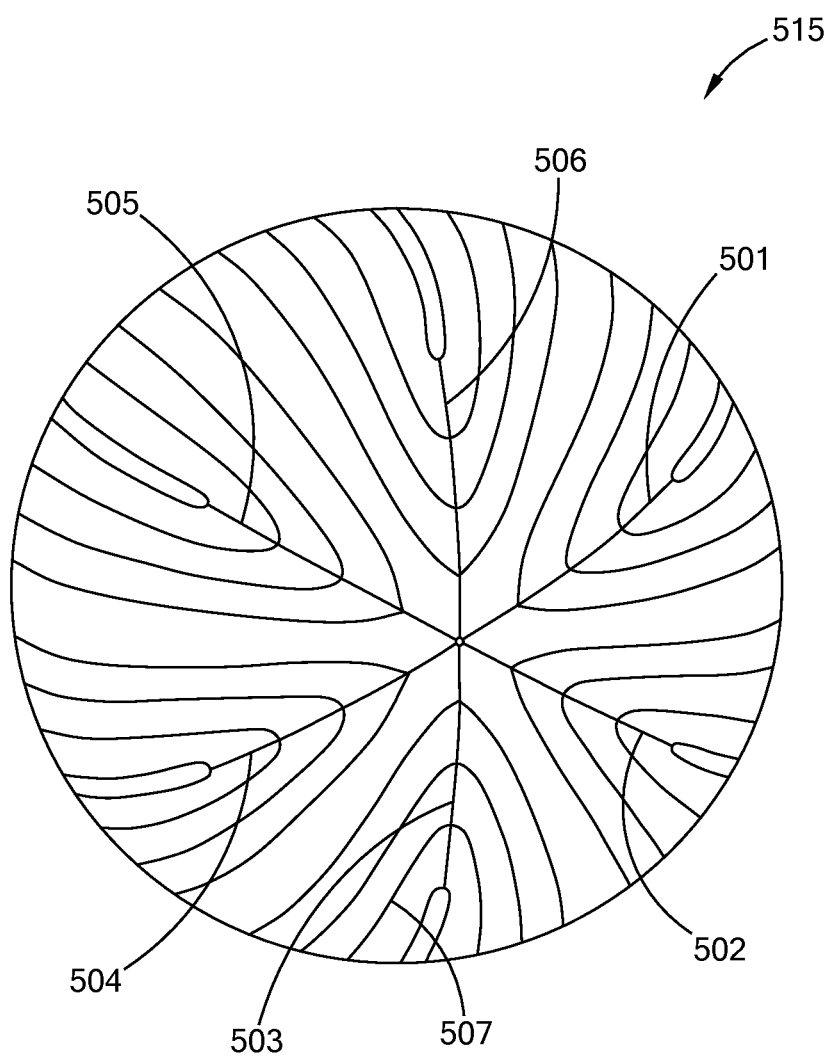
FIGS. 5A, 5B, and 5C are diagrams representing posterior, side and anterior elevation views, respectively, of the geometry used for the development of laser shot patterns based upon the structure of the infantile nucleus (six suture branch nucleus).
Figure 5B:
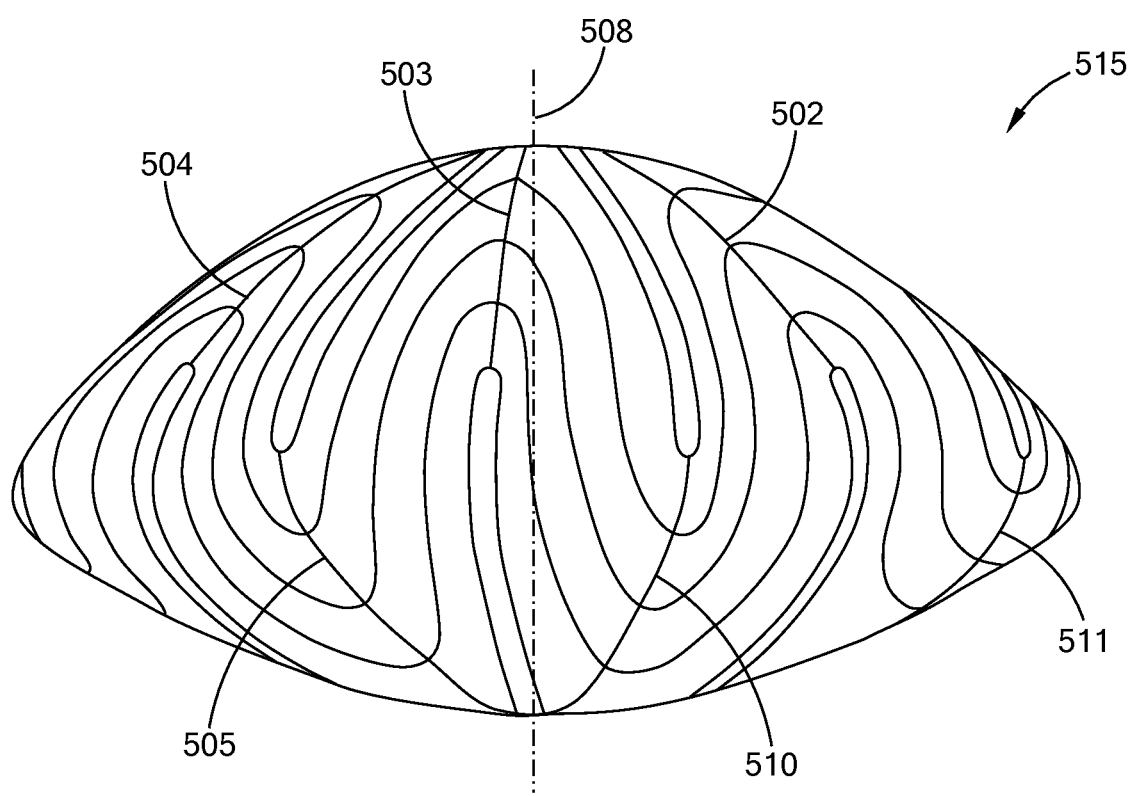
Figure 5C:
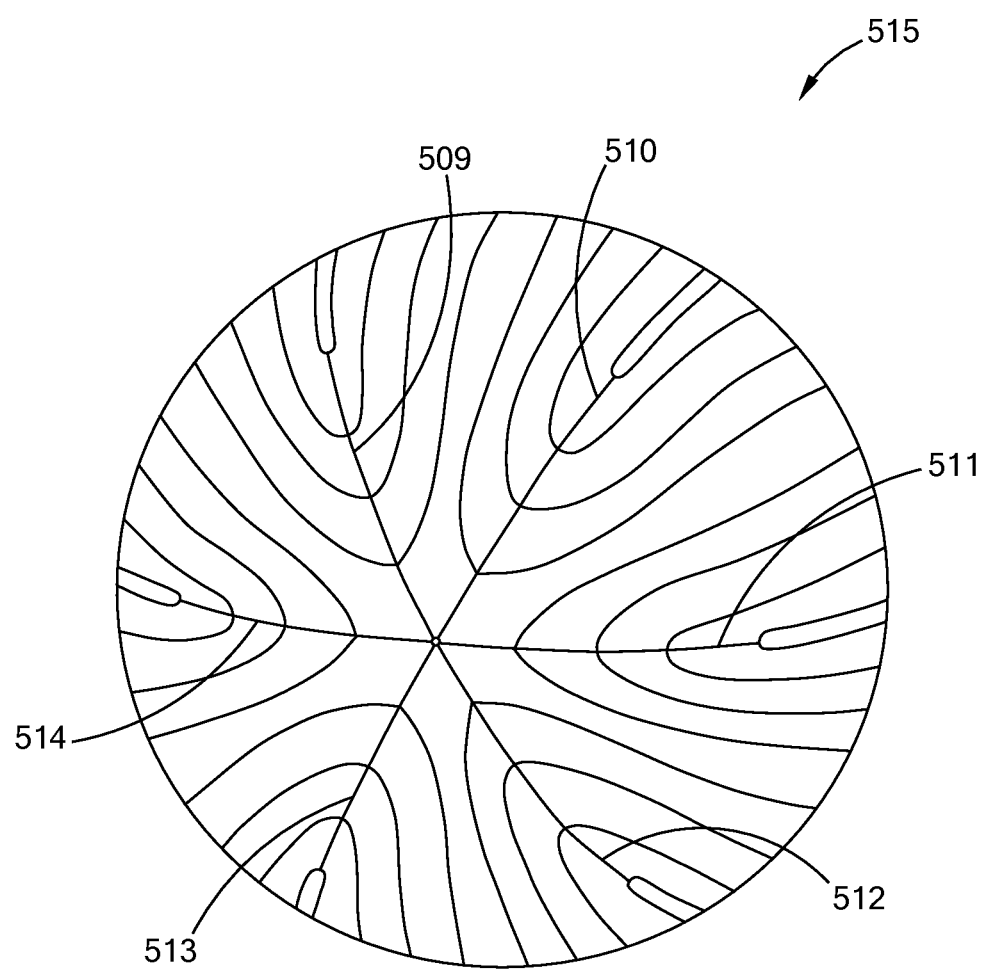

FIGS. 5A-C illustrate the six branched or star suture geometry in the context of the structure found in the infantile layer of the nucleus 515 of the lens. Thus, these figures provide a more detailed view of the structures illustrated as layer 124 of FIG. 1A. In FIGS. 5A-C the view of the layer of the lens is rotated from the posterior side FIG. 5A to a side view FIG. 5B to the anterior side FIG. 5C. Thus, this layer of the nucleus has six posterior suture lines 501, 502, 503, 504, 505, and 506. This layer of the nucleus also has six anterior suture lines 509, 510, 511, 512, 513, and 514. The anterior suture lines are longer than the posterior suture lines and these lines are staggered when viewed along the AP axis 508. The lens fibers, which form the layers of the nucleus, are shown by lines 507, it being understood that these are only illustrative lines and that in the actual natural layer of the lens there would be many times more fibers present.

The shape of the outer surface of the lens essentially follows the infantile nucleus 515, which is a biconvex shape. Thus, the anterior and posterior sides of this layer of the lens have different curvatures, with the anterior being flatter. These curvatures generally follow the curvature of the cortex and the outer layer and general shape of the lens. These curvatures also generally follow the curvature of the fetal nucleus 415. Thus, the lens can be viewed as a stratified structure consisting of long crescent fiber cells arranged end to end to form essentially concentric or nested shells, with the infantile nucleus 515 having the fetal nucleus 415 nested within it. As development continues through adolescence, additional fiber layers grow containing between 6 and 9 sutures.

Figure 6A:
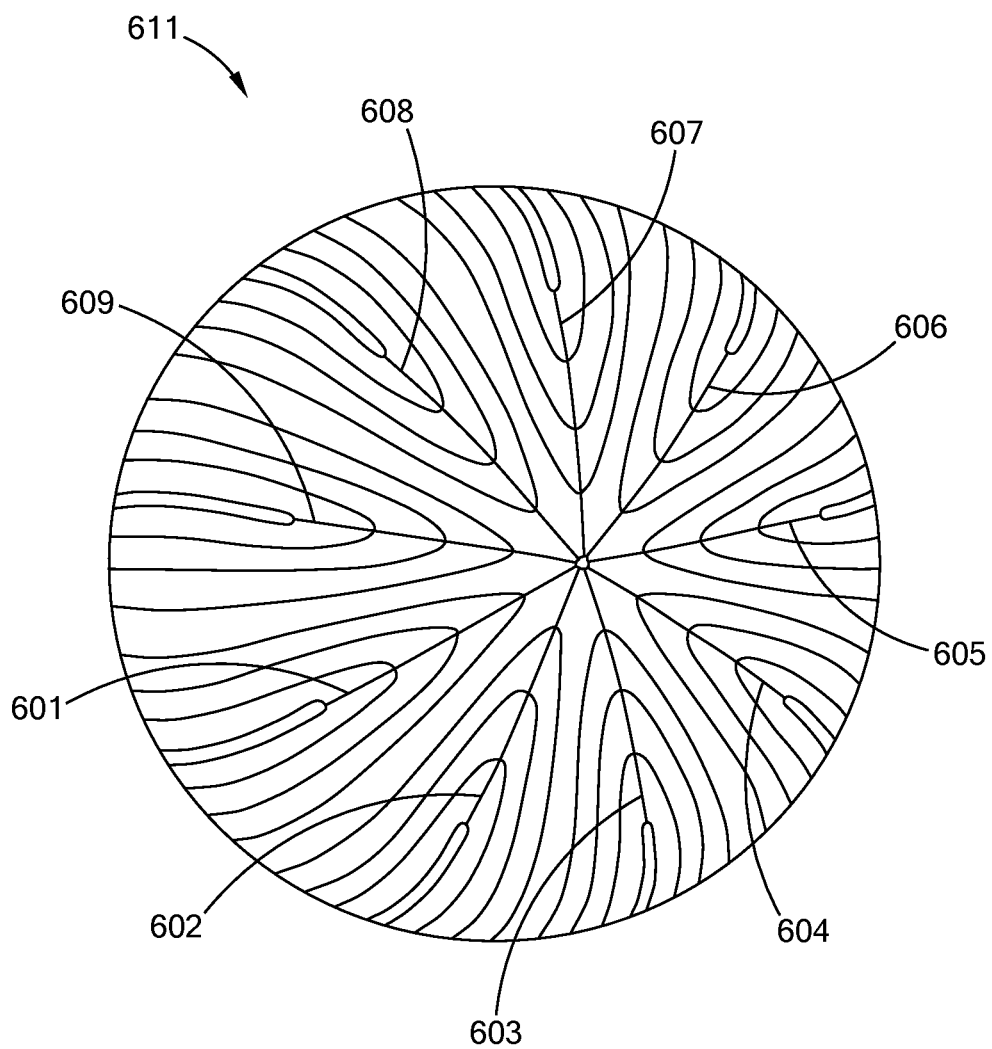
FIGS. 6A, 6B and 6C are diagrams representing posterior, side and anterior elevation views, respectively of the geometry used for the development of laser shot patterns based upon the structure of the adolescent nucleus (nine suture branch nucleus).
Figure 6B:
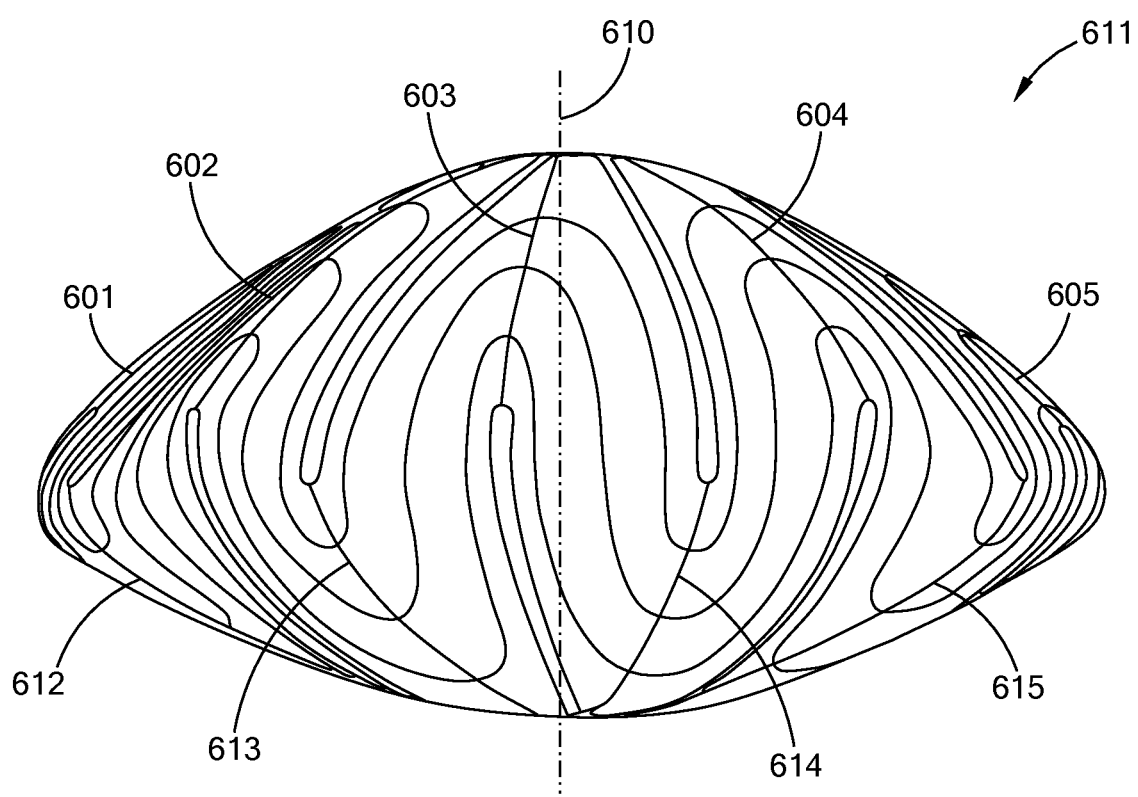
Figure 6C:
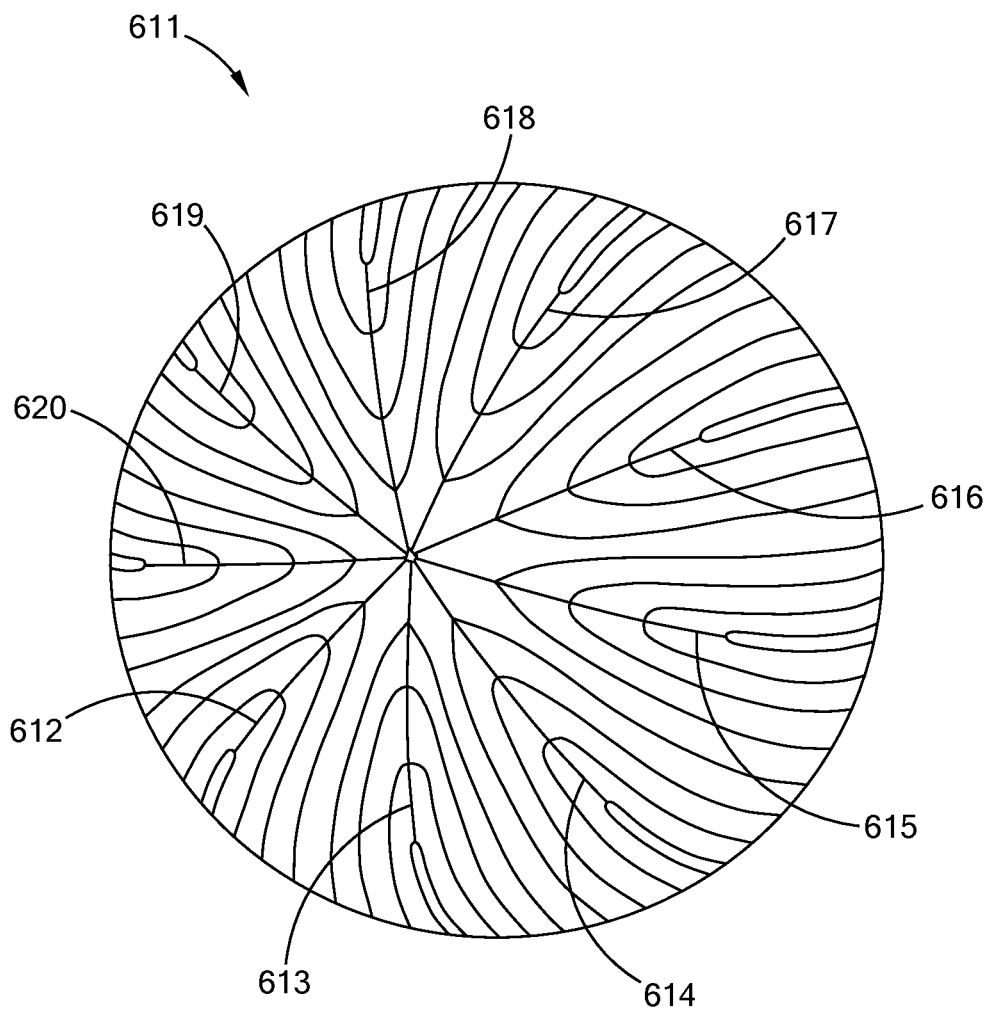

FIGS. 6A-C illustrate the nine branched or star suture geometry in the context of the structure found in the adolescent layer of the nucleus 611 of the lens. Thus, these figures provide a more detailed view of the structures illustrated as layer 126 of FIG. 1A. In FIGS. 6A-C the view of the layer of the lens is rotated from the posterior side FIG. 6A to a side view FIG. 6B to the anterior side FIG. 6C. Thus, this layer of the nucleus has nine posterior suture lines 601, 602, 603, 604, 605, 606, 607, 608 and 609. This layer of the nucleus also has nine anterior suture lines 612, 613, 614, 615, 616, 617, 618, 619 and 620. The anterior suture lines are longer than the posterior suture lines and these lines are staggered when viewed along the AP axis 610. The lens fibers, which form the layers of the nucleus, are shown by lines 621; it being understood that these are only illustrative lines, and that in the actual natural layer of the lens there would be many times more fibers present.

The outer surface of the cornea follows the adolescent nucleus 611, which is a biconvex shape. Thus, the anterior and posterior sides of this layer have different curvatures, with the anterior being flatter. These curvatures generally follow the curvature of the cortex and the outer layer and general shape of the lens. These curvatures also generally follow the curvature of the fetal nucleus 415 and the infantile nucleus 515, which are nested within the adolescent nucleus 611. Thus, the lens can be viewed as a stratified structure consisting of long crescent fiber cells arranged end to end to form essentially concentric or nested shells. As development continues through adulthood, additional fiber layers grow containing between 9 and 12 sutures.

Figure 7A:
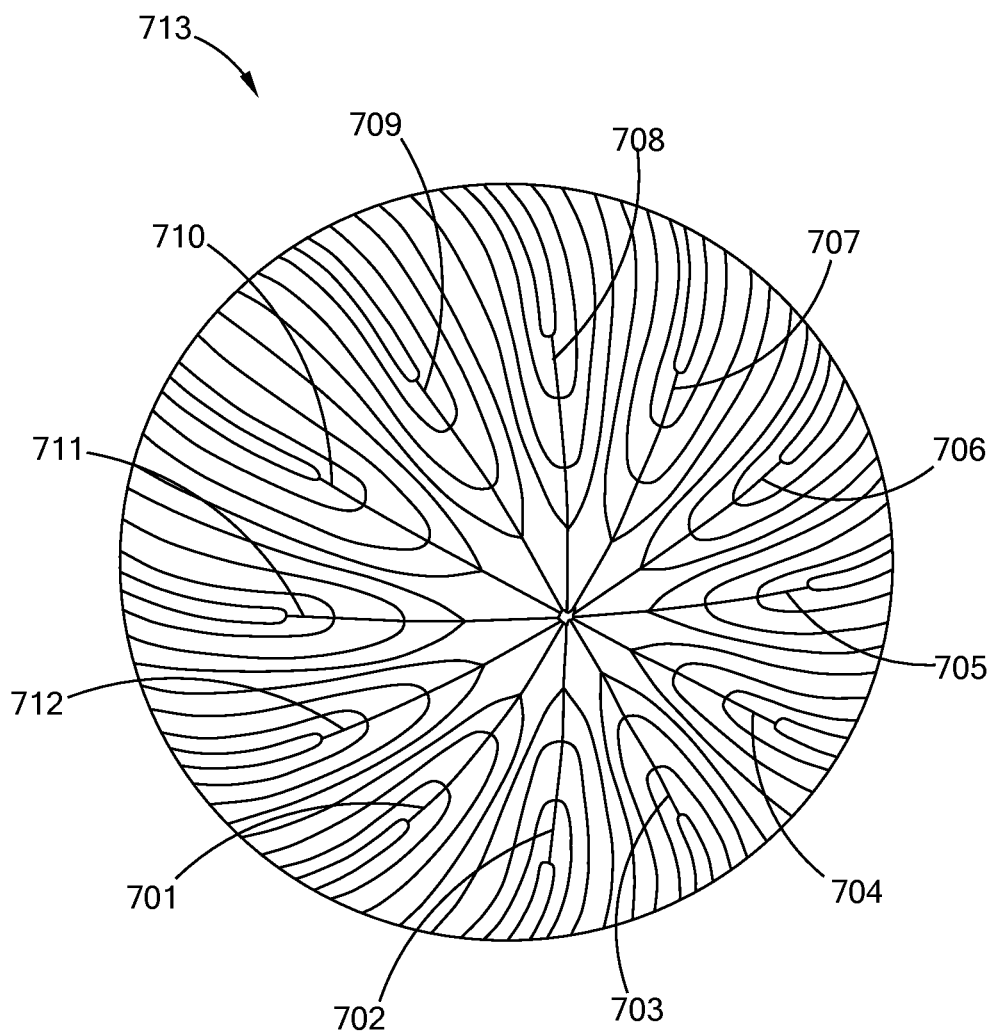
FIGS. 7A, 7B and 7C are diagrams representing posterior, side and anterior elevation views, respectively of the geometry used for the development of laser shot patterns based upon the structure of the an adult nucleus (12 suture branch).
Figure 7B:
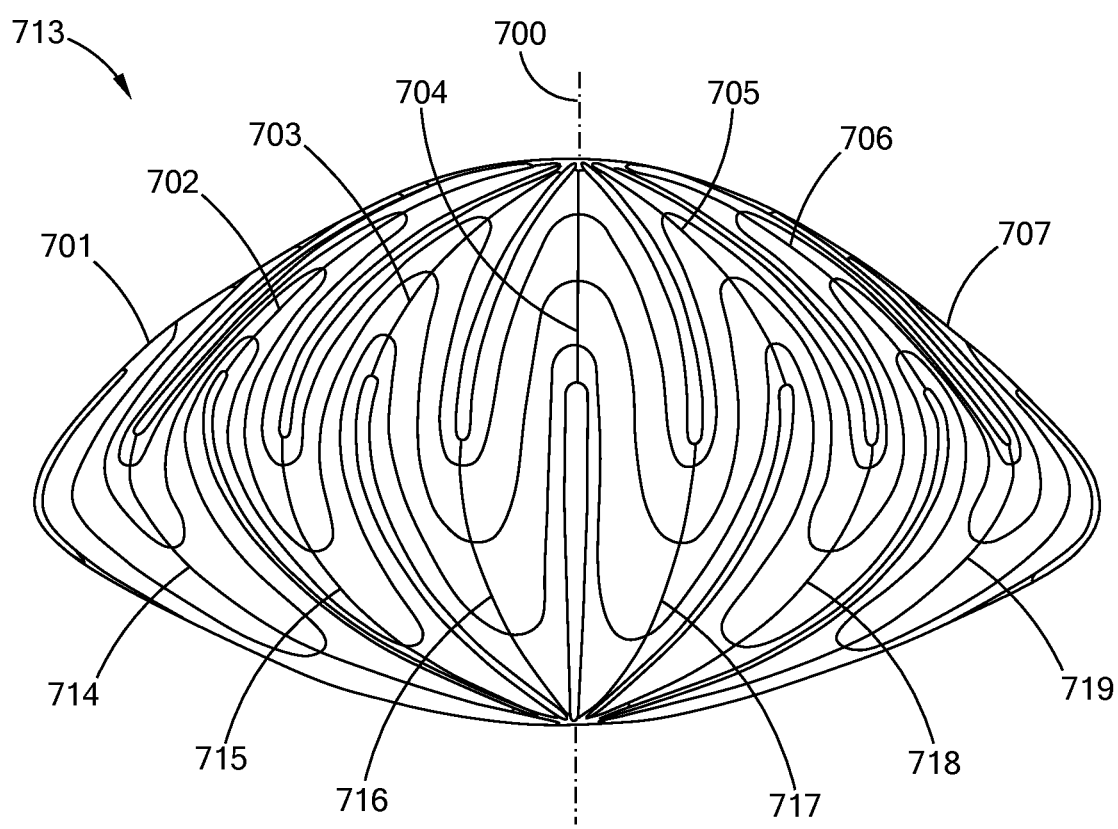
Figure 7C:
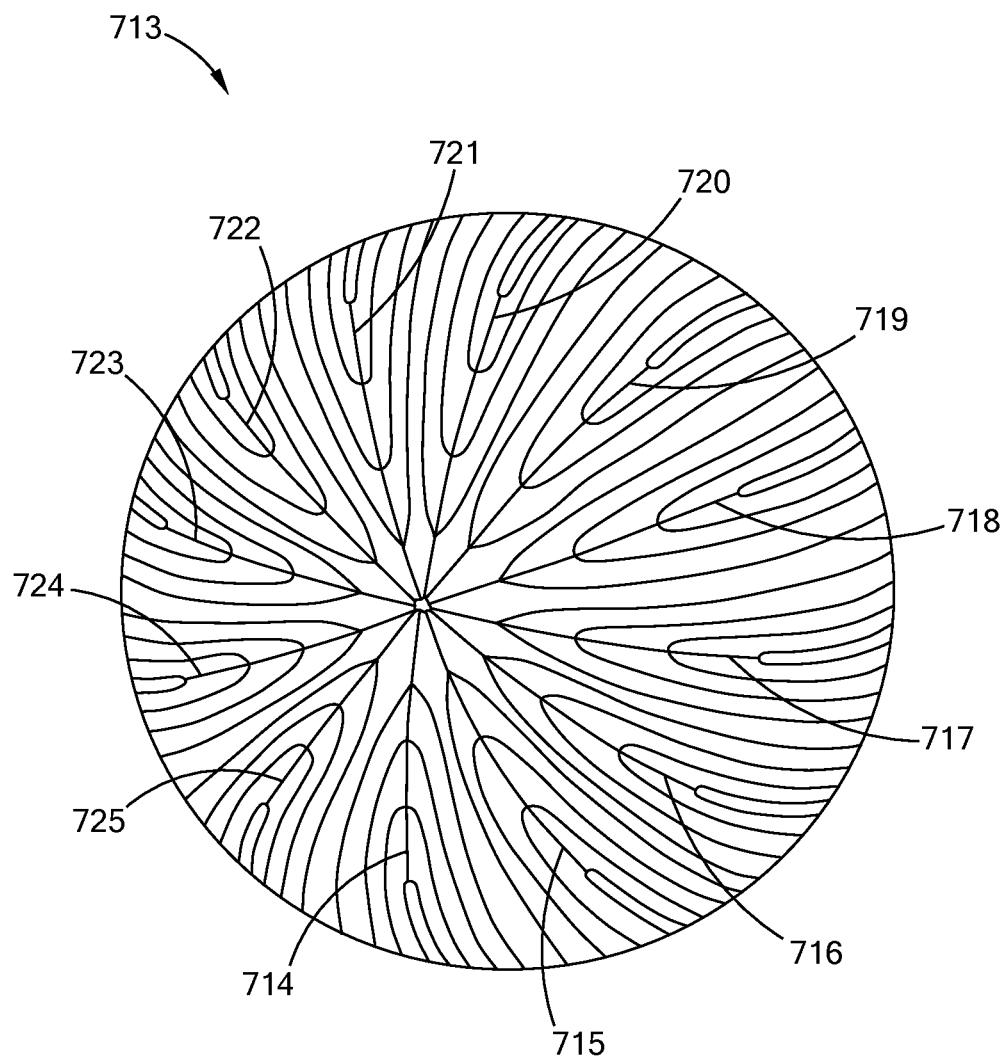

FIGS. 7A-C illustrates the twelve branched or star suture geometry in the context of the structure found in the adult layer of the nucleus 713 of the lens. Thus, these figures provide a more detailed view of the adult layer 128 depicted in FIG. 1A. In FIGS. 7A-C the view of the layer of the lens is rotated from the posterior side FIG. 7A to a side view FIG. 7B to the anterior side FIG. 7C. Thus, the adult layer of the nucleus has twelve posterior suture lines 701, 702, 703, 704, 705, 706, 707, 708, 709, 710, 711, and 712. This layer of the nucleus also has twelve anterior suture lines 714-725. The anterior suture lines are longer than the posterior suture lines and these lines are staggered when viewed along the AP axis 726. The lens fibers, which form the layers of the nucleus, are shown by lines 728; it being understood that these are only illustrative lines, and that in the actual natural layer of the lens there would be many times more fibers present.

The adult nucleus 713 is a biconvex shape that follows the outer surface of the lens. Thus, the anterior and posterior sides of this layer have different curvatures, with the anterior being flatter. These curvatures follow the curvature of the cortex and the outer layer and shape of the lens. These curvatures also generally follow the curvature of the adolescent nucleus 611, the infantile nucleus 515 and the fetal nucleus 415 and the embryonic nucleus, which are essentially concentric to and nested within the adult nucleus 611. Thus, the lens can be viewed as a stratified structure consisting of long crescent fiber cells arranged end to end to form essentially concentric or nested shells.

A subsequent adult layer having 15 sutures may also be present in some individuals after age 40. This subsequent adult layer would be similar to the later adult layer 713 in general structure, with the recognition that the subsequent adult layer would have a geometry having more sutures and would encompass the later adult layer 713; and as such, the subsequent adult layer would be the outermost layer of the nucleus and would thus be the layer further from the center of the nucleus and the layer that is youngest in age.

In general, embodiments of the present invention provides for the delivery of the laser beam in patterns that utilize, or are based at least in part on, the lens suture geometry and/or the curvature of the lens and/or the various layers within the nucleus; and/or the curvatures of the various layers within the nucleus; and/or the suture geometry of the various layers within the nucleus. As part of embodiments of the present invention the concept of matching the curvature of the anterior ablations to the specific curvature of the anterior capsule, while having a different curvature for posterior ablations, which in turn match the posterior curvature of the lens is provided. Anterior and posterior curvatures can be based on Kuszak aged lens models, Burd's numeric modeling, Burd et al. Vision Research 42 (2002) 2235-2251, or on specific lens measurements, such as those that can be obtained from the means for determining the position of the lens with respect to the laser. Thus, in general, these laser delivery patterns are based in whole and/or in part on the mathematical modeling and actual observation data regarding the shape of the lens, the shape of the layers of the lens, the suture pattern, and the position of the sutures and/or the geometry of the sutures.

Moreover, as set forth in greater detail, it is not necessary that the natural suture lines of the lens or the natural placement of the layers of the lens be exactly replicated in the lens by the laser shot pattern. In fact, exact replication of these natural structures by a laser shot pattern, while within the scope of the invention, is not required, and preferably is not necessary to achieve an increase in accommodative amplitude. Instead, embodiments of the present invention, in part, seeks to generally emulate the natural lens geometry, structures and positioning and/or portions thereof, as well as build upon, modify and reposition such naturally occurring parameters through the use of the laser shot patterns described herein.

Figure 8:
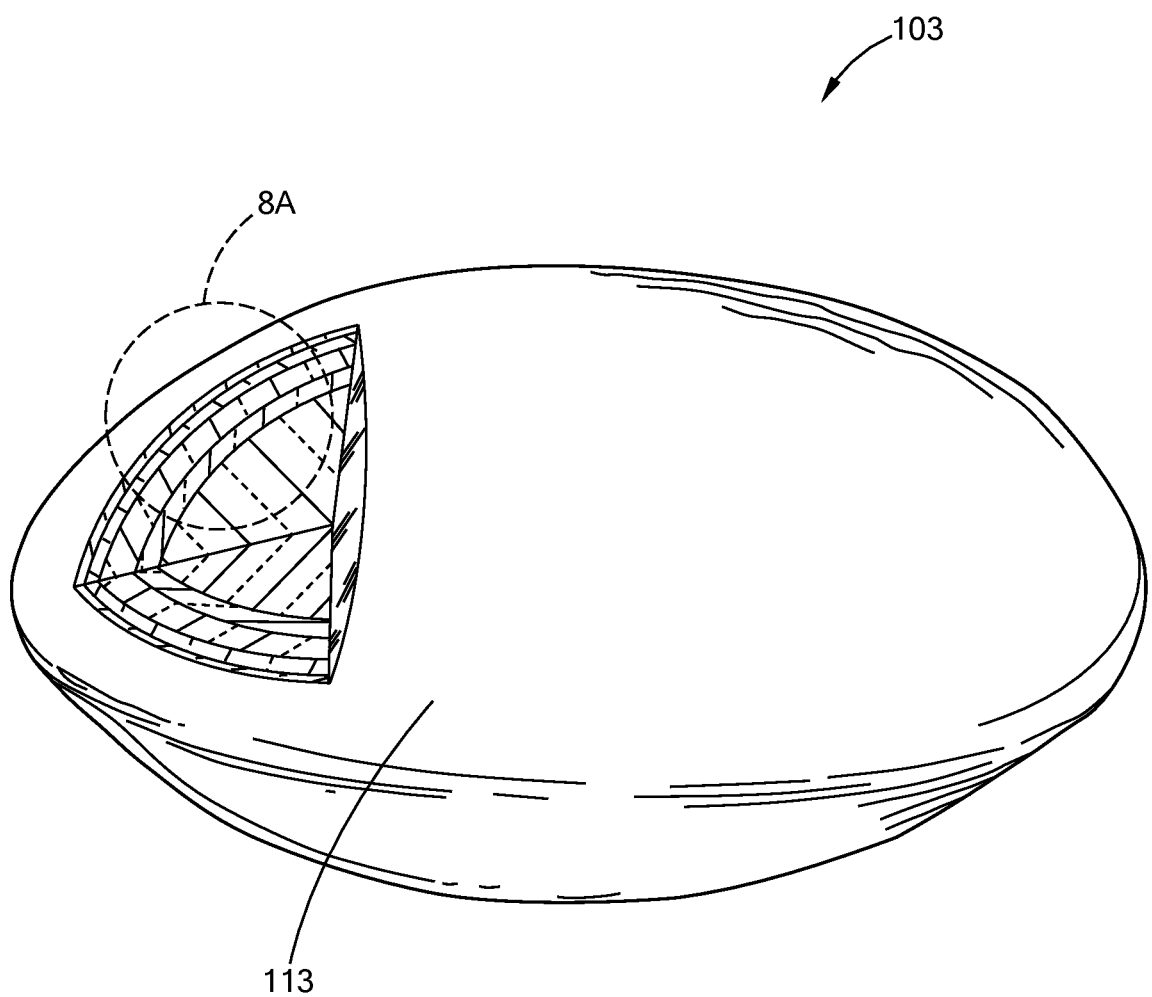
FIGS. 8 and 8A are perspective cutout views of an adult lens representing the placement of essentially concentric shells in accordance with the teachings of the present invention.
Figure 8A:
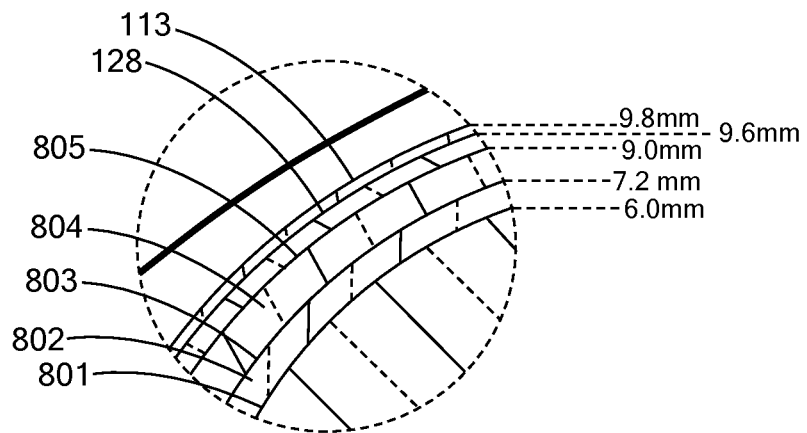

Accordingly, laser beam delivery patterns that cut a series of essentially concentric, i.e., nested, shells in the lens may be employed. Preferably, the shells would essentially follow the anterior and posterior curvature of the lens. Thus, creating in the lens a series of cuts which resemble the nucleus layers of FIGS. 4, 5, 6 and 7. These cuts may follow the same geometry, i.e., shape and distance from the center, of these layers or may follow only a part of that geometry. One example of these shells is illustrated in FIG. 8, which provides a lens 103, a first shell cut 801, a first shell 802, a second shell cut 803, a second shell 804 and a third shell cut 805. The adult nucleus 128 and cortex 113 are also provided. Thus, the tell shell refers to the lens material and the term shell cut refers to the laser beam delivery pattern and consequently the placement of the laser beam shots in the lens in accordance with that pattern. More or less shell cuts, and thus shells may be utilized. Moreover, the cuts may be such that they in effect create a complete shell, i.e., the shell and shell cuts completely encompass a volume of lens material. The cuts may also be such that less than a complete shell is formed. Thus, the creation of partial shells, by the use of partial shell cuts, may be employed. Such partial cuts would for example be only a portion of a shell e.g., the anterior quartile, the anterior half, the posterior quartile, stacked annular rings, staggered annular rings, and/or combinations thereof. Such partial shells and shell cuts may be any portion of a three dimensional form, including ellipsoid, spheroids and combinations thereof as those terms are used in their broadest sense that in general follows the contours of the lens, capsule, cortex, nucleus, and/or the layers of the lens including the layers of the nucleus. Moreover, the use of complete and partial shells and shell cuts may be used in a single lens. Thus, by way of illustration of this latter point, the first and second cuts 801 and 803 are annular cuts, while the third cut is a complete cut.

A further use of partial shells is to have the shape of the shells follow the geometry and/or placement of the suture lines. Thus, partial pie shaped shells are created, by use of partial pie shaped shell cuts. These cuts may be placed in between the suture lines at the various layers of the lens. These partial shells may follow the contour of the lens, i.e., have a curved shape, or they may be flatter and have a more planar shape or be flat. A further use of these pie shape shells and shell cuts would be to create these cuts in a suture like manner, but not following the natural suture placement in the lens. Thus, a suture like pattern of cuts is made in the lens, following the general geometry of the natural lens suture lines, but not their exact position in the lens. In addition to pie shaped cuts other shaped cuts may be employed, such as by way of illustration a series of ellipses, rectangular planes or squares.

In addition to the use of shells and partial shells, lines can also be cut into the lens. These lines can follow the geometry and/or geometry and position of the various natural suture lines. Thus, a laser shot pattern is provided that places shots in the geometry of one or more of the natural suture lines of one or more of the various natural layers of the lens as shown in FIGS. 4, 5, 6, and 7, as well as in the 15 suture line layer, or it may follow any of the other patterns in the continuum of layers in the lens. These shot patterns can follow the general geometry of the natural suture lines, i.e., a series of star shapes with the number of legs in each star increasing as their placement moves away from the center of the lens. These star shaped shot patterns may follow the precise geometry of the natural suture patterns of the layers of the lens; or it can follow the exact geometry and placement of the sutures, at the same distances as found in the natural lens or as determined by modeling of the natural lens. In all of these utilizations of star patterns one or more stars may be cut. The length of the lines of the legs of the star may be the longer, shorter or the same length as the natural suture lines. Moreover, if the length is shorter than the natural length of the suture lines, it may be placed toward the center of the star shape, i.e. the point where the lines join each other, or towards the end of the suture line, i.e., the point furthest on the suture line from the joining point. Further, if the cut is towards the end of the suture line it may extend beyond the suture line or may be co-terminus therewith. Moreover, partial star shaped cuts can be used, such as cuts having a "V" shape, or vertical or horizontal or at an angle in between. These linear cuts, discussed above, are in general referred to herein as laser created suture lines. Moreover, laser created suture lines may be grouped together to in effect form a shell or partial shell.

Figure 3:
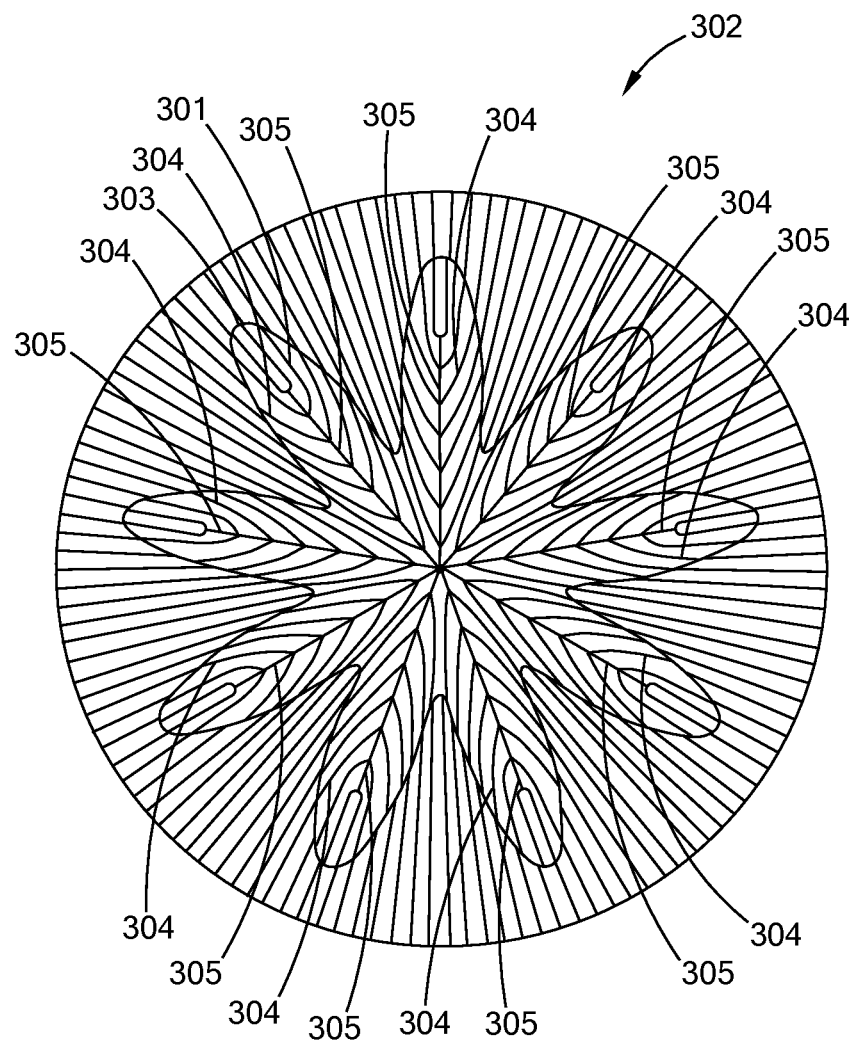
FIG. 3 is a diagram of the anterior surface of a lens normal to the AP axis illustrating a laser shot pattern having a flower like shape, which has a contour generally following approximately the last 15% of the fiber length from the end of the fiber.

At present, it is theorized that the use of cuts near the end of the suture lines may have the greatest effect on increasing accommodative amplitude because it is believed that the ends of fibers near the anterior and posterior poles (the point where the AP axis intersects the lens) of the lens are more free to move then the portions of fibers near the equator where there is a greater number of gap junctions which bind fiber faces. At present, it is postulated that it is approximately the last 15% of the fiber length that is most free in the youthful lens with high accommodative amplitude. It is further theorized that fiber layers tend to become bound with age due to a combination of increase in surface roughness and compaction due to growth of fiber layers above. Thus, as illustrated in FIG. 3 a shot pattern 301 is provided to an anterior portion of a layer 302 of the lens. This shot pattern 301 has a contour 303 that follows the contour of approximately the last 15% of fiber length of fibers, represented by lines 304. Thus, the shell cut resembles the shape of a flower. Additionally, the number of petals in the flower shaped shell should correspond to the number of suture lines 305 at that growth layer. Thus, it is theorized that this partial shell cut and/or cuts will have the effect of unbinding the layers and returning the lens to a more youthful increased amplitude of accommodation. Similarly, using partial shells, annular partial shells or planar partial shells in this general area, i.e., the general area at or near the ends of the suture lines, may be employed for the same reasons. This theory is put forward for the purposes of providing further teaching and to advancing the art. This theory, however, is not needed to practice the invention; and the invention and the claims herein are not bound by or restricted by or to this theory.

The use of laser created suture lines, including star shaped patterns may also be used in conjunction with shells, partial shells and planar partial shells. With a particular laser shot pattern, or series of shot patterns, employing elements of each of these shapes. These patterns may be based upon the geometry shown in FIGS. 4-7 as well as the 15 suture line geometry discussed herein; they may follow that geometry exactly, in whole or in part; and/or they may follow that geometry, in whole or in part, as well as following the position of that geometry in the lens. Although a maximum of 15 suture lines is known in the natural lens, more than 15 laser created suture lines may be employed. Moreover, as provided herein, the lens has multiple layers with a continuum of suture lines ranging from 3 to 15 and thus, this invention is not limited to the suture patents of FIGS. 4-7, but instead covers any number of suture lines from 3 to 15, including fractions thereof.

It is further provided that volumetric removal of the lens can be performed to correct refractive errors in the eye, such as myopia, hyperopia and astigmatism. Thus, the laser shot pattern is such that a selected volume and/or shape of lens material is removed by photodisruption from the lens. This removal has the affect of alternating the lens shape and thus reducing and/or correcting the refractive error. Volumetric removal of lens tissue can be preformed in conjunction with the various shot patterns provided for increasing accommodative amplitude. In this manner both presbyopia and refractive error can be addressed by the same shot pattern and/or series of shot patterns. The volumetric removal of lens tissue finds further application in enhancing corrective errors for patients that have had prior corneal laser visions correction, such as LASIK, and/or who have corneas that are too thin or weak to have laser corneal surgery.

In embodiments of the laser shot patterns provided herein it is generally preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed;

resulting in a structural change affecting accommodative amplitude and/or refractive error. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 μm size spot with an energy sufficient to cause photodisruption, a spacing of 20 μm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 μm spot size with a 10 μm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock waive propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Sectional patterns may be employed. Such patterns would include the cube patterns, variations in the shape and size of this cube pattern, concentric cylinders, radial planes, horizontal planes and vertical planes, partial shells and shells, and combinations thereof. As used to describe these patterns, vertical refers to essentially parallel to the optical axis, i.e., the AP axis. These sectional patterns are employed within, or to comprise, a particular shaped volume, such as the shaped volumes in FIGS. 15-19. Thus, these sectional patterns can be used in shaped volumes that provide for positive or negative refractive corrections. Further, these shaped patterns can be used in shaped volumes that result in shaped structural weakening, which causes shape change and results in a positive or negative refractive correction. Additionally, shaped structural weakening may also result in increased accommodative amplitude.

Moreover, these patterns can be employed in conjunction with each other, i.e., vertical and horizontal, or in isolation, i.e., only vertical or horizontal, at various locations in the lens, which locations can range from totally separate, to slightly overlapping, to overlapping. Additionally, by selectively arranging placement and density of these patterns and/or combination of primarily vertical and primarily horizontal patterns, local structure in the lens can be weakened by varying and predetermined amounts, which can result in selective flexibility and shape changes. Thus, through such selective placement and density determinations shaped structural weakening may be accomplished.

Optical performance and optical quality are dependent upon the surface shape and quality of the lens. Thus, to balance increasing accommodative amplitude via increased flexibility with maintaining and/or obtaining lens shape for desired optical performance and optical quality various combinations, densities and placements of these patterns may be employed. Moreover, these primarily horizontal patterns may be selected such as to change the lens surface shape in a predetermined manner.

In an embodiment a combination of first cuts to create nested shells that in general follow the shape of and are positioned near the outer surface of the lens and second cuts to create a pattern directed toward the inner portions of the lens, with both the first cuts and the second cuts not cutting the material near the optical axis of the lens is provided. This combination of cuts, with a central portion of the lens avoided, provides for both an increase in accommodative amplitude, as well as, an increase in the refractive power of the lens. The first cuts can range from one shell to many nested shells. They can be in the form of partial or complete shells, or a combination of both. In the case of partial shells they can be annular. The second cuts can be shells, cubes, or other patterns including combinations of horizontal and vertical cuts to cover a specific volume of material. The size of the area that is not cut by these patterns can range from a radius of about 0.1 mm to a radius about 2 mm, specifically from about 0.25 mm to about 1.5 mm, and more specifically as set forth in the following examples. In addition to the cylindrically shaped areas addressed above and in the examples, other shapes for this area may be utilized and would have widths from about 0.5 mm to about 4 mm, specifically from about 0.5 mm to about 3 mm and more specifically about 1 mm, about 2 mm and about 3 mm. Further, this radius or width can vary for different shells in the first cut and for different locations of the second cuts. The use of the terms "first" and "second" in describing this combination of cuts is meant solely for the purpose of identification of these cuts. These terms are not intended to and do not imply that one cut is made before or after the other. In fact, all sequences of making these cuts are contemplated. Additionally, it being readily understood that the shell cut is formed by and thus corresponds to a laser shot pattern.

Without further elaboration, it is believed that one skilled in the art can, using the preceding description, utilize the present inventions to its fullest extent. The following specific embodiments are, therefore, provided as examples of the invention and should be construed as being merely illustrating and not limiting the scope of the invention or the disclosure herein in any way whatsoever.

The following Examples 1 to 16 are based upon measured lens data and lens data that is obtained by using Burd modeling, which model is set forth in Burd et al., Numerical modeling of the accommodating lens, Visions Research 42 (2002) 2235-2251. The Burd model provides the following algorithm for anterior and/or posterior shape:

$$Z = aR^5 + bR^4 + cR^3 + dR^2 + f$$

The coefficients for this algorithm are set forth in Table I.

TABLE I

|  | a | b | c | d | f |
|---|---|---|---|---|---|
| Anterior (11-year) | −0.00048433393427 | 0.00528772036011 | −0.01383693844808 | −0.07352941176471 | 2.18 |
| Posterior (11-year) | 0.00300182571400 | −0.02576464843559 | 0.06916082660799 | 0.08928571428571 | −2.13 |
| Anterior (29-year) | −0.00153004454939 | 0.01191111565048 | −0.02032562095557 | −0.07692307692308 | 2.04 |
| Posterior (29-year) | 0.00375558685672 | −0.03036516318799 | 0.06955483582257 | 0.09433962264151 | −2.09 |
| Anterior (45-year) | −0.00026524088453 | 0.00449862869630 | −0.01657250977510 | −0.06578947368421 | 2.42 |
| Posterior (45-year) | 0.00266482873720 | −0.02666997217562 | 0.08467905191557 | 0.06172839506173 | −2.42 |

Figure 9:
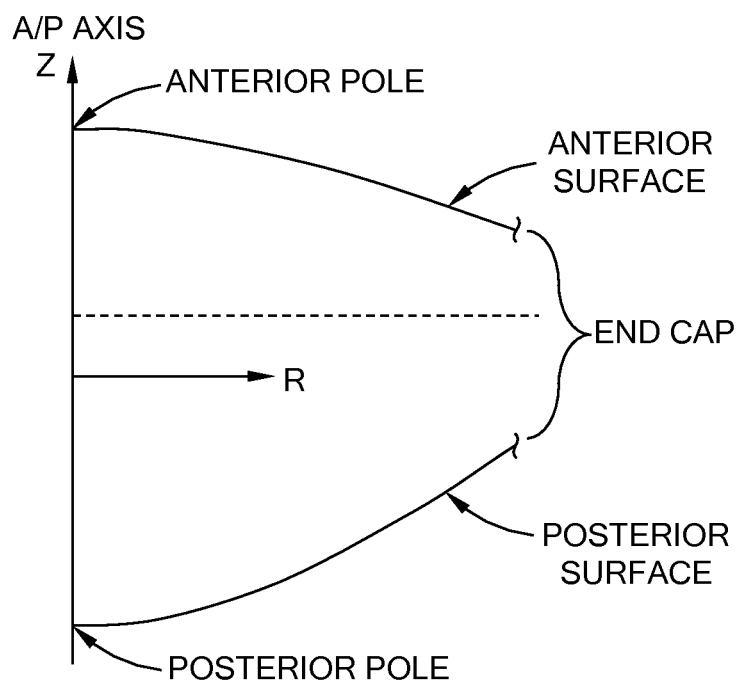
FIG. 9 is a cross-section drawing of the lens relating to the model developed by Burd.

Additionally, the variables Z and R are defined by the drawing FIG. 9.

Figure 10:
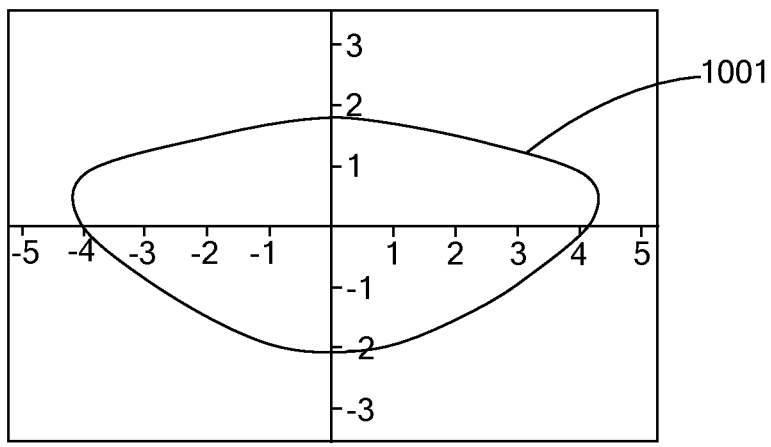
FIG. 10 is a cross-section drawing of a lens based upon the model developed by Burd.
Figure 11:
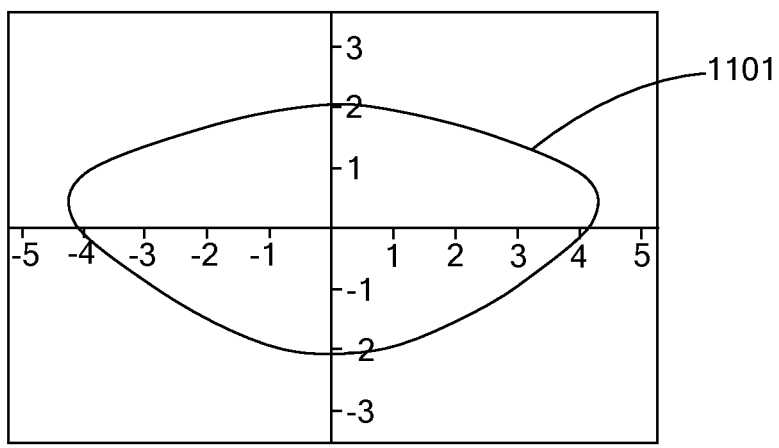
FIG. 11 is a cross-section drawing of a lens based upon the model developed by Burd.
Figure 12:
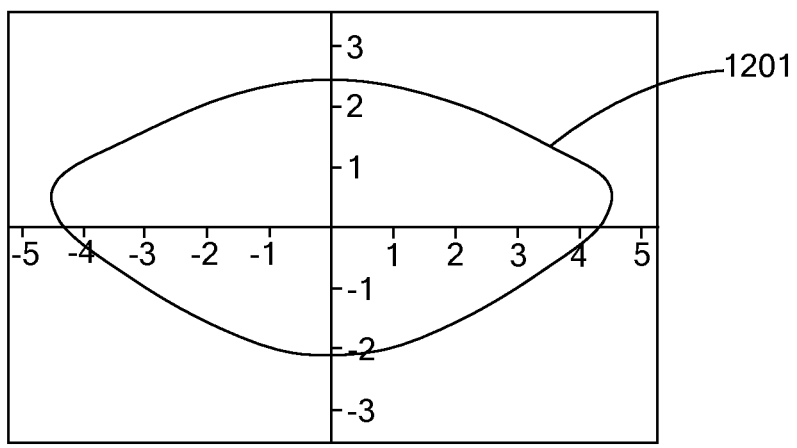
FIG. 12 is a cross-section drawing of a lens based upon the model developed by Burd.

Thus, FIGS. 10, 11 and 12 provide cross sectional views of the lens having an outer surface 1001, 1101, 1201 for three ages, 18, 29 and 45-year old respectively, based upon the Burd model and show growth in size along with shape changes with age. The units for the axes on these drawings, as well as for FIGS. 13 to 19, and 21 to 29 are in millimeters (mm).

Figure 13:
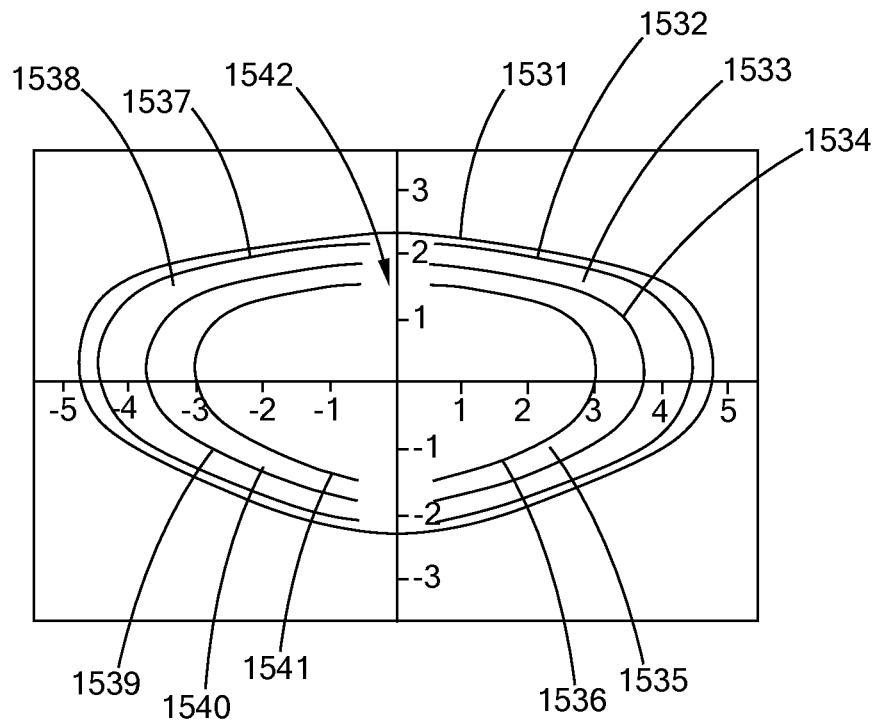
FIG. 13 is a cross-section drawing of a lens showing the placement of a partial shell laser shot pattern in accordance with the teachings of the present invention.

EXAMPLE 1 provides a shot pattern for cutting partial shells on the measured 45-year old lens, and having an excluded defined central zone. Thus, as illustrated in FIG. 13 there is provided an outer surface 1531 of a 45-year old lens, a central zone 1542, partial cuts 1532, 1534, 1536, 1537, 1539 and 1541. This also provided partial shells 1533, 1535, 1538 and 1540. These partial cuts as shown are part of the same generally annularly shaped. Thus, cuts 1532 and 1537, cuts 1534 and 1539, and cuts 1536 and 1541 are the opposite sides respectively of three generally annularly shaped partial.

Figure 14:
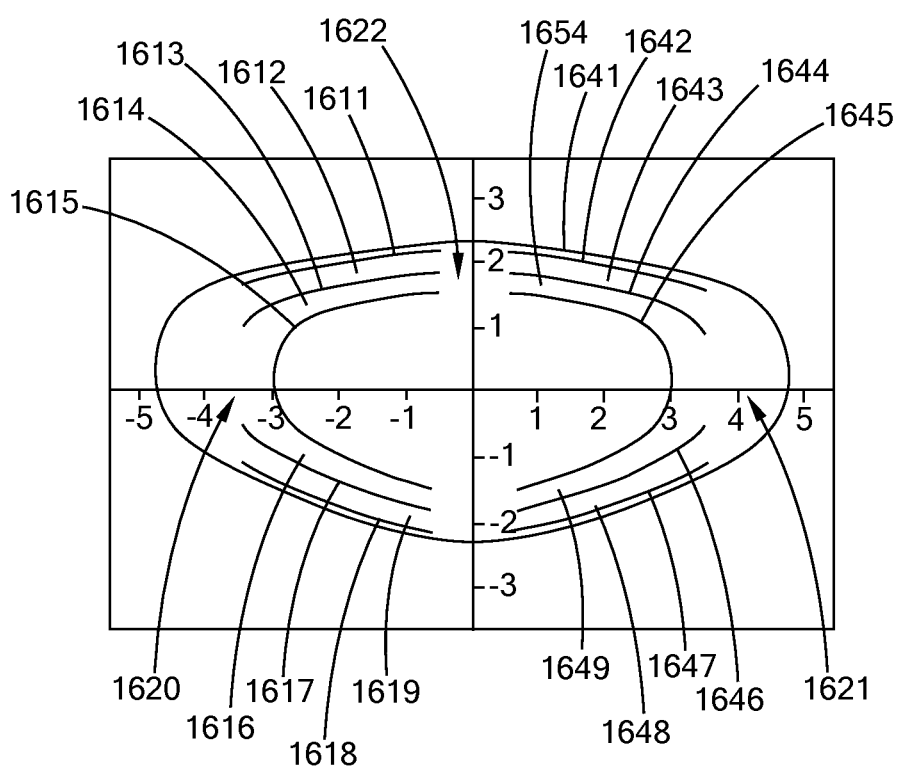
FIG. 14 is a cross-section drawing of a lens showing the placement of a partial shell laser shot pattern in accordance with the teachings of the present invention.

EXAMPLE 2 provides a shot pattern for cutting partial shells on the measured 45-year old lens, and having both an excluded defined peripheral zone and central zone. Thus, as illustrated in FIG. 14, there is provided an outer surface 1641 of a 45-year old lens, a central zone 1622 and two peripheral zones 1620 and 1621. There is further provided partial cuts 1642, 1644, 1645, 1646, 1647, 1611, 1613, 1615, 1617, and 1618 as well as, partial shells 1643, 1648, 1649, 1640, 1612, 1614, 1616 and 1619. As with example 1 and FIG. 13 these cuts are viewed in cross section and thus it is understood that they are opposite sides of generally annular ring shaped cuts, which essentially follow the shape of the lens and which encompasses the central zone 1622. There are thus 5 partial cuts depicted in FIG. 14.

Figure 15:
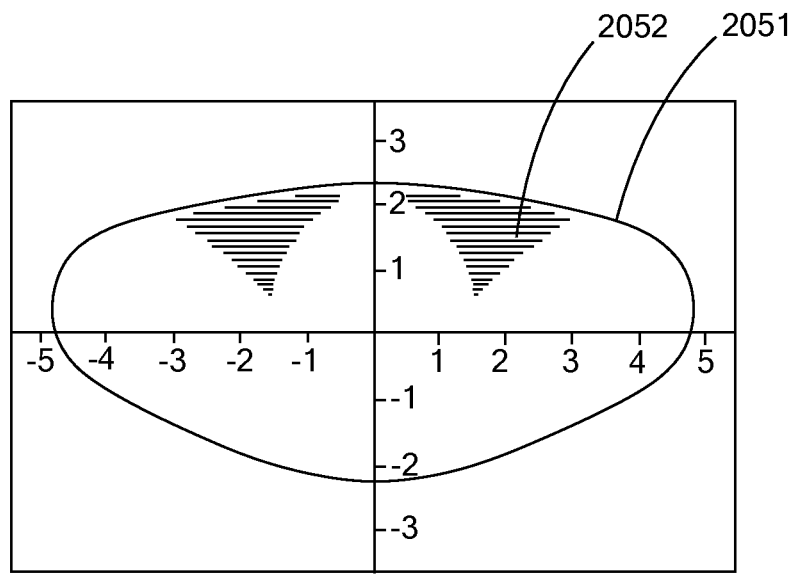
FIGS. 15-19 are cross-section drawings of a lens showing the placement of a volumetric removal laser shot patterns in accordance with the teachings of the present invention.

EXAMPLE 3 provides a shot pattern to cause a refractive change to increase lens power or reduce hyperopia in patients, where the shot pattern is primarily implemented in the anterior region of the lens. This pattern is illustrated in FIG. 15, which provides an outer surface 2051 and thus shape of the lens and a shot pattern 2052.

Figure 16:
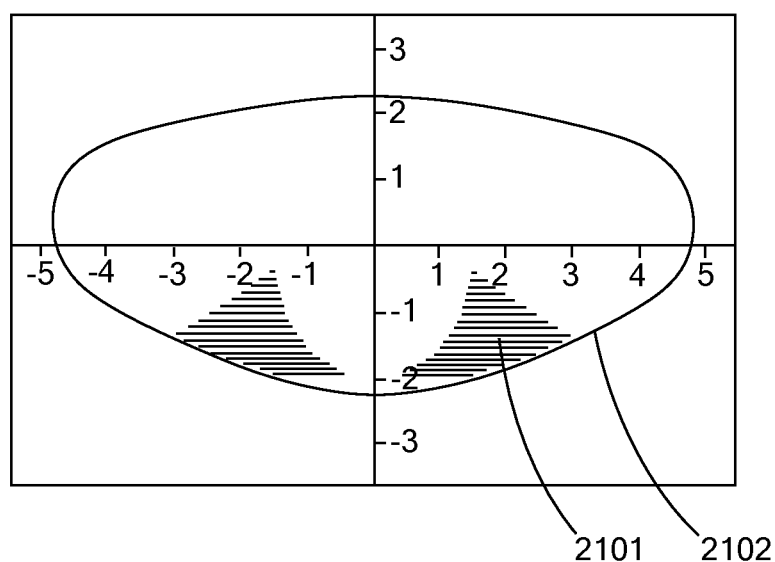

EXAMPLE 4 provides a shot pattern to cause a refractive change to increase lens power or reduce hyperopia in patients, where the algorithm is primarily implemented in the posterior region of the lens. This pattern is illustrated in FIG. 16, which provides an outer surface 2101 and thus shape of the lens and a shot pattern 2102. This example further illustrates a shot pattern having a shape is modified to primarily follow the posterior curve of the lens.

Figure 17:
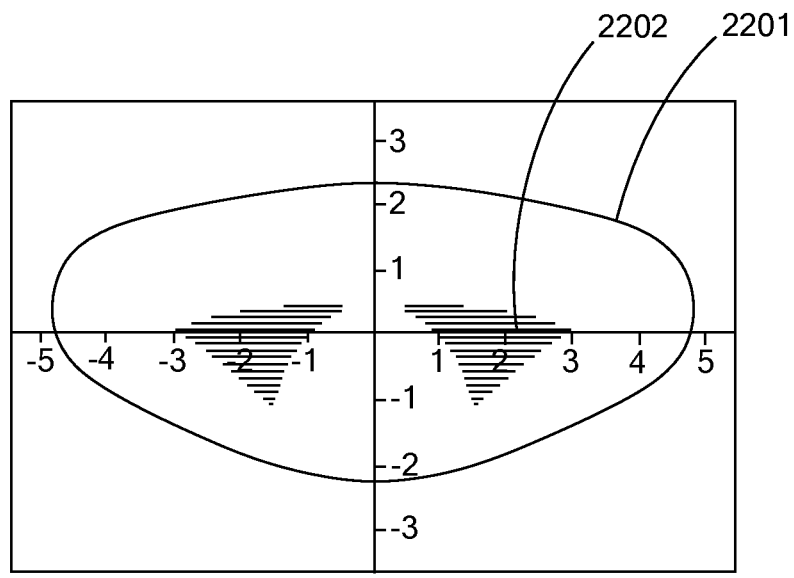

EXAMPLE 5 provides a shot pattern to cause a refractive change to increase lens power or reduce hyperopia in patients, where the shot pattern is primarily implemented in the central region of the lens. Thus, as illustrated in FIG. 17, there is provided an outer surface 2201 of the lens and a shot pattern 2202, which provides a volumetric shape. It further being noted that the anterior shape of the lens or posterior shape of the lens or both can be utilized to determine the shape of the shot pattern and/or volumetric shape.

Figure 18:
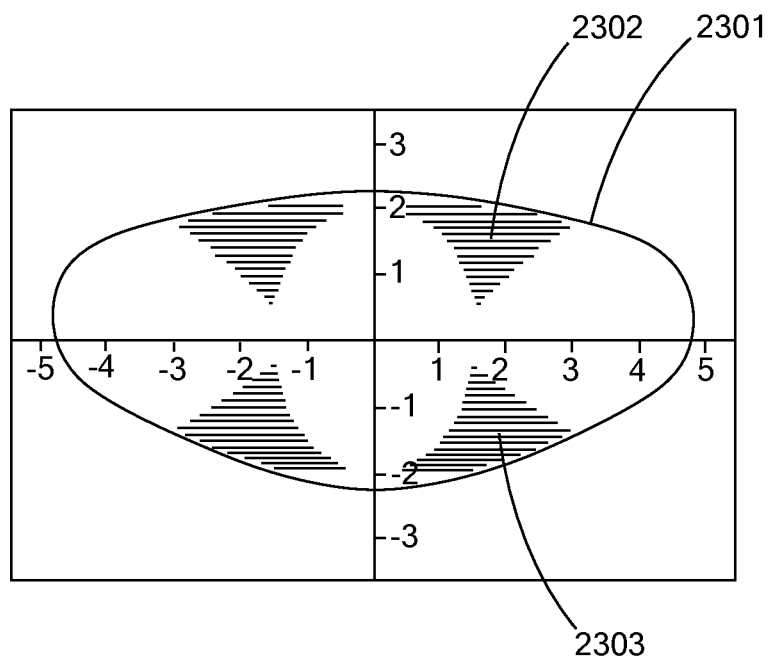

EXAMPLE 6 provides two volumetric shot patterns that follow the shape of the lens surface to which they are adjacent. Thus, as illustrated in FIG. 18, there is provided an outer surface 2301 and thus shape of the lens and a shot pattern having two volumetric shot patterns; a first shot pattern 2302 positioned in the anterior region of the lens and a second shot pattern 2303 positioned in the posterior region, which patterns provide a volumetric shape. Thus, the volumetric shapes to be removed from the lens are located in the anterior and posterior regions of the lens and have a surface that follows the anterior and posterior shape of the lens respectively.

Figure 19:
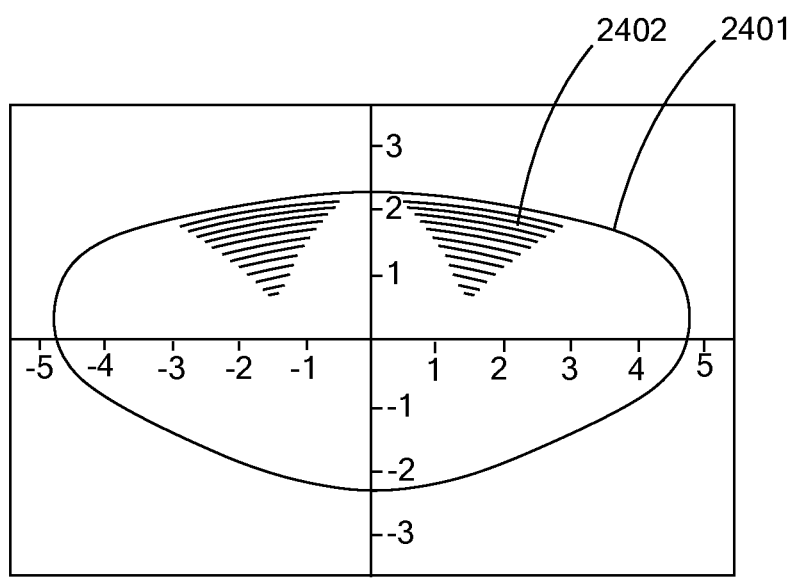
Figures 20A, 20B:
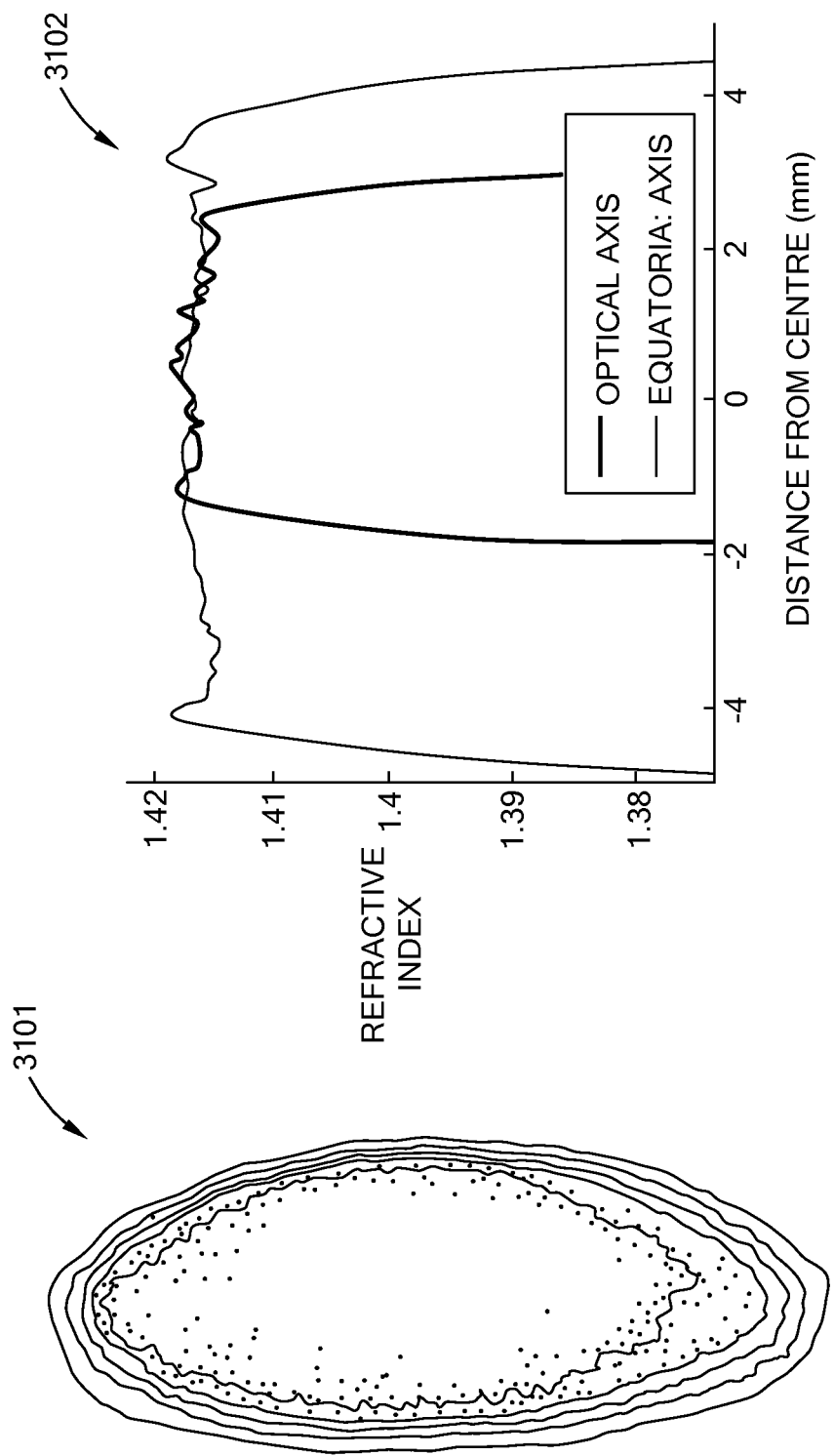
FIGS. 20 A-D are diagrams illustrating youthful vs old age gradient index behavior.
Figures 20C, 20D:
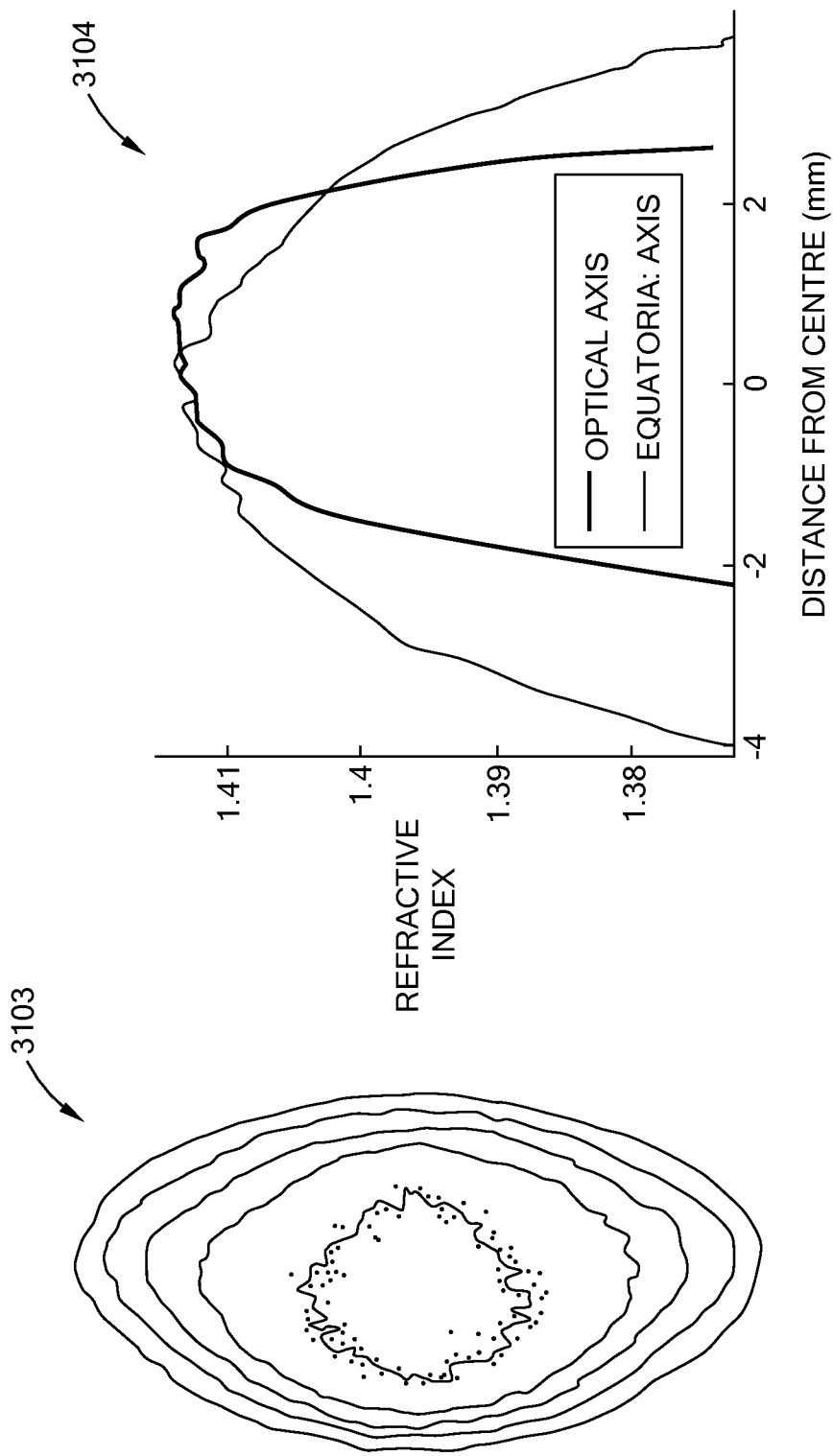

EXAMPLE 7 illustrates a manner in which different shot pattern features are combined to address both refractive errors and those to increase flexibility utilizing a plurality of stacked partial shells, which are partially overlapping. Thus, as illustrated in FIG. 19, there is provided an outer surface 2401 and thus shape of the lens and there are provided partial shell cuts 2402, whose extent is defined by a refractive shape, forming annular rings shaped partial shells 2403. The placement of the partial shell cuts are adjacent the anterior surface of the lens as shown it FIG. 19. The partial shell cuts may similarly be placed adjacent the posterior surface of the lens, in which case they should follow the shape of that surface. Thus, by precisely following the individual shape of the layers within the lens more effective cleaving is obtained.

The shot pattern in the figures associated with EXAMPLES 3, 4, 5 and 6 are shown to cut horizontal partial planes whose extent is defined by a refractive shape. It is to be understood that as an alternative to horizontal planes, vertical partial planes or other orientation cuts whose extent is defined by the refractive shape may be used.

Example 8 relates to gradient index modification of the lens. Moffat, Atchison and Pope, Vision Research 42 (2002) 1683-1693, showed that the natural crystalline lens contains a gradient index of refraction behavior that follows the lens shells structure and dramatically contributes to overall lens power. They also showed that this gradient substantially diminishes, or flattens as the lens ages reducing the optical power of the lens. The loss of gradient index with age most likely explains the so-called Lens Paradox, which presents the conundrum that the ageing lens is known to grow to a steeper curvature shape that should result in higher power, yet the aging lens has similar power to the youthful lens. Essentially it is postulated that the increase in power due to shape changes is offset by the power loss from gradient index loss. Examples of the youthful vs old age gradient index behavior is shown in FIGS. 20A-D, which provides data taken from the more recent work from the same group Jones, Atchison, Meder and Pope, Vision Research 45 (2005) 2352-236. We can see from these figures that the old lens 3101 has a flat index behavior radially 3102 and the young lens 3103 has continuously diminishing index radially 3104 from approximately 1.42 in the center to 1.38 nearer the outer shells of the lens. Thus, based upon this data it is provided to use the photodisruptive laser in the creation of small voids within the lens fiber material which will then fill-in with aqueous humor fluid which has a lower index of refraction and, via area weighting or volume weighting, decrease the net refractive index of a particular region. Accordingly, if different void densities are placed in nested shell volumes, then this would diminish the average index of refraction of essentially concentric regions in a similar manner to the youthful lens.

Figure 21:
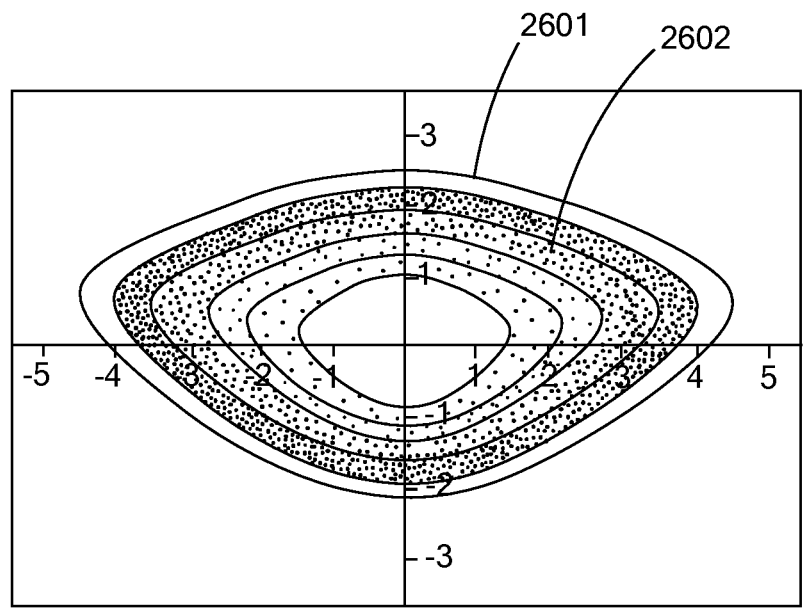
FIG. 21 is a cross-section drawings of a lens showing the placement of a gradient index modification laser shot patterns in accordance with the teachings of the present invention.

EXAMPLE 8 provides a gradient index modification, which has different void densities placed in nested volumes, as shown in FIG. 21. Thus, there is provided a series of nested shot patterns 2602 and a lens outer surface 2601, with each pattern creating an incrementally different void density in the lens material. For example, if a nominal 25% weighting efficiency was obtained in the most densely treated region, filling that volume with 1.38 index of aqueous humor, and the remaining region that was 75% lens material of index 1.42, then the average resultant index of refraction would be 0.25*1.38+0.75*1.42 or 1.41, which we see from FIGS. 20A-D, that would restore the gradient from the center to a 2 mm radius, which is most central optical region for visual function. Thus, FIG. 21 shows a distributed regional treatment of increasing density from the center of the lens to the periphery of the lens.

Examples 9 to 12 further illustrate the teachings and provide illustrative ways in which sectional patterns can be implemented to improve accommodative amplitude and/or refractive error.

Figure 22:
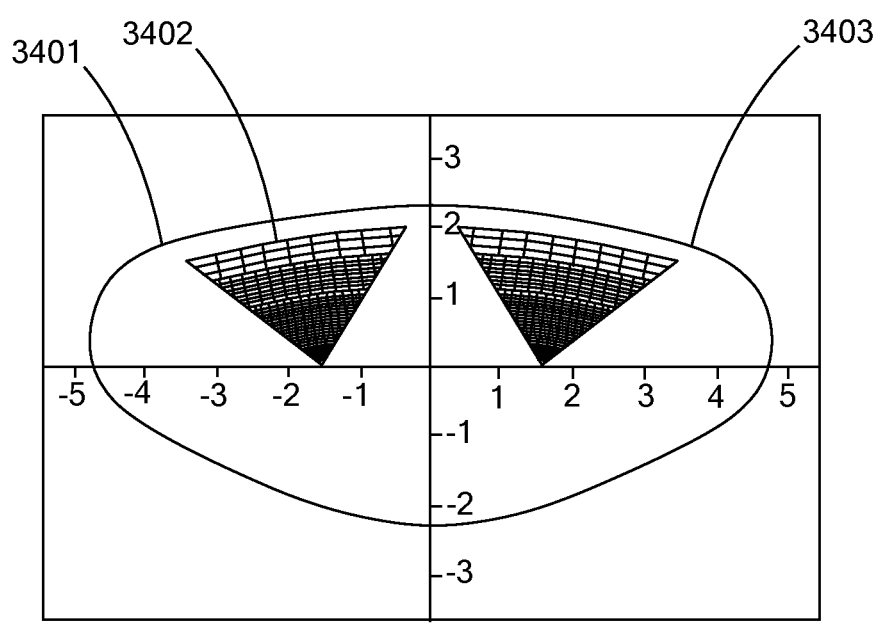
FIG. 22 is diagram illustrating a sectional shot pattern in accordance with the teachings of the present invention.

EXAMPLE 9, as illustrated in FIG. 22, provides within an outer lens surface 3401 a combination of primarily vertical and horizontal patterns in a tapered annular volume, which is show in cross section having opposite sides 3402 and 3403. In this example the density of the patterns increases moving along the AP from anterior to posterior. This combination of sectional patterns provides shaped structural weakening, where the higher density of the pattern provides greater structural weakening. This pattern will provide increased flexibility and increased refractive power.

Figure 23:
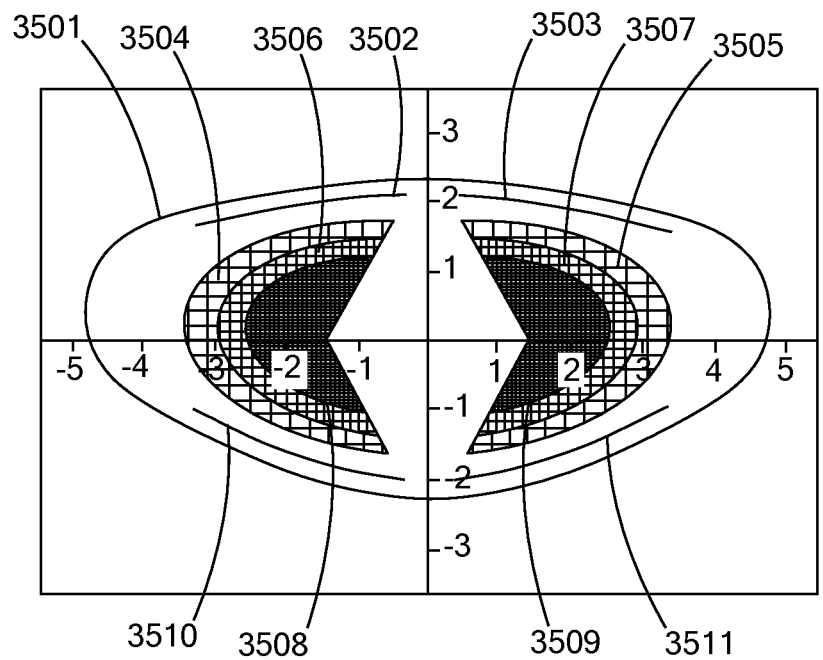
FIG. 23 is diagram illustrating a sectional shot pattern in accordance with the teachings of the present invention.

EXAMPLE 10, as illustrated in FIG. 23, provides within an outer lens surface 3501 a first primarily horizontal pattern 3502-3503, which is in the form of an annular partial shell having opposite sides 3502 and 3503 shown in cross section; a second primarily horizontal pattern 3510-3511, which is in the form of an annular partial shell having opposite sides 3510 and 3511 shown in cross section; and, a combination of partial vertical and partial horizontal patterns in a series of layers 3504-3505, 3506-3507, 3508-3509, in an annular shaped volume, with opposite sides shown in cross-section. The density of the patterns increases from 3504-3505 to 3506-3507 to 3508-3509. This combination of sectional patterns provides shaped structural weakening for increased flexibility and increased refractive power.

Figure 24:
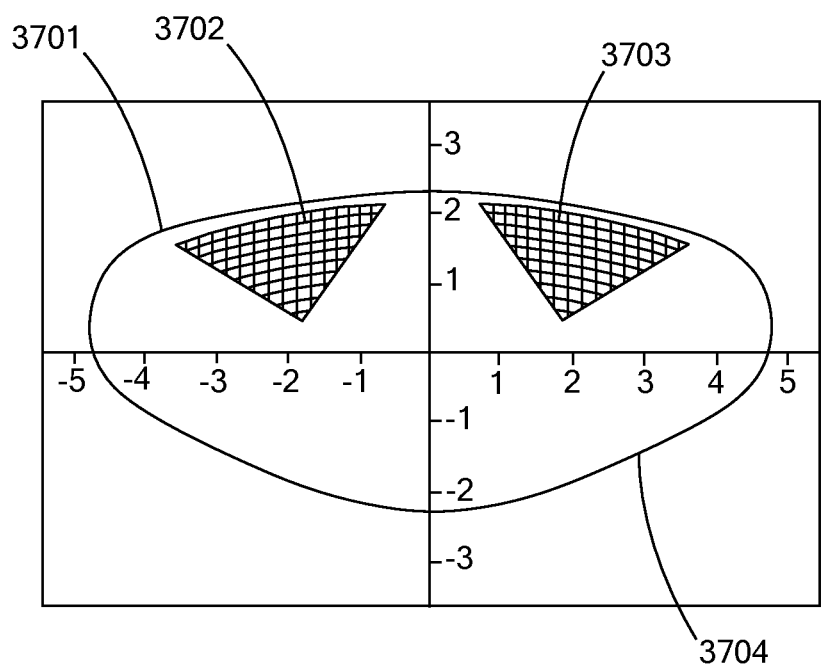
FIG. 24 is diagram illustrating a sectional shot pattern in accordance with the teachings of the present invention.

EXAMPLE 11, as illustrated in FIG. 24, provides in a lens having an outer surface 3701, a combination of primarily vertical and horizontal patterns in a tapered annular volume, which is show in cross section having opposite sides 3702 and 3703. In this example the density of the patterns is constant moving along the AP axis from anterior to posterior. This combination of sectional patterns provides shaped structural weakening for increasing flexibility and increasing refractive power.

Figure 25:
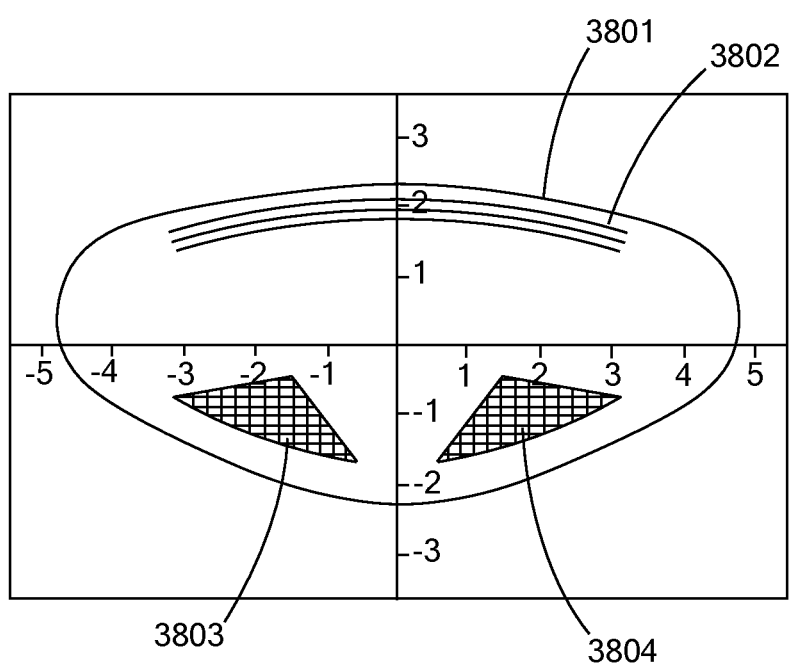
FIG. 25 is diagram illustrating a sectional shot pattern in accordance with the teachings of the present invention.

EXAMPLE 12, as illustrated in FIG. 25, provides in a lens having an outer surface 3801, a combination of first primarily horizontal patterns 3802 and a second tapered annular volume of primarily horizontal and primarily vertical patterns 3803-3804. This combination of sectional patterns provides shaped structural weakening for increased flexibility and increased refractive power. Thus, the first pattern is directed primarily toward increasing lens flexibility and the second pattern is directed primarily toward lens shape. Moreover, the central portion of the lens is reserved for later corrections.

Figure 26:
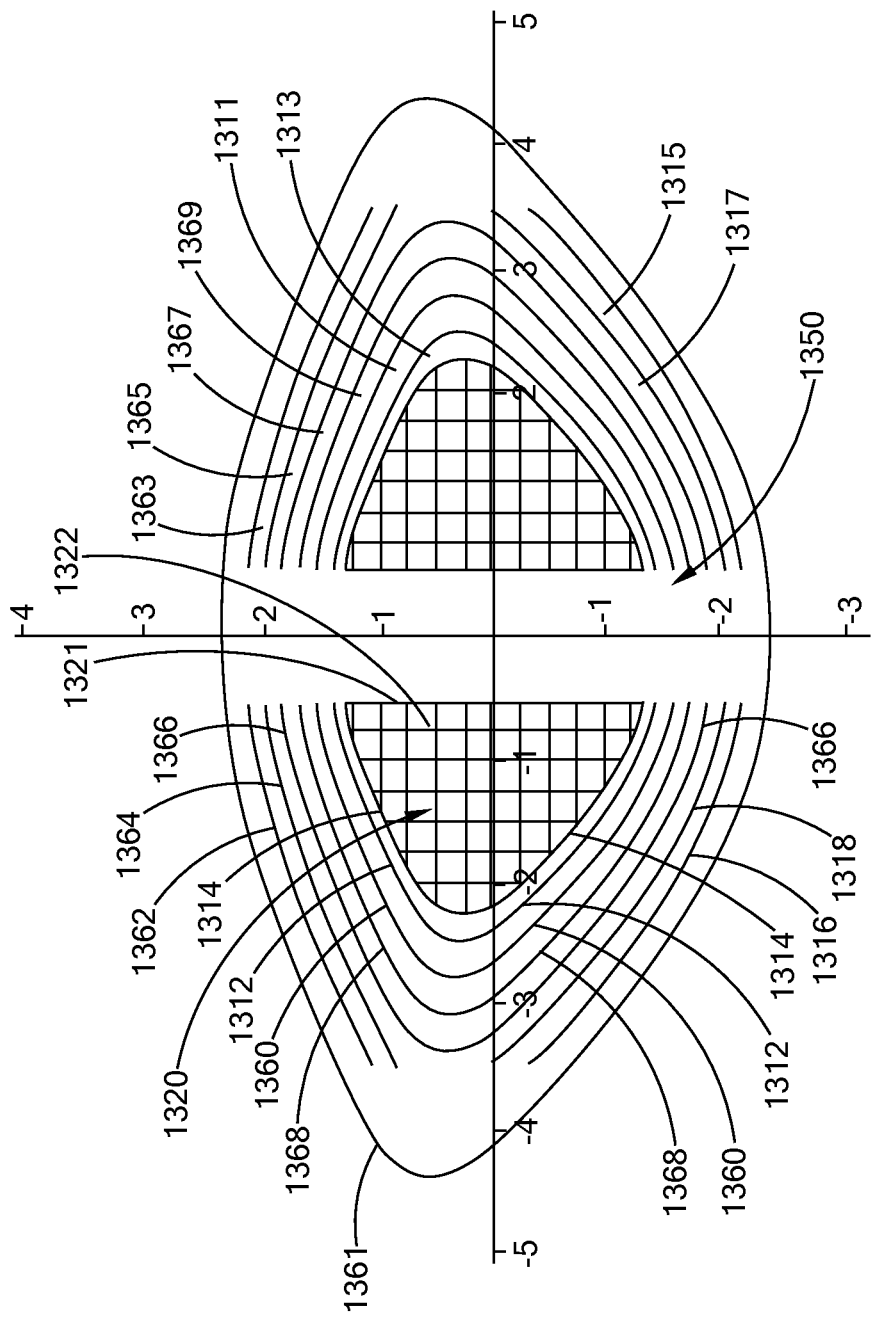
FIGS. 26-28 are cross-section drawings of lens illustrating a laser shot pattern in accordance with the teachings of the present invention.

EXAMPLE 13 provides for making of nested, lens shaped shell cuts in combination with cube shaped cuts. The laser shot patterns for this example are illustrated in FIG. 26. In this Figure there is shown the outer surface 1301 of a lens. There is further provided a series of nested or essentially concentric shells and shell cuts, which essentially follow the shape of the lens. Thus, there is provided annular shell cuts 1362, 1364, 1366, 1368, 1360, 1312, 1314, 1316, and 1318. Shell cuts 1362 and 1364 are positioned nearer to and follow the anterior surface of the lens, while shell cuts 1316 and 1318 are positioned nearer to and follow the posterior surface of the lens. Shell cuts 1366, 1368, 1360, 1312 and 1314 follow the entire curvature of the lens from anterior to posterior. The shell cuts form shells 1363, 1365, 1367, 1369, 1311, 1313, 1315, and 1317. These shells and shell cuts form annular structures but are illustrated in FIG. 26 in cross-section. As such, the shells or cuts on the left side of the figure correspond to, and are part of, the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 1320 of horizontal 1321 and vertical 1322 cuts. Shell cut 1314 borders and is joined with cube cuts 1321 and 1322. Such a shell cut may be, but is not required to be present. Further, as provided in FIG. 26, both these second cuts (cube cuts 1320) and the first cuts (shell cuts 1362, 1364, 1366, 1368, 1310, 1312, 1314, 1316, and 1318) are removed away from the optical axis of the lens by about 0.5 mm and thus form a cylinder of uncut lens material 1350 that has a radius of about 0.5 mm (diameter of about 1 mm). Thus, there is shown in this figure a plurality of cuts and cube pattern that provide a series of annular cuts surrounding a central portion of the lens that is not altered by the laser.

Figure 27:
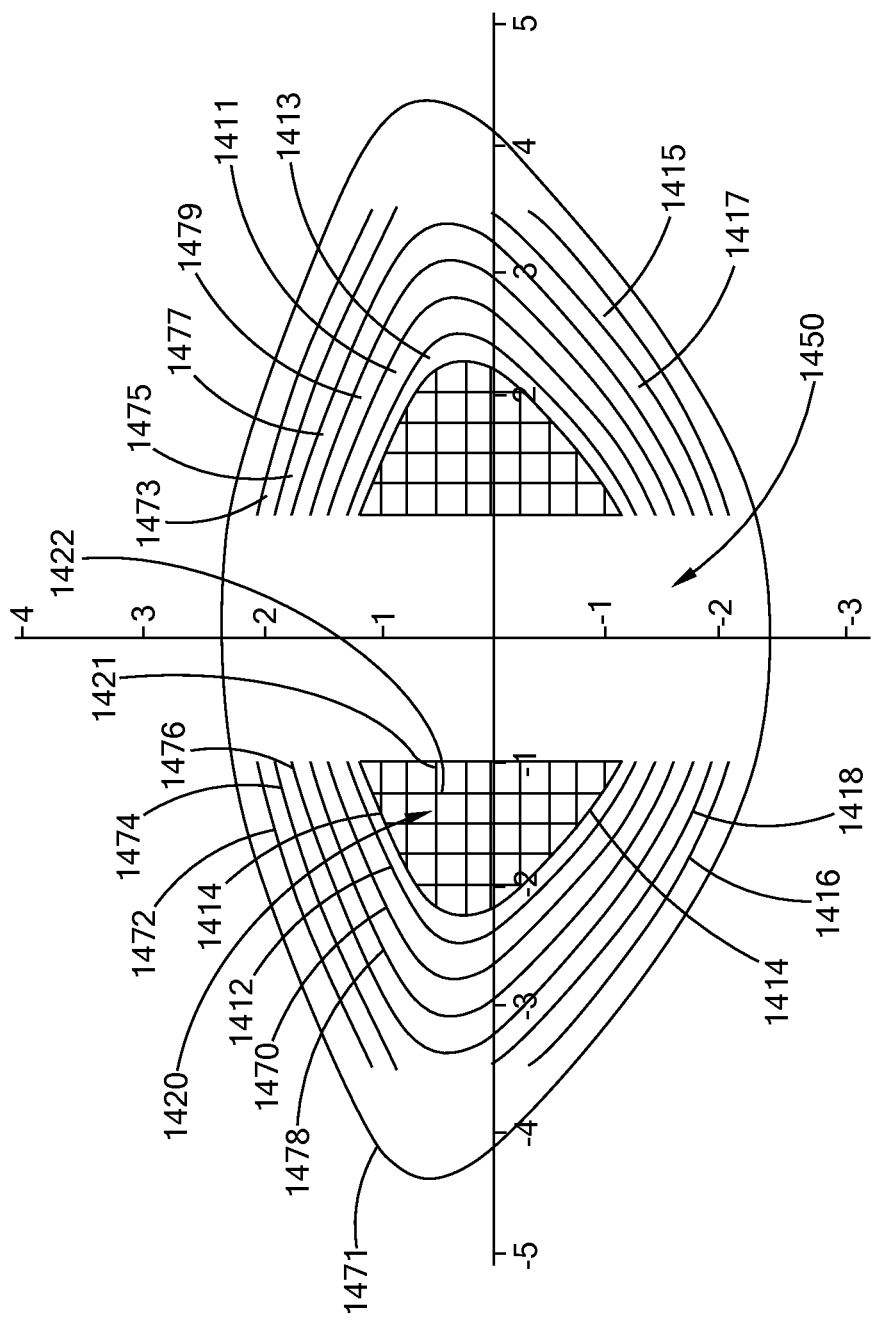

EXAMPLE 14 provides for making of nested, lens shaped shell cuts in combination with cube shaped cuts. The laser shot patterns for this example are illustrated in FIG. 27. In this Figure there is shown the outer surface 1471 of a lens. There is further provided a series of nested or essentially concentric shells and shell cuts, which essentially follow the shape of the lens. Thus, there is provided annular shell cuts 1472, 1474, 1476, 1478, 1470, 1412, 1414, 1416, and 1418. Shell cuts 1472 and 1474 are positioned nearer to and follow the anterior surface of the lens, while shell cuts 1416 and 1418 are positioned nearer to and follow the posterior surface of the lens. Shell cuts 1476, 1478, 1410, 1412 and 1414 follow the entire curvature of the lens from anterior to posterior. The shell cuts form shells 1473, 1475, 1477, 1479, 1411, 1413, 1415, and 1417. These shells and shell cuts form annular structures but are illustrated in FIG. 27 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 1420 of horizontal 1421 and vertical 1422 cuts. Shell cut 1414 borders and is joined with cube cuts 1421 and 1422. Such a shell cut may be, but is not required to be present. Further, as provided in FIG. 27, both these second cuts (cube cuts 1420) and the first cuts (shell cuts 1472, 1474, 1476, 1478, 1470, 1412, 1414, 1416, and 1418) are removed away from the optical axis of the lens by about 1 mm and thus form a cylinder of uncut lens material 1450 that has a radius of about 1 mm (diameter of about 2 mm). Thus, there is shown in this figure a plurality of cuts and cube pattern that provide a series of annular cuts surrounding a central portion of the lens that is not altered by the laser.

Figure 28:
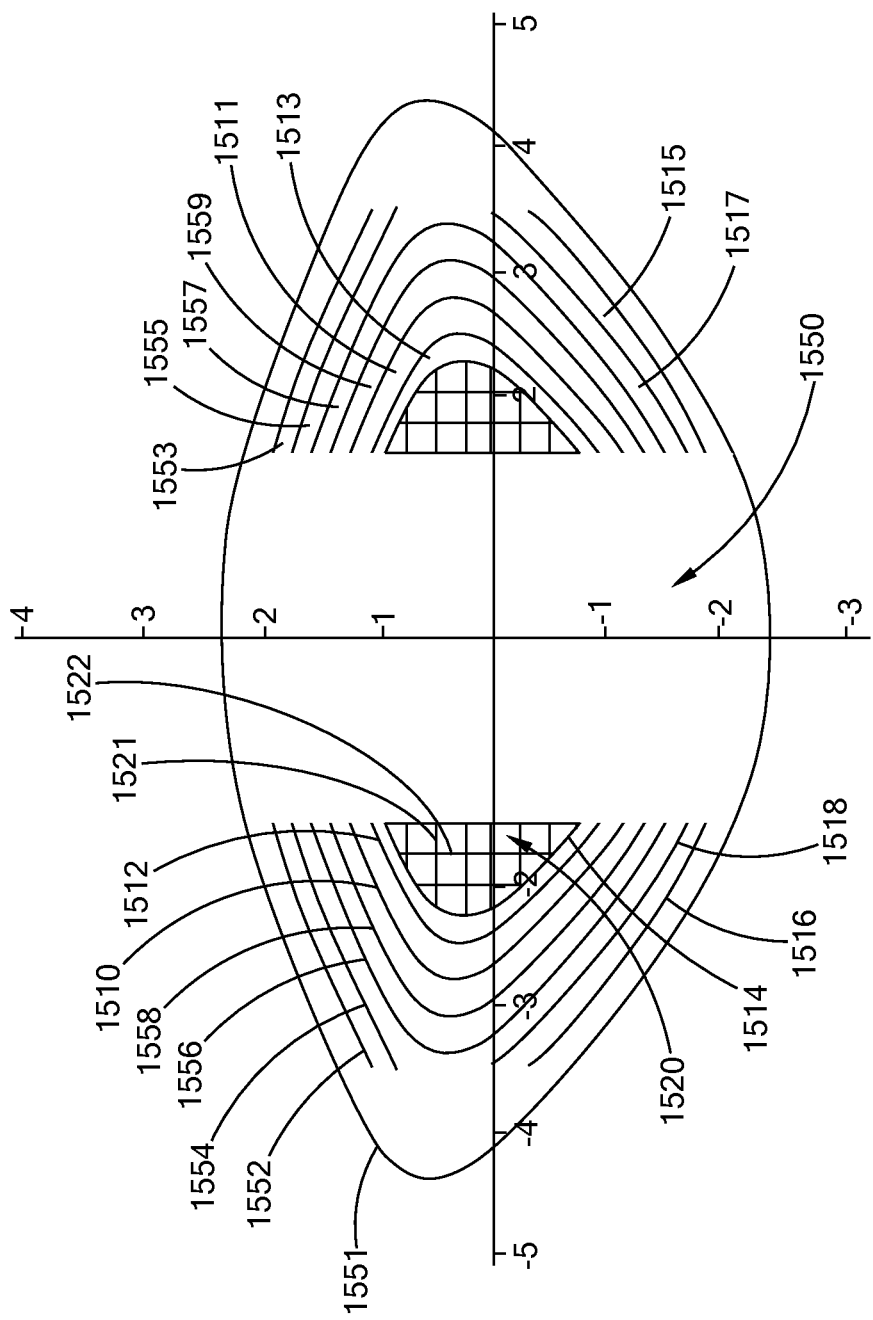

EXAMPLE 15 provides for making of nested, lens shaped shell cuts in combination with cube shaped cuts. The laser shot patterns for this example are illustrated in FIG. 28 In this Figure there is shown the outer surface 1551 of a lens. There is further provided a series of nested or essentially concentric shells and shell cuts, which essentially follow the shape of the lens. Thus, there is provided annular shell cuts 1552, 1554, 1556, 1558, 1550, 1512, 1514, 1516, and 1518. Shell cuts 1552 and 1554 are positioned nearer to and follow the anterior surface of the lens, while shell cuts 1516 and 1518 are positioned nearer to and follow the posterior surface of the lens. Shell cuts 1556, 1558, 1550, 1512 and 1514 follow the entire curvature of the lens from anterior to posterior. The shell cuts form shells 1553, 1555, 1557, 1559, 1511, 1513, 1515, and 1517. These shells and shell cuts form annular structures but are illustrated in FIG. 28 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 1520 of horizontal 1521 and vertical 1522 cuts. Shell cut 1514 borders and is joined with cube cuts 1521 and 1522. Such a shell cut may be, but is not required to be present. Further, as provided in FIG. 28, both these second cuts (cube cuts 1520) and the first cuts (shell cuts 1552, 1554, 1556, 1558, 1550, 1512, 1514, 1516, and 1518) are removed away from the optical axis of the lens by about 1.5 mm and thus form a cylinder of uncut lens material 1550 that has a radius of about 1.5 mm (diameter of about 3 mm). Thus, there is shown in this figure a plurality of cuts and cube pattern that provide a series of annular cuts surrounding a central portion of the lens that is not altered by the laser.

Figure 29:
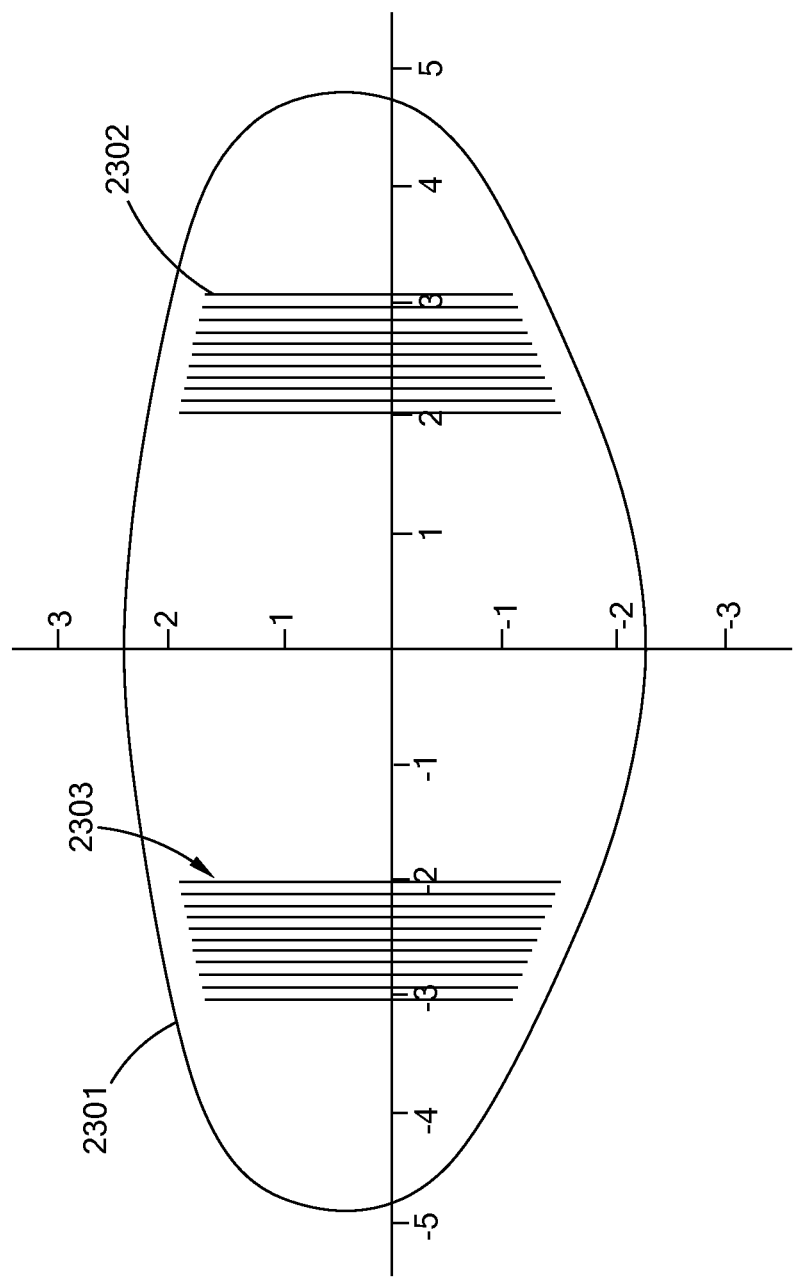
FIG. 29 is a cross-section drawing of lens illustrating vertical laser shot patterns in accordance with the teachings of the present invention.

EXAMPLE 16 There is provided an embodiment having the use of substantially vertical shot patterns, that is shot patterns that have cuts that are essentially parallel to the Optical axis of the eye. Thus, Example 10, which is illustrated in FIG. 29, provides an outer surface 2301 of a lens that has a shot pattern that has vertical cuts, e.g., 2302, arranged in a pattern that provides for an annular area of cutting 2303. These figures are show in cross-section and thus the pattern on the right side corresponds to the pattern on the left side. Moreover, as such the density of vertical cut is the same on the left and right side of the figures.

Various combinations of first and second shell cuts can be employed. Thus, the first and second patterns of any of the Examples may be used with any of the other first and second patterns of those examples. Similarly, any of these patterns may also be used in conjunction with the other patterns and teachings of patterns provided in this specification, including the patterns that are incorporated herein by reference. Moreover, when utilizing the teachings of these examples regarding varying or changing radii for uncut areas, the change in those radii per cut can be uniform, non-uniform, linear or non-linear. Moreover, such changes in radii per cut for either or both the interior radii (closest to the optical axis of the eye) or the outer radii can be the same from the anterior to the posterior side or the changes can be different from the anterior to posterior side cuts.

Although not bound by this theory, it theorized that increasing the deflection of the lens for a given load or zonule force will increase the flexibility of the lens structure and, in turn, the amplitude of accommodation for that same zonule force. Further, it is theorized that by providing these annular shells in conjunction with the cylindrical cuts and unaffected center portion of the lens, for example 1350, 1450, 1550, 1650, 1750, and 1850, that the shape of the lens will be altered in a manner that provides for an increase in the refractive power of the lens. Thus, the combination of these first and second cuts provides for both improved accommodative amplitude and increased refractive power of the lens.

A system and method for increasing the amplitude of accommodation and/or changing the refractive power of lens material of a natural crystalline lens is provided. Generally, there is provided methods and systems for delivering a laser beam to a lens of an eye in a plurality of sectional patterns results in the shaped structural weakening of the lens.

A system and method for increasing the amplitude of accommodation and/or changing the refractive power of a natural crystalline lens is provided. Generally, the system comprises a laser, optics for delivering the laser beam and a control system for delivering the laser beam to the lens in a particular pattern. There is further provided a device for determining the shape and position of the lens with respect to the laser. There is yet further provided a method and system for delivering a laser beam in the lens of the eye in a predetermined shot pattern that utilize as series of shots that form a shell cut, a partial shell cut, a laser suture cut and/or a volumetric shaped removal, which may essentially following the shape of a suture layer of the lens.

Accordingly, there are provided methods and systems for delivering a laser beam to a lens of an eye in a plurality of sectional patterns such that the laser beam is directed toward a first portion of the lens of the eye in a first predetermined sectional pattern and the laser beam is directed toward a second section of the lens of the eye in a second predetermined sectional pattern, which is different from the first pattern, wherein the combination and placement of the first and second sectional patterns results in the shaped structural weakening of the lens.

There is further provided a method and system for providing a first and a second sectional pattern to different portions of the lens of the eye resulting in shaped structural weakening of the lens that improves accommodative amplitude, refractive error or both refractive error and accommodative amplitude.

There is also provided a method and system for determining adjustments to refractive errors in the lens of an eye relating to the treatment of presbyopia that comprises a first shot pattern for the delivery of a laser to the lens of an eye for the purpose of improving accommodative amplitude of the lens, a second shot pattern for the delivery of a laser to the eye, such that the second shot pattern is based at least in part upon any change in refractive error as a result of the first shot pattern. The change to refractive error can be a predicted error or an actual error that has been determined.

Moreover, the timing of the delivery of the first and second shot patterns can be varied such that the first and second shot patterns are combined into a single pattern, the first shot pattern is delivered to the lens before the second shot pattern, the second shot pattern is delivered to the lens before the first shot pattern, the delivery of the first and second shot patterns are interspersed, e.g., one or more of shots of the first shot pattern are followed by one or more shots of the second shot pattern, which are then followed by one or more shots of the first pattern.

Accordingly, there are provided methods and systems for delivering a laser beam to a lens of an eye in a plurality of sectional patterns such that the laser beam is directed toward a first portion of the lens of the eye in a first predetermined sectional pattern and the laser beam is directed toward a second section of the lens of the eye in a second predetermined sectional pattern, which is different from the first pattern, wherein the combination and placement of the first and second sectional patterns results in the shaped structural weakening of the lens.

There is still further provided a method and system for providing a first and a second sectional pattern to different portions of the lens of the eye wherein the first pattern is directed primarily toward increasing lens flexibility and the second pattern is directed primarily toward lens shape, such as to preserve the lens shape or change the shape.

There is also provided a method and system for determining adjustments to refractive errors in the lens of an eye relating to the treatment of presbyopia that comprises a first shot pattern for the delivery of a laser to the lens of an eye for the purpose of improving accommodative amplitude of the lens, a second shot pattern for the delivery of a laser to the eye, such that the second shot pattern is based at least in part upon any change in refractive error as a result of the first shot pattern.

The change to refractive error can be a predicted error or an actual error that has been determined. Moreover, the timing of the delivery of the first and second shot patterns can be varied such that the first and second shot patterns are combined into a single pattern, the first shot pattern is delivered to the lens before the second shot pattern, the second shot pattern is delivered to the lens before the first shot pattern, the delivery of the first and second shot patterns are interspersed, e.g., one or more of shots of the first shot pattern are followed by one or more shots of the second shot pattern, which are then followed by one or more shots of the first pattern.

There is also provided a method and system for determining adjustments to refractive errors in the lens of an eye relating to the treatment of presbyopia that comprises a first shot pattern for the delivery of a laser to the lens of an eye for the purpose of improving accommodative amplitude of the lens, a second shot pattern for the delivery of a laser to the eye, such that the second shot pattern is based at least in part upon any change in refractive error as a result of the first shot pattern, wherein the first shot pattern is delivered to the lens, the change in refractive error is determined by observation of the lens after delivery of the first shot pattern, and the second shot pattern is then selected based at least in part upon said observed change in refraction. Accordingly, the second shot pattern can be delivered to the lens of the eye or to the cornea of the eye. Moreover, the laser for delivery of the first shot pattern and the laser for delivery of the second shot pattern may be different. As used herein the terms "first" and "second" as used to describe a "first shot pattern" and "second shot pattern," unless specifically provided otherwise, do not implicate timing, pattern sequence, or similarly or differences in lasers. These terms indicate that there are two patterns, one pattern which may be different from the other.

An embodiment of a system and method for increasing the amplitude of accommodation and/or changing the refractive power of lens material of a natural crystalline lens is provided. Generally, there is provided methods and systems for delivering a laser beam to a lens of an eye in a plurality of patterns results in the increased accommodative amplitude and/or refractive power of the lens. There is further provided a system and method of treating presbyopia by increasing both the flexibility of the human lens and the depth of field of the eye.

There is provided an embodiment of a system and method for delivering a laser beam to a lens of an eye in a plurality of patterns, which system and method in general comprise providing a laser, providing an optical path for directing a laser beam from the laser to the lens of the eye, directing the laser beam in a first pattern on a first portion of the lens of the eye, the first pattern generally following the shape of the outer surface of the lens of the eye, directing the laser beam in a second pattern on a second portion of the lens of the eye, the second pattern having a pattern to cover a specific volume of the second portion of the lens of the eye and wherein the relationship of the first pattern to the second pattern being such that the first pattern is positioned within the lens closer to the lens outer surface than the second pattern; and, both the first and second patterns positioned within the lens of the eye such that they avoid the central portion of the lens of the eye. In this system and method the second pattern may be cubic, the first shot pattern may be a plurality of nested shells, the first shot pattern may comprises a plurality of nested shells that follows the anterior surface of the lens of the eye, or other combinations and of patterns disclosed and taught herein. These shot patterns may further be delivered to the lens of the eye in a random manner. These shot patterns may still further have a central area avoided wherein the central area avoided has a width of about 1 mm centered approximately on the optical axis of the lens, wherein the central area avoided has is cylindrical in shape and has a diameter greater than about 1 mm centered approximately around the optical axis of the lens, wherein the central area avoided has a width of about 1.5 mm centered approximately on the optical axis of the lens, wherein the central area avoided is cylindrical in shape and has a diameter greater than about 1.5 mm centered approximately around the optical axis of the lens, wherein the central area avoided has a width of about 0.2 mm to about 4 mm centered approximately on the optical axis of the lens, wherein the central area avoided is cylindrical in shape and has a diameter of about 0.2 mm to about 4 mm centered approximately around the optical axis of the lens, wherein the central area avoided is cylindrical in shape and has a diameter of about 0.2 mm to about 4 mm centered approximately around the optical axis of the lens, wherein the central area avoided has a diameter of about 0.5 mm to about 3 mm centered approximately around the optical axis of the lens, wherein the central area avoided is cylindrical in shape and has a diameter of about 2 mm centered approximately around the optical axis of the lens, and wherein the second pattern is different from the first pattern, as well as other. These shot patterns may further be delivered to the lens of the eye in a random manner.

The various embodiments of devices, systems, laser shot patterns, activities, and operations set forth in this specification may be used with, in or by, various measuring, diagnostic, surgical and therapeutic laser systems, in addition to those embodiments of the Figures and disclosed in this specification. The various embodiments of devices, systems, laser shot patterns, activities, and operations set forth in this specification may be used with: other measuring, diagnostic, surgical and therapeutic systems that may be developed in the future: with existing measuring, diagnostic, surgical and therapeutic laser systems, which may be modified, in-part, based on the teachings of this specification; and with other types of measuring, diagnostic, surgical and therapeutic systems. Further, the various embodiments of devices, systems, laser shot patterns, activities, and operations set forth in this specification may be used with each other in different and various combinations. Thus, for example, the configurations provided in the various embodiments of this specification may be used with each other; and the scope of protection afforded the present inventions should not be limited to a particular embodiment, configuration or arrangement that is set forth in a particular embodiment, example, or in an embodiment in a particular Figure.

The inventions may be embodied in other forms than those specifically disclosed herein without departing from their spirit or essential characteristics. The described embodiments are to be considered in all respects only as illustrative and not restrictive.

What is claimed:

1. A system for increasing the accommodative amplitude of an eye, the system comprising:
   a. a laser for providing a laser beam;
   b. an optical path for delivery of the laser beam from the laser to a natural crystal lens of an eye;
   c. optics located along the optical path, the optics providing the capability to control the laser beam in the x, y and z directions;
   d. a control system comprising a laser beam delivery pattern, for directing the optics to deliver the laser beam in the laser beam delivery pattern to a predetermined area of the lens of the eye;
   e. the laser beam delivery pattern comprising a plurality of laser beam shots, the plurality of laser beam shots defining a first and a second area of the lens, the first area having an outer portion that essentially follows the curvature of the lens, the second area defining an excluded zone;
   f. whereby, the delivery of the laser beam in the laser beam pattern to the natural crystalline lens of the eye changes the flexibility and shape of the first area of the lens, thereby increasing the accommodative amplitude of the eye; and,
   g. wherein the first area has an inner diameter of 2 mm and an outer diameter of about 6 mm.

2. The system of claim 1, wherein the delivery of the laser beam in the laser beam pattern to the natural crystalline lens of the eye does not change the flexibility and shape of the second area of the lens.

3. A system for increasing the accommodative amplitude of an eye, the system comprising:
   a. a laser for providing a laser beam;
   b. an optical path for delivery of the laser beam from the laser to a natural crystal lens of an eye;
   c. optics located along the optical path, the optics providing the capability to control the laser beam in the x, y and z directions;
   d. a control system comprising a laser beam delivery pattern, for directing the optics to deliver the laser beam in the laser beam delivery pattern to a predetermined area of the lens of the eye;
   e. the laser beam delivery pattern comprising a plurality of laser beam shots, the plurality of laser beam shots defining a first and a second area of the lens, the first area having an outer portion that essentially follows the curvature of the lens, the second area defining an excluded zone;
   f. whereby, the delivery of the laser beam in the laser beam pattern to the natural crystalline lens of the eye changes the flexibility and shape of the first area of the lens, thereby increasing the accommodative amplitude of the eye; and,
   g. wherein the excluded zone comprises an axial excluded zone and an equatorial excluded zone.

4. The system of claim 3, wherein the axial excluded zone and the equatorial excluded zones intersect.

5. The system of claim 4, wherein the intersection includes the area defined by the middle of the equatorial axis and the AP axis of the lens.

6. The system of claim 3, wherein the delivery of the laser beam in the laser beam pattern to the natural crystalline lens of the eye does not change the flexibility and shape of the second area of the lens.

7. A system for increasing the accommodative amplitude of an eye, the system comprising:
   a. a laser for providing a laser beam;
   b. an optical path for delivery of the laser beam from the laser to a natural crystal lens of an eye;
   c. optics located along the optical path, the optics providing the capability to control the laser beam in the x and y directions;
   d. a control system comprising a laser beam delivery pattern, for directing the optics to deliver the laser beam in the laser beam delivery pattern to a predetermined area of the lens of the eye;
   e. the laser beam delivery pattern comprising a plurality of laser beam shots, the plurality of laser beam shots defining a first and a second area of the lens, the first area having an outer portion that essentially follows the curvature of the lens, the second area defining an excluded zone;
   f. comprising a position determination assembly;
   g. whereby, the delivery of the laser beam in the laser beam pattern to the natural crystalline lens of the eye changes the flexibility of and weakens the first area of the lens, thereby increasing the accommodative amplitude of the eye.

8. The system of claim 7, wherein the position determination assembly comprises: a light source to provide an illumination beam; an x, y, scanner; a z-focus device; an image capture device for providing observed data; a processor associated with the image capture device and capable of performing calculations, whereby the image capture device provides the observed data to the processor; the processor associated with a numerical model; and the processor capable of determining a position for a structure of the lens of the eye based upon the numerical model and the observed data.

9. The system of claim 8, wherein the light source is a coherent light source.

10. The system of claim 8, wherein the light source is a structured coherent light source.

11. The system of claim 8, wherein the light source is a structured coherent light source having a short coherence length.

12. The system of claim 8, wherein the light source is a laser diode.

13. The system of claim 8, wherein the light source is an infrared laser diode.

14. The system of claim 8, wherein the light source is a scanned infrared laser diode, whereby the scanned infrared laser diode defines a structured light source.

15. The system of claim 8, wherein the image capture device comprises a Scheimpflug camera.

* * * * *